(12) United States Patent
Hellerqvist et al.

(10) Patent No.: US 7,410,640 B2
(45) Date of Patent: Aug. 12, 2008

(54) GBS TOXIN RECEPTOR ANTIBODIES

(75) Inventors: Carl G. Hellerqvist, Brentwood, TN (US); Changlin Fu, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 65 days.

(21) Appl. No.: 10/823,506

(22) Filed: Apr. 12, 2004

(65) Prior Publication Data

US 2005/0002931 A1 Jan. 6, 2005

Related U.S. Application Data

(62) Division of application No. 09/359,167, filed on Jul. 21, 1999, now Pat. No. 6,803,448.

(60) Provisional application No. 60/093,843, filed on Jul. 22, 1998.

(51) Int. Cl.
*A61K 39/395* (2006.01)
*C07K 16/18* (2006.01)

(52) U.S. Cl. .............. 424/130.1; 530/387.1; 530/388.1; 530/387.3

(58) Field of Classification Search ........................ None
See application file for complete search history.

(56) References Cited

U.S. PATENT DOCUMENTS

| 4,242,326 | A | 12/1980 | Sugawara et al. |
|---|---|---|---|
| 5,010,062 | A | 4/1991 | Hellerqvist |
| 5,811,403 | A | 9/1998 | Hellerqvist |
| 5,858,991 | A | 1/1999 | Hellerqvist et al. |
| 5,939,396 | A | 8/1999 | Hellerqvist |

FOREIGN PATENT DOCUMENTS

| WO | WO 91/04048 | 4/1991 |
|---|---|---|
| WO | WO 97/41844 | 11/1997 |
| WO | WO 98/14603 | 4/1998 |
| WO | WO 98/32448 | 7/1998 |
| WO | WO 98/32452 | 7/1998 |
| WO | WO 98/32453 | 7/1998 |
| WO | WO 98/40487 | 9/1998 |

OTHER PUBLICATIONS

Devore et al., "Phase I Study of the Antineovascularization Drug CM101," *Clinical Cancer Research*, vol. 3, pp. 365-372 (1997).

Fu, et al., "Expressional Cloning of CM101 Receptor Gene from Mammalian Cells," *Proceedings of the American Association of Cancer Research*, Abstract 3677, vol. 40, p. 557 (1999).
Gearing, et al., "Expression Cloning of a Receptor for Human Granulocyte-Macrophage Colony-Stimulating Factor," *The EMBO Journal*, vol. 8, No. 12, pp. 3667-3676 (1989).
Hellerqvist et al., "Anti-Tumor Effects of GBS Toxin are Caused by Induction of a Targeted Inflammatory Reaction," *Angiogenesis: Molecular Biology, Clinical Aspects*, Edited by Maragoudakis et al., Plenum Press, New York, pp. 265-269 (1994).
Hellerqvist et al., "Antitumor Effects of GBS Toxin: A Polysaccharide Exotoxin From Group B β-Hemolytic *Streptococcus*," *J. Cancer Res. Clin. Oncol.*, vol. 120, pp. 63-70 (1993).
Hellerqvist et al., "Molecular Basis for Group B β-Hemolytic Streptococcal Disease," *Proc. Natl. Acad. Sci. USA*, vol. 84, pp. 51-55 (1987).
Hellerqvist et al., "Preliminary Results of a Phase I Trial of CM101 in Cancer Patients," *J. Cellular Biochemistry*, Suppl. 19B, p. 26 (1995).
Hellerqvist et al., "Studies on Group B β-Hemolytic *Streptococcus*. I. Isolation and Partial Characterization of an Extracellular Toxin," *Pediatr. Res.*, vol. 15. pp. 892-898 (1981).
Hillier, et al., "zr59d01.r1 Soares NhHMPu S1 *Homo sapiens* cDNA clone 667681 5' Similar to Tr:G507415 G507415 Brain Specific Na+-Dependent Inorganic Phosphate Cotransporter," Database EMBL—EMEST20 'Online!, Entry HS1173506, Acc. No. AA258513 (Mar. 19, 1997).
Kovacs et al., "Fibrogenic Cytokines and Connective Tissue Production," *The FASEB Journal*, vol. 8, pp. 854-861 (1994).
Norrby, "Angiogenesis: New Aspects Relating to Its Initiation and Control," *APMIS*, vol. 105, pp. 417-437 (1997).
Polverini, "The Pathophysiology of Angiogenesis," *Crit. Rev. Oral. Biol. Med.*, vol. 6, No. 3, pp. 230-247 (1995).
Quinn, et al., "CM101, A Polysaccharide Antitumor Agent, Does Not Inhibit Wound Healing in Murine Models," *J. Cancer Res. Clin. Oncol.*, vol. 121, pp. 253-256 (1995).
Thurman, et al., "Actue Inflammatory Changes in Subcutaneous Microtumors in the Ears of Mice Induced by Intravenous CM101 (GBS Toxin)," *J. Cancer Res. Clin. Oncol.*, vol. 122, pp. 549-553 (1996).
Wamil, et al., "Soluble E-Selectin in Cancer Patients as a Maker of the Therapeutic Efficacy of CM101, a Tumor-Inhibiting Anti-Neovascularization Agent, Elevated in Phase I Clinical Trail," *J. Cancer Res. Clin. Oncol.*, vol. 123, pp. 173-179 (1997).

*Primary Examiner*—Ruixiang Li
(74) *Attorney, Agent, or Firm*—Kilpatrick Stockton LLP

(57) ABSTRACT

A novel GBS toxin receptor and methods for its preparation and use are provided. GBS toxin receptor polynucleotides and polypeptides and antibodies to GBS toxin receptor are provided, as well as detection, screening, and therapeutic methods and pharmaceutical compositions involving such polynucleotides, polypeptides and antibodies.

10 Claims, 5 Drawing Sheets

Human Ovary Cancer+Pab 55

Normal Human Ovary+Pab 55

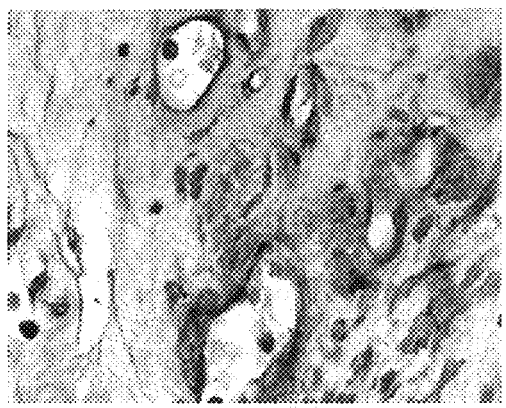 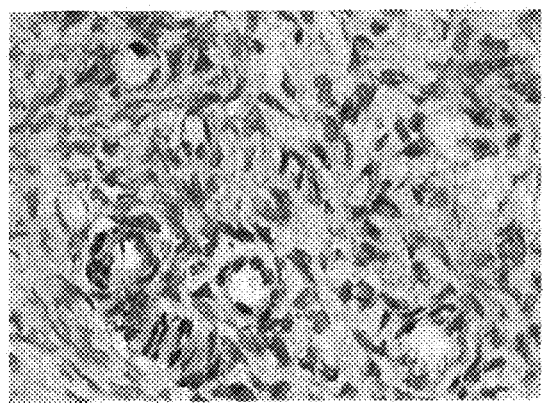
Human Ovary Cancer+Pab 57
Normal Human Ovary+Pab 57
Figure 3A
Figure 3B

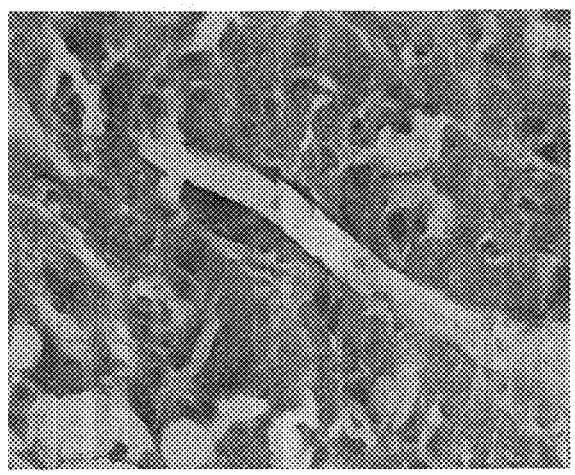 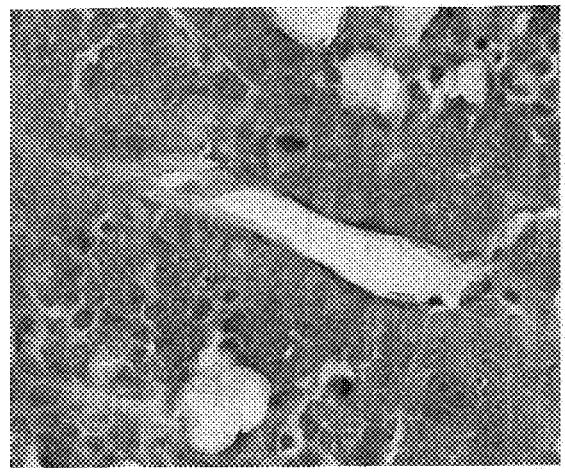
MLT CM101-Biot.5' +Strep.HRP
Figure 4A
MLT CM101-Biot. 5' + mAb
Figure 4B

GBS TOXIN RECEPTOR ANTIBODIES

CROSS REFERENCE TO RELATED APPLICATIONS

The present application is a divisional application of U.S. patent application Ser. No. 09/359,167, filed Jul. 21, 1999, issued as U.S. Pat. No. 6,803,448, which claims the benefit of U.S. Provisional Patent Application Ser. No. 60/093,843 filed Jul. 22, 1998 all of which are incorporated herein by reference in their entirety.

INTRODUCTION

1. Technical Field

This invention provides compositions and methods relating to GBS toxin receptor polynucleotides and polypeptides. The invention relates to a receptor for a polysaccharide isolated from a bacterial source.

2. Background

Group B β-hemolytic *Streptococci* (GBS) are ubiquitous microorganisms. GBS is not known to cause any harmful infections in humans except for very young babies. GBS pneumonia, also called "early-onset disease", is associated with high morbidity and mortality in newborn infants.

In a series of studies conducted by Dr. Carl G. Hellerqvist and his associates at the Vanderbilt University School of Medicine, Nashville, Tenn., a polysaccharide GBS toxin was identified. This toxin was determined to be a major factor in the complications of GBS pneumonia, and was found to be useful as a therapeutic agent in combating tumors though inhibition of vascularization (U.S. Pat. No. 5,010,062).

In addition, as described in U.S. Pat. No. 5,858,991 and WO98/32453, GBS toxin facilitates wound healing in patients by minimizing scarring and accelerating healing, and reduces wound-related tumor progression.

WO98/32452 and WO98/32448 describe the use of GBS toxin as a therapeutic agent for treating patients with chronic inflammatory diseases, such as rheumatoid arthritis and psoriasis, and for enhancing repair of neural injury.

Prior to this invention, receptors for GBS toxin had not been identified. The inventors, believing receptors of GBS toxin to reside on cells in the developing vasculature of tissues undergoing angiogenesis in the conditions described above, embarked upon a series of experiments resulting in the present invention.

SUMMARY OF THE INVENTION

For the first time, novel receptors for group B β-hemolytic *Streptococcus* GBS toxin (GBS toxin receptor) have been identified. One aspect of the invention provides a polypeptide comprising a GBS toxin receptor or polypeptide fragment thereof. Preferred embodiments include mammalian GBS toxin receptors. Also provided is an antibody that recognizes GBS toxin receptor or a fragment thereof. The polypeptide of the invention can be used, inter alia, for the screening of compounds that can be used to treat or prevent conditions arising from pathologic or hypoxia-driven angiogenesis or neovascularization, such as, for example, cancerous tumors, chronic inflammatory disease, scarring during wound healing, keloids, neural injury, and reperfusion injury.

Another aspect of the invention provides a polynucleotide encoding a GBS toxin receptor or a fragment thereof and a polynucleotide hybridizable to such polynucleotide. Preferred polynucleotides are at least 10 bases in length and comprise a nucleic acid sequence encoding, or are complementary to a nucleic acid sequence encoding, a mammalian GBS toxin receptor or a polypeptide fragment thereof.

A third aspect of the invention is a complex comprising a GBS toxin bound to a mammalian toxin receptor or fragment thereof. Also provided is a method of forming such complex. The method comprises contacting a GBS toxin with a polypeptide comprising a mammalian GBS toxin receptor, or fragment thereof that can bind GBS toxin, under conditions that permit specific binding of the GBS toxin to the polypeptide, and allowing the complex to form.

Yet another aspect of the invention is a method for purifying a compound that binds a GBS toxin receptor. The method comprises providing a polypeptide comprising a mammalian GBS toxin receptor, or fragment thereof that binds GBS toxin, contacting the polypeptide with a sample comprising the compound under conditions that allow specific binding of the compound to the polypeptide, and separating the bound compound from the remainder of the sample.

Another aspect of the invention is a method of determining the presence or absence of GBS toxin in a sample. The method comprises contacting the sample with a polypeptide comprising a mammalian GBS toxin receptor, or fragment thereof that binds GBS toxin, under conditions that allow specific binding of GBS toxin to the GBS toxin receptor, and determining whether specific binding of GBS toxin has occurred. Presence of GBS toxin in a sample obtained from a neonate is indicative of early onset disease.

A sixth aspect of the invention is a method for detecting pathologic vasculature in a mammalian tissue. The method comprises detecting the presence of a GBS toxin receptor. The method can be used for detecting or monitoring a variety of medical conditions associated with angiogenesis or neovascularization, such as, for example, detecting metastasis of a cancerous tumor, or monitoring the margin of a tumor in a mammal undergoing a therapy for cancer.

Another aspect of the invention provides methods for the identification of drug candidates for the treatment of medical conditions characterized by pathologic and/or hypoxia-driven angiogenesis or neovascularization. One embodiment is a method for identifying a compound that specifically binds a mammalian GBS toxin receptor. The method comprises combining a test compound with a mammalian GBS toxin receptor, or fragment thereof that can bind GBS toxin, under conditions that allow specific binding to occur, and detecting a complex formed between the test compound and the polypeptide. Another embodiment is a method for determining cytotoxicity of a test chimeric compound. The method comprises exposing a cell expressing a mammalian GBS toxin receptor, or fragment thereof that binds GBS toxin, to a test chimeric compound comprising a cytotoxic agent coupled to GBS toxin, and detecting signs of toxicity. Yet another embodiment is a method for identifying an inhibitor of a GBS toxin receptor by incubating test cells that express GBS toxin receptor, or a fragment thereof, in the presence and absence of a test compound and under conditions in which the cells incubated in the absence of the test compound can proliferate or migrate, and comparing the proliferation or migration of the test cells incubated in the presence and absence of the test compound, wherein less proliferation or migration in the presence of the test compound is indicative of the test compound being an inhibitor of the GBS toxin receptor. An inhibitor of endothelial cell proliferation or migration can be identified by the above method, wherein less proliferation or migration of test cells in the presence of the test compound is indicative of the test compound being an inhibitor of endothelial cell proliferation or migration. A therapeutic compound for the treatment or prevention of a medical condition characterized by pathologic angiogenesis or neovascularization can also be identified by the above method, wherein less proliferation or migration of test cells in the presence of the test compound is indicative of the test compound being a candidate therapeutic compound for the treatment or prevention of the medical condition.

The invention also provides a method for identifying a compound which inhibits binding of a GBS toxin to a mammalian GBS toxin receptor. The method comprises simulating and selecting the most probable conformations of a mammalian GBS toxin receptor, designing a chemically modified analog that substantially mimics the energetically most probable three-dimensional structure of the polypeptide, chemically synthesizing the analog, and evaluating the bioactivity of the analog. Also provided is a method for identifying a compound which binds to a mammalian GBS toxin receptor. The method comprises simulating and selecting the most probable conformations of a mammalian GBS toxin receptor, deducing the most probable binding domains of the polypeptide, designing a compound that would form the energetically most probable complexes with the polypeptide, chemically synthesizing the compound, and evaluating the bioactivity of the compound.

Another aspect of the invention is a method for the prevention or treatment of neonatal onset disease in a human neonate by administering an inhibitor of binding of GBS toxin to a human GBS toxin receptor.

Yet another aspect of the invention is a method for inhibiting pathologic or hypoxia-driven endothelial cell proliferation or migration in a mammalian tissue. The method comprises specifically binding a molecule to a GBS toxin receptor present on the surface of at least one cell in the tissue, the molecule being selected from the group consisting of a compound that can evoke an inflammatory response when bound to a GBS toxin receptor in a mammal, a chimeric compound comprising a cytotoxic compound coupled to a compound that specifically binds the GBS toxin receptor, an inhibitor of GBS toxin receptor phosphorylation, and an inhibitor of GBS toxin receptor activity.

The invention also provides a GBS toxin receptor or fragment thereof, an inhibitor of a GBS toxin receptor, or an inhibitor of binding of a GBS toxin to a GBS toxin receptor, for use in a method of treatment of the human or animal body or for the manufacture of a medicament for the treatment of a medical condition characterized by pathologic or hypoxia-driven angiogenesis or neovascularization. Also provided is a chimeric compound comprising a cytotoxic agent coupled to a compound that binds GBS toxin receptor for use in a method of treatment of the human or animal body.

Also provided are pharmaceutical compositions comprising an inhibitor of a GBS toxin receptor and/or a chimeric compound comprising a cytotoxic agent coupled to a compound that binds GBS toxin receptor, and a pharmaceutically acceptable carrier.

The invention also provides kits comprising a GBS toxin receptor or fragment and/or reagents for detecting the presence of a GBS toxin receptor or polypeptide fragment thereof or the presence of a polynucleotide encoding same.

BRIEF DESCRIPTION OF THE DRAWINGS

FIGS. 3A and 3B depict the results of immunohistochemical analysis of GBS toxin receptor expression in cancerous and normal human ovary tissue, respectively, using antibody Pab57 as described in Example 4.

FIGS. 4A-4C depict the targeted delivery of a chimeric compound to GBS toxin receptor expressed in a cancerous tissue as described in Example 6.

DESCRIPTION OF SPECIFIC EMBODIMENTS

Definitions

Figure 1:
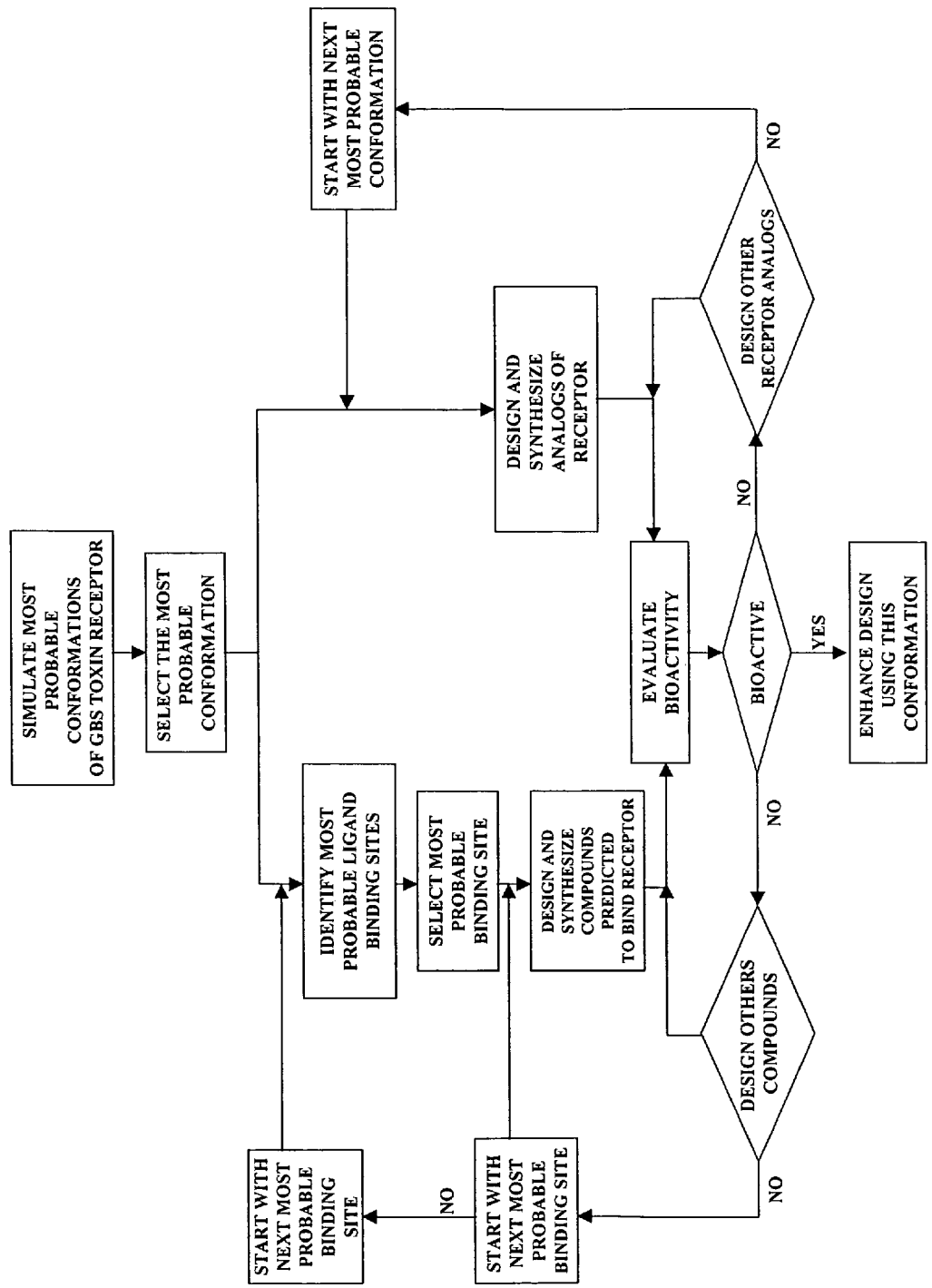
FIG. 1 depicts a process of rational drug design.

Generally, all technical and scientific terms used herein have the same meaning as commonly understood by one of ordinary skill in the art to which this invention belongs. The nomenclature used herein and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Enzymatic reactions and purification steps supplied by manufacturers are typically performed according to the manufacturer's specifications. The techniques and procedures are generally performed according to conventional methods in the art and various general references (See generally, Sambrook et al., *Molecular Cloning: A Laboratory Manual*, 2d ed. (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation described below are those well known and commonly employed in the art. Standard techniques can be used for chemical syntheses, chemical analyses, pharmaceutical formulation and delivery, and treatment of patients. As employed throughout the disclosure, the following terms, unless otherwise indicated, shall be understood to have the following meanings:

By "GBS toxin receptor" is meant a proteinaceous molecule capable of binding a toxin from Group B β-hemolytic *Streptococcus* bacteria (GBS toxin), such as, for example, CM101. A GBS toxin receptor is usually found in nature on the surface of a cell. Recombinant membrane bound and soluble GBS toxin receptors can be produced by laboratory techniques known in the art and described herein.

The term "isolated polynucleotide" referred to herein means a polynucleotide that has been subjected to manipulation, such that the isolated polynucleotide is no longer associated with the chromosome or cell that the polynucleotide is normally associated with in nature in the same manner as it is normally associated in nature. An example of an "isolated polynucleotide" is a polynucleotide of genomic, recombinant, or synthetic origin or some combination thereof.

The term "isolated protein" referred to herein means a protein that is no longer associated with the cell that the protein is normally associated with in nature in the same manner as it is normally associated in nature, such as (1) a protein free of at least some other proteins from the same source, (2) a protein expressed by a cell from a different species, (3) a protein that does not occur in nature, and (4) a protein produced from cDNA, recombinant RNA, or synthetic origin or some combination thereof.

The term "polypeptide" is used herein as a generic term to refer to native protein, fragments, or analogs of a polypeptide sequence. Hence, native protein, fragments, and analogs are species of the polypeptide genus.

The term "naturally occurring" means found in nature. For example, a polypeptide or polynucleotide sequence that is present in an organism (including viruses) found in nature and which has not been intentionally modified by man in the laboratory is naturally-occurring.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

The term "control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and can also include additional components whose presence is advantageous, for example, leader sequences and fusion partner sequences.

The term "polynucleotide" as referred to herein means a polymeric form of nucleotides of at least 10 bases in length, either ribonucleotides or deoxyribonucleotides or a modified form of either type of nucleotide. The term includes single- and double-stranded forms of DNA.

The term "oligonucleotide" referred to herein includes naturally occurring, and modified nucleotides linked together by naturally occurring and non-naturally occurring oligonucleotide linkages. An oligonucleotide is usually a polynucleotide 200 bases or fewer in length. Preferably oligonucleotides are minimally 10 to 60 bases in length and most preferably 15-35 bases in minimal length. Oligonucleotides are usually single-stranded, e.g. for probes; although oligonucleotides may be double-stranded, e.g. for use in the construction of a gene mutant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. An oligonucleotide can include a label for detection, if desired.

By "complementary" or "complement" is meant that wherever adenine appears in a first nucleic acid sequence, thymine or uracil is found in the "complementary" sequence and vice versa, and wherever guanine appears in a first nucleic acid sequence, cytosine is found in the "complementary" sequence and vice versa.

The term "sequence identity" describes the proportion of base matches between two nucleic acid sequences or the proportion of amino acid matches between two amino acid sequences, i.e. the degree of identity between two sequences. When sequence identity is expressed as a percentage, e.g., 50%, the percentage denotes the proportion of exact matches over the length of sequence from a GBS toxin receptor sequence that is compared to some other sequence. Various computer alignment programs can be used to determine sequence identity. In its simplest form, % identity is calculated by dividing the number of exact matches between two nucleic acid sequences or between two amino acid sequences by the total number of nucleotides or amino acids in the reference sequence. For example, if there are 300 matches between sequences 400 amino acids in length, the sequences have 75% identity. Uracil and thymine are considered identical when comparing a ribonucleic acid sequence with a deoxyribonucleic acid sequence.

As applied to polynucleotides, the term "substantial identity" means that two nucleic acid sequences when optimally aligned, such as by the program BLAST (Altschul et al., J. Mol. Biol. 215:403-410 (1990)), share at least about 85%, preferably at least about 90% sequence identity and most preferably 95% or greater sequence identity. When using computer alignment programs, gaps (in either of the two sequences) are permitted to maximize matching; gap lengths of 15 bases or less are usually used; 6 bases or less are preferred; 2 bases or less are most preferred. When using oligonucleotides as probes or in treatments, the sequence identity between the target nucleic acid and the oligonucleotide sequence is generally not less than 17 target base matches out of 20 possible oligonucleotide base pair matches (85%); preferably not less than 9 matches out of 10 possible base pair matches (90%), and most preferably not less than 19 matches out of 20 possible base pair matches (95%).

Preferably, bases which are not identical nevertheless are part of a degenerate codon that encodes the same amino acid at that amino acid position. Alternatively, bases which are not identical preferably are part of a degenerate codon that encodes a conservative amino acid substitution for that amino acid position.

As applied to polypeptides, the term "substantial identity" means that two peptide sequences, when optimally aligned by the BLAST computer program, share at least about 80 percent sequence identity, preferably at least about 86 percent sequence identity, more preferably at least about 95 percent sequence identity, even more preferably at least about 99 percent sequence identity up to having one amino acid difference, and most preferably share 100% identity. Gaps (in either of the two sequences being matched) are allowed in maximizing matching; gap lengths of 5 or less are preferred with 2 or less being more preferred. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acid substitution groups are: valine-leucine-isoleucine, phenylalanine-tyrosine, lysine-arginine, alanine-valine, glutamic-aspartic, and asparagine-glutamine.

The term "hybridizable under high stringency conditions" referred to herein means capable of specific binding under conditions whereby only nucleic acid sequences having a substantial identity of greater than 95% with respect to each other will hybridize. These conditions are known in the art and discussed herein.

The term "degenerate codon" means any of the nucleotide codon triplets encoding a desired amino acid according to the genetic code. Codons can be selected based upon known preferred codon usage in a host organism such as *E. coli.*

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length DNA sequence. Fragments typically are at least 3 amino acids long, preferably are 5-10 amino acids long, more preferably are 10-50 amino acids long, even more preferably are more than 50 amino acids long and comprise at least one extracellular domain of a GBS toxin receptor. Most preferred are fragments that comprise the entire extracellular domains of a GBS toxin receptor, and preferably also comprise portions of transmembrane and intracellular domains sufficient to maintain the polypeptide fragment in a functional stereochemical conformation on the surface of a cell, lipid membrane, liposome, micelle, or other lipophilic structure.

The term "immunologically reactive" means having antigenic properties or being capable of being specifically bound by an antibody that can specifically bind GBS toxin receptor. A substance has antigenic properties if it can generate monoclonal or polyclonal antibodies when administered to an animal under conditions known in the art to facilitate the production of antibodies that will recognize and bind a particular antigen.

A "heterologous polypeptide" is a polypeptide different from polypeptides normally produced by a particular cell. For example, a GBS toxin receptor polypeptide or fragment thereof that is produced recombinantly in a cell that does not normally produce such GBS toxin receptor polypeptide or fragment thereof, is a heterologous polypeptide. A second polypeptide joined to a GBS toxin receptor polypeptide or fragment thereof is also a heterologous polypeptide if it is not joined to a GBS toxin receptor polypeptide in nature.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3H$, $^{14}C$, $^{35}S$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "compound" as used herein preferably refers to a peptidic, peptidomimetic, organic, or other chemical molecule and also refers to a nucleic acid molecule or chemical derivative thereof. The compound can interact with, or be, the polynucleotides or polypeptides of the invention.

The singular forms "a", "an" and "the" include plural references unless the context clearly dictates otherwise.

The SEQ ID NOs of the nucleic acid and amino acid sequences described herein are summarized below in Table 1.

TABLE 1

Nucleic Acid and Amino Acid Sequences

| SEQ ID NO: | Type of Sequence | Description |
|---|---|---|
| SEQ ID NO: 1 | nucleic acid | Partial human GBS toxin receptor (HP55) |
| SEQ ID NO: 2 | amino acid | Partial human GBS toxin receptor (HP55) |
| SEQ ID NO: 3 | nucleic acid | Sheep GBS toxin receptor (SP55) |
| SEQ ID NO: 4 | amino acid | Sheep GBS toxin receptor (SP55) |
| SEQ ID NO: 5 | nucleic acid | Primer |
| SEQ ID NO: 6 | nucleic acid | Primer |
| SEQ ID NO: 7 | nucleic acid | Full-length human GBS toxin receptor (HP59) |
| SEQ ID NO: 8 | amino acid | Full-length human GBS toxin receptor (HP59) |
| SEQ ID NO: 9 | nucleic acid | Human/Sheep consensus GBS toxin receptor coding region (with base codes a, c, g, t, m, r, w, s, y, k) |
| SEQ ID NO: 10 | amino acid | Human/Sheep consensus GBS toxin receptor coding region (translation of SEQ ID No: 9) |
| SEQ ID NO: 11 | nucleic acid | Human/Sheep consensus GBS toxin receptor coding region (with base codes a, c, g, t, n) |
| SEQ ID NO: 12 | amino acid | Human/sheep consensus GBS toxin receptor coding region (translation of SEQ ID NO: 11) |

The headings provided herein describe the general topic discussed and are not intended to be exclusive of information discussed in other sections. Frequently, information, methods, compositions, and other aspects may be applicable to more than one embodiment of the invention and can be so combined.

Introduction

GBS toxin binds to tissues undergoing pathologic, hypoxia-driven, and embryologic angiogenesis or neovascularization. The inventors have identified at least two mammalian GBS toxin receptors, which are described herein. Examples 1 and 2 describe the cloning and characterization of some GBS toxin receptors. The inventors have classified GBS toxin receptor as an integral protein with seven transmembrane domains. The predicted segments are shown in Table 7. The protein has several putative sites for phosphorylation by cAMP-dependent kinase, protein kinase C (PKC), and casein kinase II (CK2). Typically, such integral proteins, upon binding of a molecule (e.g., a ligand or an extracellular messenger), undergo a conformational change which facilitates phosphorylation at phosphorylation sites such as those discussed above. The phosphorylation of the protein at these sites may trigger a signal transduction cascade, which often results in proliferation or other nuclear responses of the cells which have been exposed to the binding molecule. Angiogenesis or neovascularization involves proliferation and migration of endothelial cells. As discussed in greater detail in Examples 4 and 5, GBS toxin receptor expression is correlated with medical conditions involving pathologic, hypoxia-driven, and embryogenic angiogenesis or neovascularization. GBS toxin receptor polypeptides can be used for a variety of purposes, including screening for compounds that can inhibit endothelial cell proliferation and/or migration mediated by GBS toxin receptor and screening for cytotoxic chimeric compounds that can bind to and destroy cells expressing GBS toxin receptor. GBS toxin receptor polynucleotides can be used for a variety of purposes, including the design of antisense polynucleotides that can block translation of messenger RNA encoding GBS toxin receptor.

Polynucleotides

One aspect of the invention provides for isolated polynucleotides at least ten bases in length encoding or complementary to a nucleic acid sequence encoding a GBS toxin receptor or a fragment derived therefrom. Preferably, the GBS toxin receptor is a mammalian GBS toxin receptor, more preferably an ovine, bovine or feline GBS toxin receptor, and most preferably a human GBS toxin receptor. The isolated polynucleotides can be naturally occurring or non-naturally occurring. The isolated polynucleotides can comprise a DNA sequence or an RNA sequence in which every T is replaced with U. For purposes of determining percentage identity, T is considered equivalent to U. Preferably, the polynucleotides include alleles of an ovine, bovine, feline or human GBS toxin receptor, and can include alleles of GBS toxin receptor of other mammals. These polynucleotides can be isolated using polynucleotides derived from SEQ ID NOs: 1, 3, 7, 9 and 11, as described further below.

Polynucleotides, oligonucleotides and fragments of the invention selectively hybridize to nucleic acid strands under hybridization and wash conditions that minimize appreciable amounts of detectable binding to nonspecific nucleic acids. The polynucleotides can be hybridizable under high stringency conditions to a nucleic acid molecule having a nucleic acid sequence comprising at least 20 contiguous polynucleotides, preferably at least 30 contiguous nucleotides of SEQ ID NO: 1 or SEQ ID NO: 3, and even more prefereably to the nucleic acid sequence of SEQ ID NO: 1, 3, 7, 9 or 11 or the complement of SEQ ID NO: 1, 3, 7, 9 or 11. Such polynucleotides can be used for performing selective, high stringency hybridization and are particularly useful for performing amplification of nucleic acid by polymerase chain reaction (PCR) to determine the presence or absence of GBS toxin receptor in a sample, for isolating a naturally occurring nucleic acid encoding a GBS toxin receptor (see Example 3), as antisense molecules for blocking translation of GBS toxin receptor mRNA. Particularly preferred are polynucleotides hybridizable under high stringency conditions to a nucleic acid molecule having a nucleic acid sequence comprising the nucleic acid sequence of nucleotides 266 to 1870 of SEQ ID NO: 7 (the putative full length coding region of a human GBS toxin receptor, excluding the start codon), nucleotides 266 to 1870 of SEQ ID NO:7 (the putative full length coding region of a human GBS toxin receptor, including the start codon), nucleotides 61 to 1542 of SEQ ID NO:1 (the partial coding region of a human GBS toxin receptor, excluding the start codon), nucleotides 58 to 1542 of SEQ ID NO: 1 (the partial coding region of a human GBS toxin receptor, including the start codon), nucleotides 87 to 1568 of SEQ ID NO: 3 (the coding region of a sheep GBS toxin receptor, excluding the start codon), nucleotides 84 to 1568 of SEQ ID NO:3 (the coding region of a sheep GBS toxin receptor, including the start codon), or a complementary nucleic acid sequence thereof.

The polynucleotides can have an identity to the nucleic acid sequence of a corresponding region of SEQ ID NO: 1, 3 or 7 or the complement of a corresponding region of SEQ ID NO: 1, 3 or 7 in the range of about 85% to 100%, preferably greater than about 87% identity, more preferably greater than about 95% identity, and most preferably about 99% to 100% identity. Particularly preferred are polynucleotides comprising the nucleic acid sequence of nucleotides 266 to 1870 of SEQ ID NO: 7, or nucleotides 87 to 1568 of SEQ ID NO: 3, SEQ ID NO: 9, SEQ ID NO:11, or a complementary nucleic acid sequence thereof.

Preferably, the polynucleotides comprise a nucleic acid sequence encoding, or complementary to a nucleic acid sequence encoding, a polypeptide having an identity to the amino acid sequence of a fragment of a GBS toxin receptor in the range of about 85% to 100%, more preferably greater than 86% identity, even more preferably greater than 95% identity, and most preferably 99% to 100% identity. Preferably, the fragment binds GBS toxin. Preferred fragments comprise all or a portion of residues 1 to 495 of SEQ ID NO: 2 or all or a portion of residues 1 to 536 of SEQ ID NO: 8. Particularly preferred are polynucleotides comprising a nucleic acid sequence encoding a polypeptide having 100% identity to the amino acid sequence of residues 1 to 495 of SEQ ID NO: 4, residues 1 to 495 of SEQ ID NO: 2, or residues 1 to 536 of SEQ ID NO:8.

Polynucleotides encoding naturally occurring GBS toxin receptor can be isolated from various tissue sources and cell cultures from different species that produce such a receptor by the methods described herein, such as, for example, cells from tumor endothelium, synovial tissue in rheumatoid arthritis, or hypoxic tissue deprived of or restricted from blood flow, such as in reperfusion injury or wounded tissue. Such polynucleotides can be isolated by hybridization using probes or by polymerase chain reaction using oligonucleotides, as well as by implementing other molecular biology techniques known in the art. Such probes and oligonucleotides typically comprise various regions of the sequence of SEQ ID NO: 1, 3, 7, 9 or 11, preferably of SEQ ID NO: 1, 3, or 7, or encode various regions of the sequence of SEQ ID NO. 2, 4, 8, 10 or 12, preferably of SEQ NO: 2, 4 or 8.

Polynucleotides useful for cloning genes encoding GBS toxin receptors of various organisms can be determined by comparing the amino acid sequences of homologous proteins. (see Table 4). For example, conserved regions can be targeted for the synthesis of oligonucleotides or degenerate oligonucleotides to be used as probes for hybridization or nucleic acid amplification, techniques discussed further below and in Example 3. Stringency can be varied to achieve selective hybridization conditions whereby nucleic acid sequences having less than 95% identity with respect to each other will hybridize. These conditions are known in the art and discussed herein and examples are provided. Generally, the nucleic acid sequence identity between the polynucleotides, oligonucleotides, and fragments of the invention and a nucleic acid sequence of interest will be at least about 85%, and more typically with preferably increasing identities of at least about 90%, 95%, 99%, and 100%.

Polynucleotides can be used as probes under high stringency wash conditions and with corresponding hybridization conditions, as known in the art. Small polynucleotides, for example, polynucleotides 200 bases or fewer in length, are often referred to in the art as oligonucleotides. Techniques for using polynucleotides as probes to detect the same or related nucleic acid sequences is well known in the art. See, for example, Sambrook et al, especially Chapter 11, the text of which is herein incorporated by reference. Usually, probes can be made from polynucleotides that are 10 to 200 bases in length. Preferably probes are made from polynucleotides 10 to 60 nucleotides in length and most preferably 12 to 40 bases in length. Specific probes can be designed based on results obtained using nucleic acid homology computer programs such as FASTA, which uses the method of Pearson and Lipman (*Proc. Natl. Acad. Sci. USA* 85:2444-2448 (1988)) and shows the degree of identity between compared sequences.

The size of the probe is dependent upon the region of the gene to which it will be hybridized. The size of the probe increases as the degree of homology to undesirable nucleic acid sequences increases. A probe 10-50 nucleotides in length can be used, preferably more than 50 nucleotides, even more preferably more than 100 nucleotides, and most preferably a probe made from the entire coding region of a GBS toxin receptor will be used. To decrease the number of false positives, preferably two probes are used to identify clones that bind to both probes under hybridization and wash conditions. Oligonucleotides can be synthesized on an Applied BioSystems oligonucleotide synthesizer according to specifications provided by the manufacturer.

Typically, hybridization and washing conditions are performed at according to conventional hybridization procedures. Typical hybridization conditions for screening plaque lifts (Benton and Davis (1978) Science 196: 180) can be: 50% formamide, 5×SSC (sodium chloride, sodium citrate) or SSPE (sodium chloride, sodium phosphate, EDTA), 1-5× Denhardt's solution, 0.1-1% SDS, 100-200 µg sheared heterologous DNA or tRNA, 0-10% dextran sulfate, $1\times10^5$ to $1\times10^7$ cpm/ml of denatured probe with a specific activity of about $1\times10^8$ cpm/µg, and incubation at 42° C. for about 6-36 hours. Prehybridization conditions are essentially identical except that probe is not included and incubation time is typically reduced. Washing conditions are typically 1-3×SSC, 0.1-1% SDS, 42-70° C. with change of wash solution at about 5-30 minutes. Cognate bacterial sequences, including allelic sequences, can be obtained in this manner. For high stringency hybridization conditions, various parameters can be altered to increase the stringency of hybridization, such as by increasing the temperature of incubation with the labeled probe. Preferably, for greater flexibility in experimental design, the probe can be hybridized at a lower temperature, such as, for example, room temperature and the stringency can then be modified by altering the salt concentration and temperature of the wash solutions. For high stringency a wash temperature of greater than or equal to 42° C. can be used, such as, for example, 68° C., in a wash buffer having a salt concentration less than 3×SSC, such as, for example, 0.1× SSC. In some cases, TMACL can also be used, particularly for polynucleotides rich in G-C base pairs in order to decrease non-specific binding. A lower stringency wash can be used to hybridize polynucleotides with lower identities or polynucleotides that are less than 60 base pairs in length. For a low stringency wash, temperatures of less than or equal to 42° can be used in a wash buffer having a salt concentration of greater than or equal to 2×SSC.

The invention includes methods for amplification of target nucleic acids, such as the polymerase chain reaction ("PCR") technique. The PCR technique can be applied to identify related sequences in the genomes of various organisms and to detect nucleotide sequences in suspected samples, using oligonucleotide primers spaced apart from each other and based on the genetic sequence set forth herein. The primers are complementary to opposite strands of a double-stranded DNA molecule and are typically separated by from about 50 to 450 nucleotides or more (usually not more than 2000 nucleotides). This method entails preparing the specific oligonucleotide primers followed by repeated cycles of target DNA denaturation, primer binding, and extension with a DNA polymerase to obtain DNA fragments of the expected length based on the primer spacing. Extension products generated from one primer serve as additional target sequences for the other primer. The degree of amplification of a target sequence is controlled by the number of cycles that are performed and is theoretically calculated by the simple formula 2n where n is the number of cycles. Given that the average efficiency per cycle ranges from about 65% to 85%, 25 cycles produce from 0.3 to 4.8 million copies of the target sequence. The PCR method is described in a number of publications, including Saiki et al., Science (1985) 230:1350-1354; Saiki et al., Nature (1986) 324:163-166; and Scharf et. al., Science (1986) 233:1076-1078. Also see U.S. Pat. Nos. 4,683,194; 4,683,195; and 4,683,202, the text of each patent is herein incorporated by reference. Additional methods for PCR amplification are described in: PCR Technology: Principles and Applications for DNA Amplification ed. H A Erlich, Freeman Press, New York, N.Y. (1992); PCR Protocols: A Guide to Methods and Applications, eds. Innis, Gelfland, Snisky, and White, Academic Press, San Diego, Calif. (1990); Mattila et al. (1991) Nucleic Acids Res. 19: 4967; Eckert, K. A. and Kunkel, T. A. (1991) PCR Methods and Applications 1: 17, and; PCR, eds. McPherson, Quirkes, and Taylor, IRL Press, Oxford, all of which are incorporated herein by reference.

In yet another embodiment, an antisense polynucleotide can be administered to a mammal to treat or prevent a medical condition involving pathologic and/or hypoxia-driven angiogenesis. The antisense oligonucleotides of the invention can be synthesized by any of the known chemical oligonucleotide synthesis methods. Such methods are generally described, for example, in Winnacker, From Genes to Clones: Introduction to Gene Technology. VCH Verlagsgesellschaft mbH (H., Ibelgaufts trans. 1987). Any of the known methods of oligonucleotide synthesis can be utilized in preparing the instant antisense oligonucleotides. The antisense oligonucleotides are most advantageously prepared by utilizing any of the commercially available, automated nucleic acid synthesizers. The device utilized to prepare the oligonucleotides described herein, the Applied Biosystems 380B DNA Synthesizer, utilizes—cyanoethyl phosphoramidite chemistry. Antisense oligonucleotides hybridizable with any portion of the mRNA transcript can be prepared by the oligonucleotide synthesis methods known to those skilled in the art. While any length oligonucleotide can be utilized in the practice of the invention, sequences shorter than 12 bases may be less specific in hybridizing to the target GBS toxin receptor mRNA, and may be more easily destroyed by enzymatic digestion. Hence, oligonucleotides having 12 or more nucleotides are preferred. Sequences longer than 18 to 21 nucleotides may be somewhat less effective in inhibiting GBS toxin receptor translation because of decreased uptake by the target cell. Thus, oligomers of 12-21 nucleotides are most preferred in the practice of the present invention, particularly oligomers of 12-18 nucleotides. Oligonucleotides complementary to and hybridizable with any portion of the GBS toxin receptor mRNA transcript are, in principle, effective for inhibiting translation of the transcript, and capable of inducing the effects herein described. Translation is most effectively inhibited by blocking the mRNA at a site at or near the initiation codon. Thus, oligonucleotides complementary to the 5' region of the GBS toxin receptor mRNA transcript are preferred. Secondary or tertiary structure which might interfere with hybridization is minimal in this region. Moreover, sequences that are too distant in the 3' direction from the initiation site can be less effective in hybridizing the mRNA transcripts because of a "read-through" phenomenon whereby the ribosome is postulated to unravel the antisense/sense duplex to permit translation of the message. (see, e.g. Shakin, J. Biochemistry 261, 16018 (1986)). The antisense oligonucleotide is preferably directed to a site at or near the ATG initiation codon for protein synthesis. Oligonucleotides complementary to a portion of the GBS toxin receptor mRNA including the initiation codon are preferred. While antisense oligomers complementary to the 5' region of the GBS toxin receptor transcript are preferred, particularly the region including the initiation codon, it should be appreciated that useful antisense oligomers are not limited to those complementary to the sequences found in the translated portion of the mRNA transcript, but also includes oligomers complementary to nucleotide sequences contained in, or extending into, the 5' and 3' untranslated regions. Antisense nucleotides or antisense expression constructs can find use to treat or prevent diseases associated with pathologic or hypoxia-driven angiogenesis and neovascularization, as inappropriate expression of GBS toxin receptor results in hyperproliferation of endothelial cells.

In one embodiment, the polynucleotides of the invention can exist in linear form. In another embodiment, the polynucleotides can exist in circular form as part of a plasmid.

In yet another embodiment, a probe or PCR primer comprises a group of polynucleotide species containing different degenerate codons at various positions, which polynucleotides encode, or are complementary to sequences encoding, a GBS toxin receptor in whole or in part. Such polynucleotides can be useful for isolating nucleic acid sequences encoding polypeptides having at least about 85% identity to the amino acid sequence of sheep or human GBS toxin receptor, such as, for example, GBS toxin receptors of other organisms. Typically, such polynucleotides are synthesized chemically as described above by programming a synthesizer to incorporate a particular combination of nucleic acid residues at a certain position. Typical designations are shown in Table 2.

TABLE 2

Base Codes

| Symbol | Meaning |
|---|---|
| A | A; adenine |
| C | C; cytosine |
| G | G; guanine |
| T | T; thymine |
| U | U; uracil |
| M | A or C |
| R | A or G |
| W | A or T/U |
| S | C or G |
| Y | C or T/U |
| K | G or T/U |
| V | A or C or G; not T/U |
| H | A or C or T/U; not G |
| D | A or G or T/U; not C |
| B | C or G or T/U; not A |
| N | A or C or G or T/U |

Polypeptides

Another aspect of the invention provides polypeptides comprising (1) the full length GBS toxin receptor protein or a naturally occurring allelic variant thereof, (2) fragments of at least 3 amino acids of the amino acid sequence of SEQ ID NO: 2, 4, 8, 10 or 12, and (3) a GBS toxin receptor protein, polypeptide, or polypeptide fragment having an amino acid identity in the range of about 80% to 100% to the amino acid sequence of a corresponding region of SEQ ID NO: 2, 4 or 8. Preferred fragments of the amino acid sequence of SEQ ID NO: 2, 4, 8, 10 or 12, are at least 5, 6, 7, 8 or 9 amino acids in length and are immunologically reactive, i.e., immunogenic. More preferred are fragments at least 25 amino acids in length and fragments comprising the amino acid sequence of residues 181 to 419 of SEQ ID NO: 2 or residues 1 to 240 of SEQ ID NO: 4. Most preferred are fragments that can bind GBS toxin. Preferably, the GBS toxin receptor protein, polypeptide, or polypeptide fragment has an amino acid identity to the amino acid sequence of a corresponding region of SEQ ID NO: 2, 4 or 8 of at least about 86%, more preferably at least about 95% identity, even more preferably at least about 99% identity up to having one amino acid difference, and most preferably 100% identity. Preferred polypeptides have at least about 89% identity, more preferably at least about 95% identity, even more preferably at least about 99% identity up to having one amino acid difference, and most preferably 100% identity to the amino acid sequence of residues 181 to 419 of SEQ ID NO: 2, residues 1 to 495 of SEQ ID NO: 4. Preferably, a full length GBS toxin receptor protein comprises the amino acid sequence of residues 1 to 495 of SEQ ID NO: 2, residues 1 to 495 of SEQ ID NO: 4, or residues 1 to 536 of SEQ ID NO: 8, or an allelic variant thereof. The polypeptides of the invention can include amino acids in addition to the GBS toxin receptor protein, polypeptide, or polypeptide fragment. Such polypeptides typically comprise a heterologous polypeptide joined to a second polypeptide derived, as described above, from a GBS toxin receptor. Preferably the additional amino acids are covalently linked to the amino-terminal or carboxy-terminal terminus of the GBS toxin receptor protein, polypeptide, or polypeptide fragment.

Fragments or analogs of GBS toxin receptor can be prepared by those of ordinary skill in the art. Preferred amino- and carboxy-termini of fragments or analogs occur near boundaries of functional domains. For example, such functional domains include domains conferring the property of induction of an inflammatory response upon binding of GBS toxin to the GBS toxin receptor. GBS toxin mediates the binding and opsonization by C3 of endothelial cells that express the GBS toxin receptor. Such domains can comprise the binding site for GBS toxin, in whole or in part, or domains otherwise essential for GBS toxin receptor structure and/or function. Preferably, computerized comparison methods are used to identify sequence motifs or predicted protein conformation domains that occur in other proteins of known structure and/or function. Methods to identify protein sequences that fold into a known three-dimensional structure are known (Bowie et al. (1991) *Science* 253: 164). Computerized prediction methods, such as, for example, a hydropathy profile as provided by the "Soap" program in PC/GENE can be employed to identify putative structural and functional domains. Using the method of Klein, Kanehisa and DeLise, Biochim Biophys Acta (1985) 815:468-476, the inventors have classified a sheep GBS toxin receptor, SP55, as an integral protein with seven transmembrane segments predicted. Such a protein is also known colloquially in the art as a "7-spanner". The predicted segments are set forth below in Table 3.

TABLE 3

Predicted Transmembrane Domains of SP55

| No. | Inner Boundaries From | Inner Boundaries To | Outer Boundaries From | Outer Boundaries To | Segment Sequence | P:I odds* |
|---|---|---|---|---|---|---|
| 1 | 232 | 248 | 226 | 252 | FFGIVGIIWFILWICLV (232-248 of SEQ ID No. 4) | 2.589323E−05 |
| 2 | 369 | 385 | 365 | 389 | LIGMIGPAIFLVAAGFI (369-385 of SEQ ID No. 4) | 1.007311E−03 |
| 3 | 458 | 474 | 456 | 479 | TVFCIAAAINVFGAIFF (458-474 of SEQ ID No. 4) | 2.482542E−03 |
| 4 | 137 | 153 | 135 | 157 | LLLGFGIFATAIFTLFT (137-153 of SEQ ID No. 4) | 7.564906E−03 |
| 5 | 42 | 58 | 42 | 58 | LAFLSFFGFFVLYSLRV (42-58 of SEQ ID No. 4) | 8.236557E−02 |
| 6 | 328 | 344 | 328 | 345 | GFLSAVPYLGCWLCMIL (328-344 of SEQ ID No. 4) | .1925022 |
| 7 | 390 | 406 | 390 | 407 | SLAVAFLTISTTLGGFC (390-406 of SEQ ID No. 4) | .8064944 |

*Relates hydrophobicity of integral sequence to the hydrophobicity of the peripheral sequence. An integral sequence with a higher hydrophobicity number is more likely to be part of a transmembrane domain.

A computerized alignment of the amino acid sequences of GBS toxin receptor in various organisms provides further guidance in preparing preferred fragments. See, for example, Table 4 which compares the amino acid sequence of residues 42 to 536 of a human GBS toxin receptor (HP59) (residues 42 to 536 of SEQ ID NO: 8) and a sheep GBS toxin receptor (SP55).

TABLE 4

Alignment of Human and Sheep GBS Toxin Receptor Amino Acid Sequences

```
SP55   MKSPVSDLAPSDGEEGSDRTPLLQRAPRAEPAPVCCSARYNLAFLSFFGF   50
       | |||  |||   ||||   ||||||   |||||  ||||||||||||||   ||||
HP55   MRSPVRDLARNDGEESTDRTPLLPGAPRAEAAPVCCSARYNLAILAFFGF   50

SP55   FVLYSLRVNLSVALVDMVDSNTTAKDNRTSYECAEHSAPIKVLHNQTGKK   100
       |  |  |||||||||||||||||||||  |||||  |   ||||||||||  |||||||
HP55   FIVYALRVNLSVALVDMVDSNTTLEDNRTSKACPEHSAPIKVHHNQTGKK   100

SP55   YRWDAETQGWILGSFFYGYIITQIPGGYVASRSGGKLLLGFGIFATAIFT   150
       |  ||||||||||||||||||||||||||||||||  |||  ||||||  || |
HP55   YQWDAETQGWILGSFFYGYIITQIPGGYVASKIGGKMLLGFGILGTAVLT   150

SP55   LFTPLAADFGVGALVALRALEGLGEGVTYPAMHAMWSSWAPPLERSKLLS   200
       ||||  |||  |||  |  ||||||||||||||||||||||||||||||||||||||||
HP55   LFTPIAADLGVGPLIVLRALEGLGEGVTFPAMHAMWSSWAPPLERSKLLS   200

SP55   ISYAGAQLGTVVSLPLSGVICYYMNWTYVFYFFGIVGIIWFILWICLVSD   250
       ||||||||||||  ||||||  ||||||||||||||||||  || ||  ||| |||
HP55   ISYAGAQLGTVISLPLSGIICYYMNWTYVFYFFGTIGIFWFLLWIWLVSD   250

SP55   TPETHKTITPYEKEYILSSLKNQLSSQKSVPWIPMLKSLPLWAIVVAHFS   300
       ||  ||   ||||||||  ||||||||||||  |||||||||  ||||||||||||||||
HP55   TPQKHKRISHYEKEYILSSLRNQLSSQKSVPWVPILKSLPLWAIVVAHFS   300

SP55   YNWTFYTLLTLLPTYMKEVLRFNIQENGFLSAVPYLGCWLCMILSGQAAD   350
       ||||||||||||||||||||||  ||||  |||||||  |||||||  |||||||||||||
HP55   YNWTFYTLLTLLPTYMKEILRFNVQENGFLSSLPYLGSWLCMILSGQAAD   350

SP55   NLRARWNFSTLWVRRVFSLIGMIGPAIFLVAAGFIGCDYSLAVAFLTIST   400
       ||||  ||||||| |||  |||||||||||||||||||||||||||||||||||||||
HP55   NLRAKWNFSTLCVRRIFSLIGMIGPAVFLVAAGFIGCDYSLAVAFLTIST   400

SP55   TLGGFCSSGFSINHLDIAPSYAGILLGITNTFATIPGMIGPIIARSLTPE   450
       |||||||||||||||||||||||||||||||||||||||||||  || || |||
HP55   TLGGFCSSGFSINHLDIAPSYAGILLGITNTFATIPGMVGPVIAKSLTPD   450

SP55   NTIGEWQTVFCIAAAINVFGAIFFTLFAKGEVQNWAISDHQGHRN   495
       ||  ||||||||  ||||||||||||||||||||||||||||||  ||  |||
HP55   NTVGEWQTVFYIAAAINVFGAIFFTLFAKGEVQNWALNDHHGHRH   495
```

HP55 - SEQ ID NO: 2
SP55 - SEQ ID NO: 4

Thus, the foregoing examples demonstrate that those of skill in the art can recognize sequence motifs and structural conformations that may be used to define structural and functional domains in a GBS toxin receptor sequence.

Although one class of preferred embodiments are fragments having amino- and/or carboxy-termini corresponding to amino acid positions near functional domains borders, alternative fragments may be prepared. The choice of the amino- and carboxy-termini of such fragments rests with the discretion of the practitioner and will be made based on experimental considerations, such as ease of construction, stability to proteolysis, thermal stability, immunological reactivity, amino- or carboxyl-terminal residue modification, or other considerations. Polypeptide fragments usually contain at least nine amino acids and can contain any number of amino acids provided that the peptide fragment is at least about 80% identical to the corresponding fragment of SEQ ID NO: 2, SEQ ID NO: 4, or SEQ ID NO:8. The human GBS toxin receptor has 41 additional amino acids on the N-terminus compared to the sheep GBS toxin receptor (compare SEQ ID NO:4 and SEQ ID NO:8). Analogs can comprise additions or deletions of some or all of those 41 N-terminal amino acids. N-terminal and C-terminal additions useful, e.g., for purification and/or antibody recognition are also contemplated. Examples include histidine tags, a FLAG (phenylalanine, leucine, alanine, guanine) epitope, fusion partners such as glutathione S transferase, chloramphenicol acetyltransferase (CAT), luciferase, β-galactosidase, and the like. Deletions of unconserved amino acids are also contemplated, provided that the structural integrity and/or binding properties of the GBS toxin receptor are not substantially compromised.

Analogs can also comprise amino acid substitutions, preferably conservative substitutions. Also preferred are conservative and/or non-conservative substitutions in regions having less shared identity among various species. For example, a variant of a GBS toxin receptor can comprise conservative and/or non-conservative substitutions of amino acids corresponding to residues 2, 6, 10, 11, 16, 17, 24, 31, 44, 46, 52, 53, 55, 74, 75, 81, 82, 84, 93, 102, 132, 133, 137, 144, 145, 148, 149, 155, 159, 163, 165, 166, 179, 212, 219, 235, 236, 239, 242, 246, 253, 254, 257, 259, 260, 271, 283, 285, 319, 324, 332, 333, 338, 355, 362, 366, 377, 439, 442, 445, 450, 453, 461, 487, 488, 491 and 495 of SEQ ID NO:4. Preferably the substitution is an amino acid present in the corresponding position of SEQ ID NO:4 or SEQ ID NO:8. For example, referring to the alignment plot in Table 4, the amino acid corresponding to position 152 of SEQ ID NO:4 can be arginine (R), glutamine (Q), or a conservative or non-conservative substitution of R or Q, and preferably is R or Q. Such regions can be identified by amino acid sequence alignment plots, such as that shown in Table 4. Preferred amino acid substitutions are those which: (1) reduce susceptibility to proteolysis, (2) reduce susceptibility to oxidation, (3) alter binding affinity for GBS toxin, and (4) confer or modify other physicochemical or functional properties of such analogs. Analogs can include various mutations of a sequence other than the naturally-occurring peptide sequence, such as, for example, single or multiple amino acid substitutions.

A conservative amino acid substitution should generally not substantially change the structural characteristics of the parent sequence (e.g., a replacement amino acid should not tend to break a helix that occurs in the parent sequence, disrupt disulfide bonds or disrupt other types of secondary structure that characterizes the parent sequence). Examples of art-recognized polypeptide secondary and tertiary structures are described in *Proteins, Structures and Molecular Principles*, (1984) Creighton (ed.), W.H. Freeman and Company, New York; *Introduction to Protein Structure*, (1991), C. Branden and J. Tooze, Garland Publishing, New York, N.Y.; and Thornton et al. (1991) *Nature* 354: 105 (which are incorporated herein by reference). A conservative substitution is a "replacement of an amino acid in a polypeptide by one with similar characteristics." (McGraw-Hill Dictionary of Scientific and Technical Terms, Fifth Edition, 1994, Sybil P. Parker, Editor in Chief). The structure and characteristics of naturally occurring amino acids has long been known in the art (Biochemistry, Second Edition, Albert L. Lehninger, 1975, pages 71-76) For example, amino acids which are similar by virtue of their hydrophobic R groups are alanine, valine, leucine, isoleucine, proline, phenylalanine, tryptophan, and methionine. Alanine, valine, leucine, and isoleucine are similar by virtue of their aliphatic R groups. Phenylalanine and tryptophan are similar by virtue of their aromatic R groups. Glycine, serine, threonine, cysteine, tyrosine, asparagine, and glutamine are similar by virtue of their uncharged polar R groups. Glycine and alanine are similar by virtue of their small size. Serine and threonine are similar by virtue of a hydroxyl in their R group. Asparagine and glutamine differ by only one methyl group. Similarly, aspartic acid and glutamic acid differ by only one methyl group, and they are similar by virtue of their acidic R groups. Lysine, arginine, and histidine are similar by virtue of their basic R groups. In addition, lysine and arginine are similar by virtue of the amino groups on the end of the aliphatic chain in their R groups. Tyrosine and phenylalanine are similar by virtue of their aromatic groups. Amino substitutions commonly made in the art include a substitution of valine for leucine or isoleucine, alanine for glycine, serine for threonine, asparagine for glutamine, aspartic acid for glutamic acid, and lysine for arginine, tyrosine for phenylalanine, and vice versa.

Typically, one skilled in the art would generally refrain from changing amino acids that are conserved among the various GBS toxin receptors, but a conservative substitution might reasonably be made. For example, Table 4 guides one skilled in the art to avoid substitutions, particularly nonconservative substitutions, for amino acids corresponding to residues 1, 3-5, 7-9, 12-15, 18-23, 26-30, 32-43, 45, 47-51, 54, 56-73, 76-80, 83, 85-92, 94-101, 103-131, 134-136, 138-143, 146-147, 150-154, 156-158, 160-162, 164, 167-178, 180-211, 213-218, 220-234, 237-238, 240-241, 243-245, 247-252, 255-256, 258, 261-270, 272-282, 284, 286-318, 320-323, 325-331, 334-337, 339-354, 356-361, 363-365, 367-376, 378-438, 440-441, 443-444, 446-449, 451-452, 454-460, 462-486, 489-490 and 492-494 of SEQ ID NO:4, which are conserved among the GBS toxin receptors shown in Table 4.

Tables 5 and 6 describe sequences within HP59 and SP55, respectively, that match predicted amidation, N-glycosylation, cAMP-phosphorylation, CK2-phosphosylation, myristylation (addition of unsaturated fatty acid molecules), and PKC-phosphosylation sites (Omega 1.1 sequence analysis program). The information contained in these tables provides guidance to one skilled in the art for designing GBS toxin receptor variants and fragments. When designing polypeptide variants, for example, one may decide to avoid substitutions in some or all of these regions. When designing polypeptide fragments other than immunogenic polypeptide fragments, for example, one may opt to include some or all of these regions.

TABLE 5

Putative Recognition Sites in HP59

| Site | Seq. ID NO: 8 Residues: | Sequence |
|---|---|---|
| AMIDATION | 23-26 | SGRR |
| AMIDATION | 138-141 | TGKK |
| ASN_GLYCOSYLATION | 100-103 | NLSV |
| ASN_GLYCOSYLATION | 112-115 | NTTL |
| ASN_GLYCOSYLATION | 118-121 | NRTS |
| ASN_GLYCOSYLATION | 136-139 | NQTG |
| ASN_GLYCOSYLATION | 266-269 | NWTY |
| ASN_GLYCOSYLATION | 343-346 | NWTF |
| ASN_GLYCOSYLATION | 398-401 | NFST |
| CAMP_PHOSPHO_SITE | 297-300 | KRIS |
| CK2_PHOSPHO_SITE | 113-116 | TTLE |
| CK2_PHOSPHO_SITE | 114-117 | TLED |
| CK2_PHOSPHO_SITE | 300-303 | SHYE |
| CK2_PHOSPHO_SITE | 493-496 | TVGE |
| MYRISTYL | 66-71 | GAPRAE |
| MYRISTYL | 167-172 | GGYVAS |
| MYRISTYL | 183-188 | GILGTA |
| MYRISTYL | 213-218 | GLGEGV |
| MYRISTYL | 246-251 | GAQLGT |
| MYRISTYL | 250-255 | GTVISL |
| MYRISTYL | 378-383 | GSWLCM |
| MYRISTYL | 427-432 | GCDYSL |
| MYRISTYL | 444-449 | GGFCSS |
| MYRISTYL | 464-469 | GILLGI |
| MYRISTYL | 468-473 | GITNTF |
| PKC_PHOSPHO_SITE | 23-25 | SGR |
| PKC_PHOSPHO_SITE | 58-60 | TDR |
| PKC_PHOSPHO_SITE | 78-80 | SAR |
| PKC_PHOSPHO_SITE | 120-122 | TSK |
| PKC_PHOSPHO_SITE | 138-140 | TGK |
| PKC_PHOSPHO_SITE | 310-312 | SLR |
| PKC_PHOSPHO_SITE | 317-320 | SQK |

TABLE 6

Putative Recognition Sites in SP55

| Site | Seq. ID NO: 4 Residues: | Sequence |
|---|---|---|
| AMIDATION | 97-100 | TGKK |
| ASN_GLYCOSYLATION | 59-62 | NLSV |
| ASN_GLYCOSYLATION | 71-74 | NTTA |
| ASN_GLYCOSYLATION | 77-80 | NRTS |
| ASN_GLYCOSYLATION | 95-98 | NQTG |
| ASN_GLYCOSYLATION | 225-228 | NWTY |
| ASN_GLYCOSYLATION | 302-305 | NWTF |
| ASN_GLYCOSYLATION | 357-360 | NFST |
| CK2_PHOSPHO_SITE | 11-14 | SDGE |
| CK2_PHOSPHO_SITE | 73-76 | TAKD |
| CK2_PHOSPHO_SITE | 79-82 | TSYE |
| CK2_PHOSPHO_SITE | 259-262 | TPYE |
| CK2_PHOSPHO_SITE | 452-455 | TIGE |
| MYRISTYL | 126-131 | GGYVAS |
| MYRISTYL | 142-147 | GIFATA |
| MYRISTYL | 162-167 | GALVAL |
| MYRISTYL | 172-177 | GLGEGV |
| MYRISTYL | 205-210 | GAQLGT |
| MYRISTYL | 209-214 | GTVVSL |
| MYRISTYL | 337-342 | GCWLCM |
| MYRISTYL | 386-391 | GCDYSL |
| MYRISTYL | 403-408 | GGFCSS |
| MYRISTYL | 423-428 | GILLGI |
| MYRISTYL | 427-432 | GITNTF |
| PKC_PHOSPHO_SITE | 17-19 | SDR |
| PKC_PHOSPHO_SITE | 37-39 | SAR |
| PKC_PHOSPHO_SITE | 55-57 | SLR |
| PKC_PHOSPHO_SITE | 73-75 | TAK |
| PKC_PHOSPHO_SITE | 97-99 | TGK |
| PKC_PHOSPHO_SITE | 254-256 | THK |
| PKC_PHOSPHO_SITE | 269-271 | SLK |
| PKC_PHOSPHO_SITE | 276-278 | SQK |

In light of the foregoing, preferred polypeptides comprise an amino acid sequence of the formula:

AA1-AAn-AAm wherein:

AA1 is absent or is M;

AAn is a contiguous chain of 0 to 100 amino acids, preferably of 0 or 41 amino acids, even more preferably of residues 2-42 of SEQ ID NO:8; and AAm is a contiguous chain of 494 amino acids comprising AA43 through AA536, wherein:

(1) each of AA43, AA47, AA51, AA52, AA57, AA58, AA65, AA66, AA72, AA85, AA87, AA93, AA94, AA96, AA115, AA116, AA122, AA123, AA125, AA134, AA143, AA173, AA174, AA178, AA185, AA186, AA189, AA190, AA196, AA200, AA204, AA206, AA207, AA220, AA253, AA260, AA276, AA277, AA280, AA283, AA287, AA294, AA295, AA298, AA300, AA301, AA312, AA324, AA326, AA360, AA365, AA373, AA374, AA379, AA396, AA403, AA407, AA418, AA480, AA483, AA486, AA491, AA494, AA502, AA528, AA529, AA532 and AA536 is an essential amino acid or a modified amino acid and preferably is an amino acid residue corresponding to:

(a) residue 43, 47, 51, 52, 57, 58, 65, 66, 72, 85, 87, 93, 94, 96, 115, 116, 122, 123, 125, 134, 143, 173, 174, 178, 185, 186, 189, 190, 196, 200, 204, 206, 207, 220, 253, 260, 276, 277, 280, 283, 287, 294, 295, 298, 300, 301, 312, 324, 326, 360, 365, 373, 374, 379, 396, 403, 407, 418, 480, 483, 486, 491, 494, 502, 528, 529, 532 and 536, respectively, of SEQ ID NO:8;

(b) residue 2, 6, 10, 11, 16, 17, 24, 25, 31, 44, 46, 52, 53, 55, 74, 75, 81, 82, 84, 93, 102, 132, 133, 137, 144, 145, 148, 149, 155, 159, 163, 165, 166, 179, 212, 219, 235, 236, 239, 242, 246, 253, 254, 257, 259, 260, 271, 283, 285, 319, 324, 332, 333, 338, 355, 362, 366, 377, 439, 442, 445, 450, 453, 461, 487, 488, 491 and 495, respectively of SEQ ID NO:4; or (c) a conservative substitution thereof;

(2) each of AA44-AA46, AA48-AA50, AA53-AA56, AA59-AA64, AA67-AA71, AA73-AA84, AA86, AA88-AA92, AA95, AA97-AA114, AA117-AA121, AA124, AA126-AA133, AA135-AA142, AA144-AA172, AA175-AA177, AA179-AA184, AA187-AA188, AA191-AA195, AA197-AA199, AA201-AA203, AA205, AA208-AA219, AA221-AA252, AA254-AA259, AA261-AA275, AA278-AA279, AA281-AA282, AA284-AA286, AA288-AA293, AA296-AA297, AA299, AA302-AA311, AA313-AA323, AA325, AA327-AA359, AA361-AA364, AA366-AA372, AA375-AA378, AA380-AA395, AA397-AA402, AA404-AA406, AA408-AA417, AA419-AA478, AA481-AA482, AA484-AA485, AA487-AA490, AA492-AA493, AA495-AA501, AA503-AA527, AA530-AA531 and AA533-AA535 is (a) residue 44-46, 48-50, 53-56, 59-64, 67-71, 73-84, 86, 88-92, 95, 97-114, 117-121, 124, 126-133, 135-142, 144-172, 175-177, 179-184, 187-188, 191-195, 197-199, 201-203, 205, 208-219, 221-252, 254-259, 261-275, 278-279, 281-282, 284-286, 288-293, 296-297, 299, 302-311, 313-323, 325, 327-359, 361-364, 366-372, 375-378, 380-395, 397-402, 404-406, 408-417, 419-478, 481-482, 484-485, 487-490, 492-493, 495-501, 503-527, 530-531 and 533-535, respectively, of SEQ ID NO:8; or (b) a conservative substitutions thereof; and (3) AA315 through AA367 are optionally absent.

Preferred polypeptides comprise the amino acid sequence of SEQ ID NO:4, SEQ ID NO:8 or an amino acid sequence which varies from that sequence only at the specific residues which are not conserved between the sheep GBS toxin receptor (SEQ ID NO:4) and the human GBS toxin receptor (SEQ ID NO:8). Of those variations, the most preferred variations are those resulting in a polypeptide encoded by SEQ ID NO:11. Even more preferred variations are those amino acids in the corresponding positions of the amino acid sequence of SEQ ID NO:4. Particularly preferred are polypeptides comprising an amino acid sequence that differs from SEQ ID NO:2, SEQ ID NO:4 or SEQ ID NO:8 at no more than about 20% of the amino acid residues, with increasing preference for no more than about 10%, 5%, 1%, with one to zero amino acid differences being most preferred.

Besides targeting specific amino acids for change, analogs of GBS toxin receptor can also be prepared by techniques involving activity selection, such as, for example, phage display, directed evolution, DNA shuffling, and homologous in procaryotes or eucaryotes of genes from different species, as described in part in U.S. Pat. Nos. 5,605,793; 5,830,721; 5,811,238; 5,837,458; 5,093,257; 5,223,409; 5,403,484; 5,571,698; and 5,837,500, which are incorporated herein by reference.

Any variant or fragment of the human and sheep GBS toxin receptors described herein can be tested for the requisite activity by determining whether the variant or fragment can bind GBS toxin.

These polypeptides provide reagents useful in drug discovery and purification and can be used in various in vitro assays, preferably when expressed on the surface of a cell, e.g., a stable transfected cell. For example, assays such as binding assays can be used to screen test compounds, including polysaccharides and other compounds, for their ability to bind the GBS toxin receptor. Assays can identify potential drug candidates that block GBS toxin binding to the GBS toxin receptor. Such drugs are useful for preventing and/or treating early onset disease in neonatal humans. Some polypeptides can be used to competitively inhibit binding GBS toxin to a GBS toxin receptor.

The polypeptides of the invention can be used to affinity purify GBS toxin, a GBS toxin chimeric compound, and other polysaccharides or compounds which can bind the GBS toxin receptor.

The polypeptides can also be used to develop a method of targeting a cytotoxic agent for delivery to a cell that expresses a GBS toxin receptor. For example, a cytotoxic agent can be coupled to a molecule that binds a GBS toxin receptor for selective delivery to the neovasculature of a growing tumor. Such a delivery system would permit a highly concentrated, localized attack on a growing tumor, while minimizing the adverse systemic side effects encountered with most chemotherapeutics. In one instance, the cytotoxic agent can be GBS toxin, which, upon binding to GBS toxin receptor, induces an inflammatory response as described in Hellerqvist et al., *Angiogenesis: Molecular Biology, Clinical Aspects*, Edited by M. E. Maragoudakis et al., Plenum Press, New York 1994, pp. 265-269. In a similar manner, selective delivery of a therapeutic agent to a cell that expresses a GBS toxin receptor could be used advantageously to treat tumors, rheumatoid arthritis or neural injury, or to facilitate wound healing.

The polypeptides of the invention can also be used to screen for and/or design a GBS toxin mimetic with improved therapeutic properties, such as, for example, improved ability to inhibit hypoxia-induced neovascularization or angiogenesis. Such mimetics are useful in the treatment and prevention of conditions resulting from hypoxia-induced neovascularization or angiogenesis, such as, for example, tumor growth, scarring during wound healing, gliosis during repair of neural injury, reperfusion injury, restenosis, rheumatoid arthritis, psoriasis, other chronic inflammatory diseases characterized by angiogenesis, etc. Therapeutic properties can be improved by enhancing biological stability, affinity for the GBS toxin receptor, complement binding activity, reducing antigenicity, etc.

The polypeptides of the invention can also be used to generate antibodies for various therapeutic and research purposes. The polypeptides of the invention can be used to immunize rabbits, mice, goats, chickens, or other animals known in the art to be amenable to such immunization. Monoclonal antibodies are generally preferred but polyclonal antibodies can also be used, provided that detection of binding of the GBS toxin receptor antibody to the GBS toxin receptor is possible. The production of non-human monoclonal antibodies, e.g., murine, is well known (see, e.g., Harlow et al., *Antibodies A Laboratory Manual*, Cold Spring Harbor Press, pp. 139-240, 1989, incorporated herein by reference). As it may be difficult to generate human monoclonal antibodies to a human receptor or binding domain polypeptide, it may be desirable to transfer antigen binding regions of non-human monoclonal antibodies, e.g. the F(ab')$_2$ or hypervariable regions or murine monoclonal antibodies, to human constant regions (Fc) or framework regions by recombinant DNA techniques to produce substantially human molecules. Such methods are generally known and are described in, e.g., U.S. Pat. Nos. 4,816,397 and 4,946,778, and EP publications 173, 494 and 239,400. Alternatively, one may isolate DNA sequences which code for a human monoclonal antibody or portions thereof that specifically bind to the receptor protein by screening a DNA library from human B cells according to the general protocol outlined in WO 90/14430, and then cloning and amplifying the sequences which encode the antibody (or binding fragment) of the desired specificity.

Usually, polypeptides used for producing antibodies are the full-length receptor or receptor fragments designed from putative extracellular domains identified by a variety of methods known in the art, including computer programs which predict secondary and tertiary structure of a polypeptide based upon its primary amino acid sequence. Another method for designing antigenic peptides utilizes computer programs that predict the high points of hydrophilicity within a particular primary amino acid sequence. For example, using the method of Happ and Woods, *Proc. Natl. Acad. Sci. USA* (1981) 78:3824-3829, via the "Antigen" program in PC/GENE, the inventors identified 3 regions of high hydrophilicity, shown below in Table 7, and used the results to design antigenic peptides to be used in the preparation of antibodies against GBS toxin receptor (see Example 4).

TABLE 7

High Points of Hydrophilicity in SP55

| No. | Ah | Sequence | |
|---|---|---|---|
| 1 | 2.05 | Glu-Glu-Gly-Ser-Asp-Arg | (14-19 of SEQ ID No. 2) |
| 2 | 1.52 | Lys-Asp-Asn-Arg-Thr-Ser | (75-80 of SEQ ID No. 2) |
| 3 | 1.33 | Arg-Ala-Pro-Arg-Ala-Glu | (25-30 of SEQ ID No. 2) |

Ah = Average hydrophilicity.

Antibodies that recognize various portions of the intact GBS toxin receptor can be used to further investigate structure and function of the receptor. The polypeptides of the invention can give rise to antibodies that recognize a variety of forms of GBS toxin receptor, including, but not limited to, intact GBS toxin receptor expressed on a cell surface, denatured GBS toxin receptor or non-denatured GBS toxin receptor, and GBS toxin receptor purified away from cellular components or GBS toxin receptor contained in a cell lysate. GBS toxin receptor antibodies can be used to study species differences as well as GBS toxin receptor expression levels in various cell types.

Antibodies that recognize a portion or all of an extracellular domain are particularly useful as a diagnostic for the monitoring of tumor growth and metastasis, for the detection or identification of a chronic inflammatory condition, such as, for example, rheumatoid arthritis or psoriasis, and for the detection of other medical conditions arising due to hypoxia-driven angiogenesis, such as, for example, restenosis. Typically, such antibodies can be employed in a variety of standard research and diagnostic techniques, including, but not limited to, western blot, immunoprecipitation, ELISA, radioimmunoassay (RIA), BIACOR®, enzyme-linked-immunoassay (EIA), immunofluorescence, fluorescence activated cell sorting (FACS), and in vivo diagnostic imaging systems such as magnetic resonance imaging (MRI), nuclear magnetic resonance (NMR), computerized axial tomography (CAT) scan, and position emission tomography (PET), etc.

In addition, antibodies that block the binding of GBS toxin to a GBS toxin receptor can be used for the treatment or prevention of early onset disease in a neonatal human. Such antibodies can directly or indirectly block the GBS toxin binding site on the GBS toxin receptor.

In one embodiment, the GBS toxin receptor protein is naturally occurring and can be isolated from a cell extract by protein purification techniques known in the art, such as, for example, ion exchange column chromatography, high performance liquid chromatography (HPLC), reversed phase HPLC, or affinity chromatography using antibodies that recognize the GBS toxin receptor.

Alternatively, the isolated proteins and polypeptides are expressed using polynucleotides encoding the polypeptide(s) of the invention in operative association with an appropriate control sequence including a promoter in an expression vector suitable for expression, preferably in a mammalian cell, and also in bacterial, insect, or yeast cells.

Usually, the GBS toxin receptor polynucleotide or a fragment thereof can be expressed in a mammalian system. Such expression will usually depend on a mammalian promoter, which is any DNA sequence capable of binding mammalian RNA polymerase and initiating the downstream (3') transcription of a coding sequence (e.g. structural gene) into mRNA. Usually, a promoter will have a transcription initiation region which is usually placed proximal to the 5' end of the coding sequence. This transcription initiation region typically includes an RNA polymerase binding site and a transcription initiation site.

Vectors suitable for replication in mammalian cells are known in the art, and can include viral replicons, or sequences that ensure integration of the sequence encoding PAK65 into the host genome. Suitable vectors can include, for example, those derived from simian virus SV40, retroviruses, bovine papilloma virus, vaccinia virus, and adenovirus.

A suitable vector, for example, is one derived from vaccinia viruses. In this case, the heterologous DNA is inserted into the vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid shuttle vectors that greatly facilitate the construction of recombinant viruses have been described (see, for example, Mackett et al. (1984); Chakrabarti et al. (1985); Moss (1987)). Expression of the heterologous polypeptide then occurs in cells or individuals which are immunized with the live recombinant vaccinia virus.

Such suitable mammalian expression vectors usually contain one or more eukaryotic transcription units that are capable of facilitating expression in mammalian cells. The transcription unit is comprised of at least a promoter element to mediate transcription of foreign DNA sequences. Suitable promoters for mammalian cells are known in the art and include viral promoters such as those from simian virus 40 (SV40) (Subramani et al., Mol Cell. Biol. 1:854-864, 1981), cytomegalovirus (CMV) (Boshart et al., Cell 41:521-530, 1985), Rous sarcoma virus (RSV), adenovirus (ADV) (Kaufman and Sharp, Mol. Cell. Biol. 2:1304-1319, 1982), and bovine papilloma virus (BPV), as well as cellular promoters, such as a mouse metallothionein-1 promoter (U.S. Pat. No. 4,579,821), a mouse VK promoter (Bergman et al., Proc. Natl. Acad. Sci. USA 81:7041-7045, 1993; Grant et al., Nuc. Acids Res. 15:5496, 1987), and a mouse VH promoter (Loh et al., Cell 33:85-93, 1983).

The optional presence of an enhancer element (enhancer), combined with the promoter elements described herein, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when they are placed upstream or downstream from the transcription initiation site, in either normal or flipped orientation, or at a distance of more than 1000 nucleotides from the promoter (Maniatis et al. (1987) Science 236:1237; Alberts et al. (1989) Molecular Biology of the Cell, 2nd ed.). Enhancer elements derived from viruses can be particularly useful, because they typically have a broader host range. Examples useful in mammalian cells include the SV40 early gene enhancer (Dijkema et al (1985) EMBO J. 4:761) and the enhancer/promoters derived from the long terminal repeat (LTR) of the Rous Sarcoma Virus (Gorman et al. (1982b) Proc. Natl. Acad. Sci. 79:6777), from human cytomegalovirus (Boshart et al. (1985) Cell 41:521) as well as the mouse μ enhancer (Gillies, Cell 33:717-728, 1983). Additionally, some enhancers are regulatable and become active only in the presence of an inducer, such as a hormone or metal ion (Sassone-Corsi and Borelli (1986) Trends Genet. 2:215; Maniatis et al. (1987) Science 236: 1237).

In addition, the transcription unit can also be comprised of a termination sequence and a polyadenylation signal which are operably linked to the GBS toxin receptor coding sequence. Polyadenylation signals include, but are not limited to, the early or late polyadenylation signals from SV40 (Kaufman and Sharp), the polyadenylation signal from the Adenovirus 5 E1B region and the human growth hormone gene terminator (DeNoto et al., Nuc. Acids Res. 9:3719-3730, 1981).

Sequences that cause amplification of the gene may also be desirable, as are sequences which encode selectable markers. Selectable markers for mammalian cells are known in the art, and include, for example, thymidine kinase, dihydrofolate reductase (together with methotrexate as a DHFR amplifier), aminoglycoside phosphotransferase, hygromycin B phosphotransferase, asparagine synthetase, adenosine deaminase, and antibiotic resistant genes such as neomycin.

A GBS toxin receptor, or fragment thereof, can be expressed on the surface of a cell, or can be expressed in soluble or secreted form. Expression on the surface of the cell can be achieved, for example, by including a secretory leader operably linked to a nucleic acid sequence encoding the desired receptor fragment and at least one transmembrane domain. The secretory leader can be that encoded by the GBS toxin receptor gene, or can be a heterologous leader sequence commonly used in the art, such as, for example, the leader sequence of Schizosaccharomyces pombe phol+acid phosphatase (Braspenning et al., Biochem Biophys Res. Commun (1998) 245:166-71), the leader sequence of human interleukin-2 (IL-2) gene (Sasada et al., Cell Struct Funct (1988) 13:129-141). Expression in soluble or secreted form can be achieved, for example, by excluding from the gene construct nucleic acid sequences encoding a transmembrane domain. In some instances, solubility and/or secretion are achieved by the use of a fusion partner, such as, for example, chloramphenicol acetyltransferase (CAT), β-galactosidase, and other genes readily expressed in the selected host cell.

The vector that encodes GBS toxin receptor can be used for transformation of a suitable mammalian host cell. Transformation can be by any known method for introducing polynucleotides into a host cell, including, for example packaging the polynucleotide in a virus and transducing a host cell with the virus or by transfection procedures known in the art, as exemplified by U.S. Pat. Nos. 4,399,216, 4,912,040, 4,740, 461, and 4,959,455 (these patents are incorporated herein by reference). The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), N1E-115 (Liles et al., J. Biol. Chem. 261:5307-5313, 1986), PC 12 human hepatocellular carcinoma cells (e.g., Hep G2), and a number of other cell lines, such as insect derived cell lines IF9 and IF21. Cell lines of particular preference are those expressing recombinant GBS toxin receptor constructs constitutively, lines which subsequently develop characteristics of a transformed cell, and lines which more preferably express GBS toxin receptor or fragments on the cell surface. Particularly preferred are ECV cells (a bladder carcinoma cell line originally referred to in the scientific literature as an endothelial cell line), human umbilical vein endothelial cells (HUVEC), bovine, sheep, and human adrenal medulla endothelial cells.

Recombinant GBS toxin receptor or fragments thereof can be produced by culturing host cells expressing the receptor or fragment in a suitable culture medium and under appropriate cell culture conditions. Culture media and conditions are variable depending on the requirements of a particular host cell line and are well known in the art. Typically, cells are cultured at 37° C. in a cell culture incubator with a fixed amount of C02, usually in the range of 5-10%.

In another embodiment, the polypeptide fragments can be synthesized chemically by techniques well known in the art, such as solid-phase peptide synthesis (Stewart et al., Solid Phase Peptide Synthesis, W.H. Freeman Co., San Francisco (1963)); Merrifield, J Am Chem Soc 85:2149-2154 (1963)). These and other methods of peptide synthesis are also exemplified by U.S. Pat. Nos. 3,862,925, 3,842,067, 3,972,859, and 4,105,602. The synthesis can use manual synthesis techniques or automatically employ, for example, an Applied BioSystems 430A or 431A Peptide Synthesizer (Foster City, Calif.) following the instructions provided in the instruction manual supplied by the manufacturer. It will be readily appreciated by those having ordinary skill in the art of peptide synthesis that the intermediates which are constructed during the course of synthesizing the present analog compounds are themselves novel and useful compounds and are thus within the scope of the invention.

In addition to polypeptides consisting only of naturally-occurring amino acids, peptidomimetics are also provided. Peptide analogs are commonly used in the pharmaceutical industry as non-peptide drugs with properties analogous to those of the template peptide. These types of non-peptide compounds are termed "peptide mimetics" or "peptidomimetics" (Fauchere, J. (1986) Adv. Drug Res. 15: 29; Veber and Freidinger (1985) TINS p. 392; and Evans et al. (1987) J. Med. Chem 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity) but have one or more peptide linkages optionally replaced by a linkage selected from the group consisting of: —CH2NH—, —CH2S—, —CH2-CH2-, —CH=CH— (cis and trans), —COCH2-, —CH(OH)CH2-, and —CH2SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Vol. 1, Issue 3, "Peptide Backbone Modifications" (general review); Morley, J. S., Trends Pharm Sci (1980) pp. 463-468 (general review); Hudson, D. et al., Int J Pept Prot Res (1979) 14:177-185 (—CH2NH—, CH2CH2-); Spatola, A. F. et al., Life Sci (1986) 38:1243-1249 (—CH2-S); Hann, M. M., J. Chem Soc Perkin Trans I(1982) 307-314 (—CH—CH—, cis and trans); Almquist, R. G. et al., J. Med Chem (1980) 23:1392-1398 (—COCH2-); Jennings-White, C. et al., Tetrahedron Lett (1982) 23:2533 (—COCH2-); Szelke, M. et al., European Appln. EP 45665 (1982) CA: 97:39405 (1982) (—CH(OH)CH2-); Holladay, M. W. et al., Tetrahedron Lett (1983) 24:4401-4404 (—C(OH)CH2-); and Hruby, V. J., Life Sci (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with GBS toxin (e.g., are not contact points in the GBS toxin binding domain of the GBS toxin receptor). Derivitization (e.g., labelling) of peptidomimetics should not substantially interfere with the desired biological or pharmacological activity of the peptidomimetic.

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) Ann. Rev. Biochem. 61: 387, incorporated herein by reference); for example, by adding internal cysteine residues capable of forming intramolecular disulfide bridges which cyclize the peptide.

The invention also provides a complex comprising a GBS toxin bound to a mammalian GBS toxin receptor or a fragment of a mammalian GBS toxin receptor. Preferably, the complex comprises a GBS toxin bound to a GBS toxin receptor polypeptide described above that can bind GBS toxin. Typically, a complex is formed by contacting a GBS toxin with such a polypeptide under conditions that permit specific binding of the GBS toxin to the polypeptide. The GBS toxin can be labeled or unlabeled. The polypeptide can be present on the surface of a cell, or immobilized in a well or on a bead, or the polypeptide can be present in solution.

Detection Methods

Yet another aspect of the invention provides methods for detecting or monitoring a variety of medical conditions characterized by pathologic and/or hypoxia-driven angiogenesis or neovascularization. Examples include, but are not limited to, early onset disease in the neonate, and the progression of cancers involving tumors.

Early onset disease can be diagnosed by detecting the presence or absence of GBS toxin in a patient. One method of detection is a competition assay that determines the effect of a suspected sample on the formation of a complex between GBS toxin and a GBS toxin receptor or fragment thereof. For example, the method comprises contacting a control GBS toxin with a GBS toxin receptor polypeptide, in the presence and absence of a sample suspected of containing GBS toxin and under conditions that permit specific binding of the GBS toxin to the polypeptide, and comparing the amount of complex formation achieved in the presence of the suspected sample to the amount of complex formation achieved in the absence of the suspected sample. Preferably, the control GBS toxin is substantially purified and of a known concentration. Preferably, the control GBS toxin further comprises a label. Suitable labels include, but are not limited to, radioisotopes, chromophores, fluorophores, biotin, avidin, and other labels used by one skilled in the art. Another method directly measures, rather than by competition with a control GBS toxin, complex formation between GBS toxin present in a suspected sample and a GBS toxin receptor polypeptide.

Pathologic vasculature can be detected in a mammalian tissue by detecting the presence or absence of GBS toxin receptor in the region of a tumor, with the presence of GBS toxin receptor being indicative of the presence of pathologic vasculature. The method can be used to monitor tumor growth or metastasis. One method of detection involves the use of molecules, e.g. antibodies, that specifically bind to a GBS toxin receptor, preferably an extracellular domain of GBS toxin receptor. Typically, the method comprises administering, to a mammalian tissue, e.g. in a mammal having a cancerous tumor, e.g., an antibody that recognizes a GBS toxin receptor, and detecting specific binding of the antibody. Typically, the antibody is a labeled antibody. Preferably, the observations are quantitative and can be visual.

During surgery, the margin of a tumor can be visualized by any of a number of imaging techniques known in the art and described above. The imaging of the tumor is effected by detecting the binding of a labeled antibody or other molecules to the GBS toxin receptor on the pathologic vasculature of a tumor. This type of surgery is also known as virtual surgery because while performing the surgery, the surgeon views the tumor indirectly on an imaging screen.

Drug Discovery

A fourth aspect of the invention provides methods, using the polypeptides of the invention, of identifying drug candidates for the treatment of medical conditions characterized by hypoxia-driven angiogenesis or neovascularization. Preferred compounds are competitive inhibitors of GBS toxin binding to a GBS toxin receptor or inhibit GBS toxin receptor activity. Particularly preferred are compounds that inhibit the first phosphorylation step in the signal transduction pathway. Compounds can be produced by a variety of random drug design methods commonly known in the art, such as, for example, combinatorial chemistry (U.S. Pat. Nos. 5,646,285; 5,639,603), peptide libraries (U.S. Pat. Nos. 5,591,646; 5,367,053; 5,747,334), phage display (U.S. Pat. No. 5,403,484; 5,223,409), SELEX® (U.S. Pat. No. 5,773,598; U.S. Pat. No. 5,763,595; 5,763,566), and combinatorial carbohydrate chemistry (Hirschmann et al., J Med Chem (1996) 39:2441-2448; Hirschmann et al., J Med Chem (1998) 41:1382-1391; Sofia M J, Mol Divers (1998) 3:75-94; U.S. Pat. No. 5,780,603; 5,756,712)

An alternative approach is rational drug design with the intent of producing a GBS toxin mimetic or a GBS toxin receptor mimetic with improved therapeutic properties using techniques such as x-ray crystallography, nuclear magnetic resonance (NMR) correlation spectra (U.S. Pat. No. 5,698,401), computer assisted molecular modeling (U.S. Pat. No. 5,579,250; 5,612,895; 5,680,331, Cooper et al., J. Comput.-Aided Mol. Design, 3:253-259 (1989); Brent et al., J. Comput.-Aided Mol. Design 2:311-310 (1988)) and other methods of rational drug design known in the art. FIG. 1 provides a broad overview of some of the main steps in some of the rational drug design methods of the present invention. For example, one approach to rational drug design involves a computer program, such as INSIGHTII (available from Bisoym Technologies, 10065 Barnes Canyon Road, San Diego, Calif.) to identify active sites in proteins by homology-based modeling. This method facilitates the modeling of a protein by using a similar protein whose structure is well known. Commercial software containing search algorithms for three dimensional database comparisons are available from vendors such as Day Light Information Systems, Inc., Irvine, Calif. 92714, and Molecular Design Limited, 2132 Faralton Drive, San Leandro, Calif. 94577.

In one embodiment, the compound can bind the GBS toxin receptor and induce an inflammatory response in a manner similar to the binding of GBS toxin to the GBS toxin receptor. Such compounds can be used, for example, as a drug to target an inflammatory response to the developing vasculature of a tumor.

In another embodiment, the compound can bind the GBS toxin receptor with or without inducing an inflammatory response, preferably without inducing an inflammatory response. In one instance, the compound can be used as a vehicle to target pathological neovasculature for treatment with a cytotoxic agent. For example, the cytotoxic agent can be chemically coupled to the compound to form a chimeric drug. Such chimeric drugs can be used in the treatment of tumors, rheumatoid arthritis, wound healing, spinal cord injury, and other conditions characterized by hypoxia-driven angiogenesis or neovascularization. In another instance, the compound can be used directly to competitively inhibit binding of GBS toxin to a GBS toxin receptor. Such compounds can be used in the treatment of early-onset disease in the neonate.

In a third embodiment, the compound can bind GBS toxin and can be used in the treatment of early-onset disease in the neonate.

The polynucleotides of the invention can be expressed in random mutagenesis systems such as phage display or the yeast two-hybrid system for the synthesis and identification of mutant peptide GBS toxin receptor polypeptides that bind GBS toxin. Alternatively, immobilized or soluble GBS toxin receptor fragments of the invention can be used to screen combinatorial peptide and combinatorial chemical libraries and non-random recombinant and synthetic peptides and other compounds (such as non-peptide molecules) for GBS toxin receptor binding. Compounds that bind GBS toxin or GBS toxin receptor can then be further characterized in a functional assay for any of the activities described above in order to identify a drug candidate for the treatment of medical conditions involving angiogenesis or neovascularization.

A compound which inhibits binding of GBS toxin to a GBS toxin receptor can be identified by combining a test compound with a mammalian GBS toxin receptor or fragment thereof capable of binding GBS toxin, under conditions that permit specific binding of GBS toxin to the GBS toxin receptor or fragment, and determining the amount of inhibition by the compound of the binding of GBS toxin to the GBS toxin receptor or fragment.

In a preferred embodiment, the GBS toxin receptor or fragment is expressed by a cell, preferably on the cell surface. The cells are contacted with labeled GBS toxin in the presence or absence of the test compound. A change in the binding of GBS toxin to the GBS toxin receptor is then determined. Alternatively, the GBS toxin is unlabeled and an antibody that recognizes GBS toxin is labeled instead. The labeled antibody is used to measure inhibition by a compound of GBS toxin binding to the GBS toxin receptor or fragment. In another embodiment, the GBS toxin receptor or fragment is not associated with a cell, but is instead coupled to a matrix, such as, for example, a well in a microtiter plate or a bead. Additional suitable solid supports include latex, polystyrene beads (Interfacial Dynamics Corp. Portland, Oreg.), magnetic particles (Advanced Magnetics, Cambridge, Mass.) and nylon balls (Hendry et al., J. Immunological Meth., 35:285-296, 1980). The receptor or fragment can be coupled to the matrix directly or indirectly through an antibody, coupled to the matrix, that binds the receptor fragment. In a third embodiment, the GBS toxin receptor or fragment is soluble and can be immunoprecipitated with an antibody that recognizes the receptor or fragment.

A preferred method for identifying a compound which binds a mammalian GBS toxin receptor comprises the steps of (1) combining a test compound with a GBS toxin receptor or fragment thereof under conditions that allow specific binding to occur, and (2) detecting a complex formed between the test compound and the GBS toxin receptor or fragment. A preferred method is a competition assay which determines the ability of the test compound to compete for binding to the GBS toxin receptor or fragment. In such an assay, GBS toxin is combined with the GBS toxin receptor or fragment in the presence or absence of the test compound. Decreased specific binding of GBS toxin in the presence versus the absence of the test compound is indicative of the ability of the test compound to bind a mammalian GBS toxin receptor. Another method comprises combining a control compound with the GBS toxin receptor or fragment under the same conditions as the test compound and comparing the amount of complex formation between the test compound or the control compound and the GBS toxin receptor or fragment thereof. Preferably, the test compound and/or the control compound are labeled. The test compound can be any of a number of classes of compounds, such as for example, small organic molecules (such as those used for and obtained by combinatorial chemistry), polysaccharides, polypeptides, RNA, antibodies, and single chain antibodies. In a preferred embodiment, the polypeptide is expressed by a cell, preferably on the surface of the cell, and preferably by a stable transfected cell. Such a system is particularly useful for testing the effectiveness of a chimeric compound comprising a cytotoxic agent. The cytotoxic activity of the compound can be determined by exposing a cell expressing the GBS toxin receptor on the cell surface to the test chimeric compound and detecting signs of cytotoxicity. One could detect such signs by a viability stain of the cell, by detecting apoptosis (for example, by a DNA ladder assay or a TUNEL™ stain, which binds to broken DNA), by measuring tritiated thymidine incorporation into the cell, and by quantitating kinase-dependent phosphorylation (e.g., using phosphoantibodies or various phosphoimaging techniques).

In another embodiment, the invention provides a method for identifying an inhibitor of GBS toxin receptor. The method comprises incubating test cells in the presence and absence of a test compound. The test cells express GBS toxin receptor or a fragment thereof having GBS toxin receptor activity (e.g., a fragment that increases the proliferation or migration of the expressing cells relative to control cells of the same cell type that do not express the fragment). The test cells are incubated under conditions in which the cells incubated in the absence of the test compound can proliferate or migrate. Control cells that do not express the GBS toxin receptor or fragment proliferate or migrate less than cells that express the GBS toxin receptor or fragment. The proliferation or migration (also referred to herein as motility) of the test cells incubated in the presence or absence of the test compound is compared. Less proliferation or migration in the presence of the test compound than in the absence of the test compound is indicative of the test compound being an inhibitor of the GBS toxin receptor. Preferably, as a control to determine whether the test compound specifically inhibits the GBS toxin receptor, the proliferation or migration of control cells in the presence and absence of the test compound is also compared. In the absence of a difference in the proliferation or migration of control cells incubated in the presence or absence of the test compound, decreased proliferation or migration in test cells exposed to the test compound relative to test cells not exposed to the test compound is indicative of specific inhibition of the GBS toxin receptor. It will be readily apparent that the control portions of the method need not be performed contemporaneously with the test portions of the method. For example, control cells can be incubated with a battery of test compounds to determine cellular effects of the test compounds prior to incubating the test cells with the test compounds. Motility or migration can be determined by detecting movement of cells on a culture dish. Proliferation can be detected in a number of ways, including, but not limited to, measuring tritiated thymidine incorporation, cell counts, apoptosis assays, and viability assays. Preferred cells include cells transfected with GBS toxin receptor, preferably endothelial cells transfected with GBS toxin receptor, even more preferably vascular endothelial cells or microvascular endothelial cells. Primary cells that express GBS toxin receptor are also preferred, for example, endothelial cells that have been passaged in cell culture, at confluence, no more than 8 or 9 times. A preferred class of test compounds includes kinase inhibitors, preferably cAMP-dependent kinase inhibitors, PKC inhibitors, and CK2 inhibitors, which can be used as a starting point for developing more specific GBS toxin receptor inhibitors. Another class of compounds includes antibodies specific for GBS toxin receptor. Particularly preferred are single chain antibodies, preferably a collection of single chain antibodies that recognize various epitopes on the GBS toxin receptor. Less preferred are divalent antibodies specific for the binding site of the GBS toxin receptor ligand because they may trigger the signal transduction cascade upon dimerization.

Another embodiment of the invention is a method of identifying an inhibitor of endothelial cell proliferation or migration, which are essential components of angiogenesis. The method basically comprises the steps described in the preceding paragraph and uses endothelial cells.

Yet another embodiment of the invention is a method of identifying a therapeutic compound for the treatment or prevention of a medical condition characterized by pathologic or hypoxia-driven angiogenesis or neovascularization. The method basically comprises the steps described above and uses cells from tissues derived from mammals afflicted with the medical condition or cells that serve as a model for afflicted tissue.

A preferred method for designing a compound which inhibits binding of a GBS toxin to a mammalian GBS toxin receptor comprises (1) simulating and selecting the most probable conformations of a GBS toxin receptor or fragment thereof, (2) designing a chemically modified analog that substantially mimics the energetically most probable three-dimensional structure of the GBS toxin receptor or fragment, (3) chemically synthesizing the analog, and (4) evaluating the bioactivity of the analog. Preferably, steps (a) and (b) are performed with the aid of a computer program.

A preferred method for designing a compound which binds to a mammalian GBS toxin receptor comprises (1) simulating and selecting the most probable conformations of a GBS toxin receptor or fragment thereof, (2) deducing most probable binding domains of the receptor or fragment, (3) designing a compound that would form the energetically most probable complexes with the receptor or fragment, (4) chemically synthesizing the compound, and (5) evaluating the bioactivity of the compound. Preferably, steps (a)-(c) are performed with the aid of a computer program.

Preferred polypeptides for use in the screening assays described above are polypeptides sharing at least about 85% identity, preferably at least about 95% identity, and most preferably greater than about 99% identity with the amino acid sequence of SEQ ID NO: 2 or SEQ ID NO: 4, or a fragment thereof having GBS toxin receptor activity. Most preferred are polypeptides having an amino acid sequence of SED ID NO: 2, 4 OR 8 or a fragment thereof having GBS toxin receptor activity.

Methods of Purification

Another aspect of the invention is a method for purifying a compound that binds a GBS toxin receptor, for example, natural ligand, other polysaccharides, or an antibody specific for the GBS toxin receptor. The method comprises providing a polypeptide comprising a mammalian GBS toxin receptor or fragment thereof that binds GBS toxin, contacting the polypeptide with a sample comprising the compound under conditions that allow specific binding of the compound to the polypeptide, and separating the bound compound from the remainder of the sample. The polypeptide can be soluble but preferably is immobilized on a substrate e.g., on a bead, membrane or on the surface of a cell, preferably a stable transfected cell.

Methods of Treatment

GBS toxin receptor polypeptides and antibodies that interfere with GBS toxin binding can be used in a method of treatment of the human or animal body. For example, such inhibitors of GBS toxin binding can be administered to a patient to treat or prevent medical conditions involving GBS toxin binding to a GBS toxin receptor, such as, for example, early onset disease in the neonate.

GBS toxin mimetics or other compounds that bind and/or inhibit GBS toxin receptor, some of which can be identified by the drug discovery assays of the invention, can be used in a method of treatment of the human or animal body or can be used for the manufacture of a medicament for the treatment or prevention of any of a number of medical conditions involving pathologic and/or hypoxia-driven angiogenesis, such as, for example, cancerous tumors, chronic inflammatory diseases, scarring during wound healing or repair of neural injury.

In a preferred embodiment, such a compound exerts its therapeutic effect by binding GBS toxin receptor and evoking an inflammatory response, as does GBS toxin. Preferably, such compounds comprise a sulfhydryl, hydroxyl, or amino group displayed so as to be available for binding complement C3.

In another preferred embodiment, the compound is an inhibitor of GBS toxin activity. Preferred inhibitors include, but are not limited to, kinase inhibitors, single chain antibodies specific for the GBS toxin receptor, and antisense polynucleotides that specifically hybridize under high stringency conditions to a GBS toxin receptor nucleic acid sequence, such as that of SEQ ID NO:1, SEQ ID NO:3 or SEQ ID NO:7.

In another preferred embodiment, the compound exerts its therapeutic effect without evoking an inflammatory response. The compound can be used to deliver a cytotoxic agent to tissue in close proximity to a cell expressing a GBS toxin receptor, such as, for example, a tumor undergoing angiogenesis. Preferably, the compound is covalently attached to a cytotoxic agent and can be associated non-covalently with a cytotoxic agent, such as, for example, on the external surface of a liposome, micelle, or other lipophilic drug encapsulating structure. Preferred cytotoxic agents include antineoplastic agents commonly known in the art, such as, for example, mechlorethamine, chlorambucil, cyclophosphamide, melphalan, ifosfamide, and other alkylating agents, methotrexate and other folate antagonists, 6-mercaptopurine and other purine antagonists, 5-fluorouracil and other pyrimidine antagonists, cytarabine, ovinblastine, vincustine, and other vincas, etoposide and other podophyllotoxins, doxorubicin, bleomycin, mitomycin, and other antibiotics, carmustine, lomustine and other nitrosureas, cisplatin, interferon, asparaginase, tamoxifen, flutamide, and taxol. Other preferred biologic agents include sense and/or antisense RNA or DNA sequences derived from specific tumor promoter or suppressor genes, such as, for example, the p53 and TGF gene families, signal transduction protein family members such as, for example, ras and myc, and growth factor receptor kinases such as, for example flt2 and flk1, Tai1, Tai2, and neuropholin, and other genes implicated in neoplastic disease and other diseases driven by pathologic angiogenesis.

In another embodiment, GBS toxin receptor polypeptide or fragment thereof can be administered to a subject as a decoy to reduce the amount of stimulation of the GBS toxin receptor present in afflicted tissues (e.g., tumor tissues), thereby reducing cellular responses leading to proliferation and migration of cells of the afflicted tissues. Preferably, the GBS toxin receptor polypeptide or fragment is administered in soluble form, even more preferably sans transmembrane domains.

Pharmaceutical Compositions

Polypeptides of the invention that comprise a domain essential for GBS toxin binding that have the desired characteristics for bioavailability, stability and other important parameters of pharmacokinetics in vivo can be used as a competitive inhibitor of GBS toxin binding for medical conditions, such as, for example, early onset disease in the neonate, in which GBS toxin binding is undesirable. Appropriate polypeptides can include fragments having an amino acid sequence corresponding to a partial or full sequence of SEQ ID NO: 2 or SEQ ID NO: 4 or analogs thereof.

Compounds determined by assays using the polypeptides of the invention to bind and/or GBS toxin receptor and/or induce an inflammatory response, and that have the desired pharmacokinetic characteristics, can be used as treatments for medical conditions in which GBS toxin binding can be therapeutic, such as, for example, medical conditions involving pathologic or hypoxia-driven angiogenesis or neovascularization.

Pharmaceutical compositions of the invention include a pharmaceutically acceptable carrier that may contain a variety of components that provide a variety of functions, including regulation of drug concentration, regulation of solubility, chemical stabilization, regulation of viscosity, absorption enhancement, regulation of pH, and the like. For example, in water soluble formulations the pharmaceutical composition preferably includes a buffer such as a phosphate buffer, or other organic acid salt, preferably at a pH of between about 7 and 8. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g. Remington's Pharmaceutical Science, latest edition (Mack Publishing Company, Easton, Pa.).

An effective amount of an active compound such as a GBS toxin receptor polypeptide, mimetic or analog, or GBS toxin mimetic or analog for particular applications depends on several factors, including the chemical nature of the polypeptide, mimetic or analog, the disorder being treated, the method of administration, and the like. Preferably, an effective amount will provide a concentration of polypeptide or mimetic of between about 0.0001 to 100 μM at the target GBS toxin receptor on a cell surface, more preferably less than 10 μM, with less than 1 μM being most preferred.

The active compound can be administered to a mammalian host in a variety of forms, i.e., they may be combined with various pharmaceutically acceptable inert carriers in the form of tablets, capsules, lozenges, troches, hard candies, powders, sprays, elixirs, syrups, injectable or eye drop solutions, and the like depending on the chosen route of administration, e.g., orally or parenterally. Parenteral administration in this respect includes administration by the following routes: intravenous, intramuscular, subcutaneous, intraocular, intrasynovial, transepithelial (including transdermal, ophthalmic, sublingual and buccal), topical (including ophthalmic, dermal, ocular, rectal, nasal inhalation via insufflation and aerosol), and rectal systemic.

The active compound may be orally administered, for example, with an inert diluent or with an assimilable edible carrier, it may be enclosed in hard or soft shell gelatin capsules, compressed into tablets, or incorporated directly with the food of the diet. For oral therapeutic administration, the active compound may be incorporated with excipient and used in the form of ingestible tablets, buccal tablets, troches, capsules, elixirs, suspensions, syrups, wafers, and the like.

Such compositions and preparations should contain at lease 0.1% of active compound. The percentage of the compositions and preparations may, of course, be varied and may conveniently be between about 2% to about 6% of the weight of the unit. The amount of active compound in such therapeutically useful compositions is such that a suitable dosage will be obtained. Preferred compositions or preparations according to the present invention are prepared so that an oral dosage unit form contains between about 1 and 1000 mg of active compound.

Tablets, troches, pills, capsules and the like may also contain the following: a binder such as polyvinylpyrrolidone, gum tragacanth, acacia, sucrose, corn starch or gelatin; an excipient such as calcium phosphate, sodium citrate and calcium carbonate; a disintegrating agent such as corn starch, potato starch, tapioca starch, certain complex silicates, alginic acid and the like; a lubricant such as sodium lauryl sulfate, talc and magnesium stearate; a sweetening agent such as sucrose, lactose or saccharin; or a flavoring agent such as peppermint, oil of wintergreen or cherry flavoring. Solid compositions of a similar type are also employed as fillers in soft and hard-filled gelatin capsules; preferred materials in this connection also include lactose or milk sugar as well as high molecular weight polyethylene glycols. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, flavoring such as cherry or orange flavor, emulsifying agents and/or suspending agents, as well as such diluents as water, ethanol, propylene glycol, glycerin and various combinations thereof. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. For purposes of parenteral administration, solutions in sesame or peanut oil or in aqueous propylene glycol can be employed, as well as sterile aqueous solutions of the corresponding water-soluble, alkali metal or alkaline-earth metal salts previously enumerated. Such aqueous solutions should be suitably buffered, if necessary, and the liquid diluent first rendered isotonic with sufficient saline or glucose. Solutions of the active compound as a free base or a pharmacologically acceptable salt can be prepared in water suitably mixed with a surfactant such as hydroxypropylcellulose. A dispersion can also be prepared in glycerol, liquid polyethylene glycols and mixtures thereof and in oils. Under ordinary conditions of storage and use, these preparations contain a preservative to prevent the growth of microorganisms. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for drop-wise administration to the eye. The compounds of this invention may be administered to a mammal alone or in combination with pharmaceutically acceptable carriers. As noted above, the relative proportions of active ingredient and carrier are determined by the solubility and chemical nature of the compound, chosen route of administration, the particular compound chosen and the physiological characteristics of the particular patient under treatment.

Kits

Yet another aspect of the invention is a kit for use in carrying out any of the above methods. A preferred embodiment is a kit comprising a GBS toxin receptor or fragment thereof. Preferably, the receptor or fragment is immobilized. A preferred kit can be used for identifying a compound that binds to GBS toxin receptor, and comprises at least one cell that expresses GBS toxin receptor.

Another embodiment is a kit for monitoring tumor growth or metastasis, comprising a reagent for detecting expression of a GBS toxin receptor. Examples of such reagents include, but are not limited to, polynucleotide probes that hybridize to a GBS toxin receptor nucleic acid sequence and compounds that bind to a GBS toxin receptor, such as, for example, an antibody that specifically recognizes GBS toxin receptor, a GBS toxin, a GBS toxin mimetic, or other compounds identified by the screening methods described above.

A third embodiment is a kit for purifying a compound that binds a GBS toxin receptor, comprising a GBS toxin receptor or fragment thereof that binds the compound. Preferred compounds include GBS toxin, GBS toxin mimetics, antibodies that specifically bind GBS toxin receptor, and other compounds identified by the screening methods described above.

Additional kit components can include, but are not limited to, additional reagents required for detection, a reference standard(s), instructions for use, and the like. Suitable reference standards include positive controls, negative controls, photographs of such controls, tabulated or graphed data of such controls, and the like. The kits may further comprise instructions for carrying out the methods described above, preferably printed instructions.

EXAMPLES

Example 1

Cloning Sheep GBS Toxin Receptor

Primary Culture of Sheep Lung Endothelial Cells

Small pieces of primary lung tissues from a 7-week old sheep are cut into small pieces in Hank's balanced salt solution (HBSS) containing 10 mM HEPES buffer (Life Technology), 1% penicillin/streptomycin and 0.1% gentamycin, and are cultured in sheep lung complete medium (Life Technology) at 37° C. After one week of the culture, clones of sheep lung endothelial cells are identified by Cobblestone morphology and harvested into 24-well tissue culture plates (Falcon) using cloning rings. When the cells are confluent, they are detached by pancreatin and transferred to a 60-mm tissue culture Petri dish or a T-25 tissue culture flask (Falcon). When they are confluent again, they are split and cultured into a few 100-mm tissue culture plates (Falcon). Each split is considered to be one passage. The same procedure is repeated until enough cells (~$10^8$) are obtained for isolation of mRNA.

Isolation of mRNA and Construction of cDNA Library

Poly(A)+ RNA is isolated from $9.2\times10^7$ sheep lung endothelial cells (passage 8 and 9) by a standard method (Pharmacia). A total of 16 μg poly$(A)^+$ RNA is acceptable amount obtained. 2.5 μg mRNA can be used to construct a cDNA library. Poly$(A)^+$ RNA is oligo(dT)-primed (with NotI restriction site) and converted into double-stranded cDNA. After adding a BstXI/EcoRI adaptor, the cDNA is unidirectionally cloned into the BstXI and NotI sites of pCDNA3.1(+) (Invitrogen). *E. coli* Top10F' (Invitrogen) is used as a host strain for amplification. $5.38\times10^6$ primary clones are an acceptable number generated. The library is amplified by plating cells onto fifty large LB agar plates containing ampicillin (100 μg/ml). The plates are scraped and aliquoted so that each aliquot represents 10 plates. DNA is purified by Qiagen Max columns (Qiagen).

Screening of cDNA Library for a Gene Encoding GBS Toxin Receptor

To screen a cDNA library for a gene encoding GBS toxin receptor gene, a unique colorimetric method is used. Five μg plasmid DNA from each pool of cDNA library is used to transfect COS7 cells. The transfected cells are cultured in four to eight 96-well tissue culture plates (Falcon) for transient expression. Each well contains about 20,000 transfected cells in DMEM medium (Life Technology). COS7 cells transfected with pCDNA3.1(+) are used as a control. After 3 days expression, the medium is carefully removed. Each well is rinsed 3 times with HPSS buffer containing $Mg^{2+}$ and $Ca^{2+}$ (wash buffer) (Life Technology).

The cells are then incubated with biotinylated toxin (50 μl per well; 1 to 1.5 μg/ml) at room temperature for 1 h. After the hour incubation, the biotinylated toxin is discarded and the wells are rinsed 3 times with the wash buffer. The cells are incubated with streptavidin-β-gal solution and each well is rinsed 3 times with the wash buffer. The cells are then incubated with PNPG (50 μl per well; 1 mg/ml in substrate buffer) at 37° C. Absorbance at 405 nm is measured by an ELISA reader at 1 and 20 h, respectively. The cells which give the highest OD are harvested. Plasmid DNA is isolated by Hirt extraction. Plasmid DNA is amplified in *E. coli* to have enough DNA for the next transfection (enrichment).

Enrichment is done 8 times by this colorimetric method. The number of the transfected cells loaded into each well is gradually decreased in the last few enrichments and untransfected cells are added to each well to give a total number of 20,000 cells per well for the cells to be confluent and to reduce background after 3 days' expression. At the last enrichment, each well has only 1 to 10 transfected cells. Cells giving the highest OD are harvested. DNA is isolated and amplified in *E. coli*.

A number of isolated clones are individually assayed by this colorimetric method. The clones which showed higher binding to CM101 are sequenced.

Sequence Analysis

DNA sequence analysis of clone pFU102, which has a 2.1 kb insert, revealed a sequence encoding a partial integral glycoprotein. N-terminal sequence was obtained by 5'RACE method (Life Technology) and a full-length gene is designated as SP55. Triple ligation yielded pCD55, which contains an entire coding region of SP55.

mRNA for the SP55 has 2844 nucleotides, encoding a protein of 495 amino acids with a predicated mass of 55 KDa, SP55. Analysis by the method of Klein et al. (Klein et al., *Biochim Biophys Acta,* 815:468-476 (1985)) classifies SP55 as an integral protein with seven transmembrane segments. SP55 has both N-glycosylation and kinase phosphorylation sites. A Swiss-Prot. search of SP55 did not reveal any high homology to known human proteins. However, SP55 has some identity (~30%) to renal sodium-dependent phosphate transporters from human, rabbit, mouse and rat. In addition, SP55 has some identity (~30 to 39%) to hypothetical proteins (HYP50 and HYP63) from *C. elegans*.

Example 2

Cloning Human GBS Toxin Receptor

The sheep GBS toxin receptor sequence shares about 37% identity with HYP50 and about 33% identity to HYP63, two hypothetical proteins from *C. elegans*. In the regions corresponding to amino acid residues 180-186 and 443-449 of SEQ ID No. 2, five amino acids within a seven amino acid stretch are absolutely conserved among the three proteins.

A first degenerate oligonucleotide, CMR3-S: 5'-CGGGATCCCGCCNGCNATGCAYRSHRTSTGG-3' (SEQ ID No. 5), was designed to include all possible codons encoding the amino acid sequences of SP55, HYP50, and HYP63 in the 180-186 region. A second degenerate oligonucleotide, CMR4-AS2: 5'-GGAATTCCDGGDGCRATKTCNARRTRRTT-3' (SEQ ID No. 6), was designed to include the complementary sequences of all possible codons encoding the amino acid sequences of SP55, HYP50, and HYP63 in the 443-449 region.

Polymerase chain reaction (PCR) was conducted using these oligonucleotides and a human embryo lung cDNA library as a template. The reaction yielded three overlapping sequences approximately 400 bp in size, which encompass part of the nucleic acid sequence of SEQ ID No. 3. These sequences were then used as probes to clone the remainder of the gene, referred to herein and HP59 (SEQ ID NO: 7).

Example 3

Preparation of Antibodies Against GBS Toxin Receptor

Rabbits are immunized with the synthetic peptides shown in Table 8. A 1 mg/ml solution of peptide plus KLH in 0.01M phosphate buffer is prepared. For the first immunization, 200 µg of peptide plus KLH (200 µl) and an equal volume of Freunds complete adjuvant, emulsified well before injection, is injected into 3-4 spots on the dorsal surface about the neck and shoulders of a rabbit. After two weeks, the second immunization (boost) is given at the same concentration of immunogen, but emulsified in Freunds incomplete adjuvant. The boost is delivered in the same region of the body. After another two weeks, blood is collected and assayed by ELISA for response against the peptide without KLH. Further boosts are given to improve antibody titer, if necessary.

TABLE 8

Immunogenic Peptides

| Peptide | Amino Acid Sequence | Size | SEQ ID Ref. |
|---|---|---|---|
| p56a | APSDGEEGSDRTPLLQRAPRAEPAPVC | 27 aa | residues 8-35 of SEQ ID NO: 4 |
| p55a | LAPSDGEEGSDRTPL | 15 aa | residues 7-22 of SEQ ID NO: 4 |
| p57a | NTTAKDNRTSYECA | 14 aa | residues 71-84 of SEQ ID NO: 4 |

Peptide p55 is a fragment of an extracellular domain of GBS toxin receptor. Peptide p57a is a fragment of an intracellular domain of GBS toxin receptor. Animals immunized with these peptides produce polyclonal antibodies Pab55 and Pab57, respectively.

Example 4

Detection of GBS Toxin Receptor Expression in Tumor Cells

This example shows that GBS toxin receptor can be detected in tumor cells. Immunohistochemistry is performed on paired human and mouse tissues of normal or tumor origin, using rabbit polyclonal antibodies Pab 55 and Pab 57.

Mouse and human tumor tissues are fixed in 10% neutral formalin. The tissues are then dehydrated, paraffin embedded and 10-20×8-micron sections are cut for immunohistochemical staining.

Immunohistochemical analysis is performed with the automated Ventana Immunohistochemical Stainer according to the manufacturer's suggested protocol (Ventana, Tucson, Ariz.). Sections are deparaffinated with xylene. The prepared sections are then treated with 1% hydrogen peroxide prepared in 30% aqueous methanol for 20 minutes at room temperature to quench endogenous peroxidase activity. The slides are then washed with PBS, blocked with 5% BSA and 5% goat serum in PBS, washed again and then incubated for 30 minutes at 37° C. with the appropriate diluted (1:100) antibody. Horseradish peroxidase-labeled goat anti-rabbit IgG is used as a secondary antibody. For visualization, the sections are incubated with DAB/$H_2O_2$. The sections are finally incubated with a copper enhancer (Ventana) for 4 minutes, washed, counterstained with hematoxylin, and mounted in toluene-minus mounting medium. Photographic documentation is performed and images are stored for later review and analysis.

The results are summarized in Table 9. The numbers refer to glass slides.

TABLE 9

Immunohistochemistry of tumor and normal tissues (diff. = differentiated)

| | Antibody | Magni-fication | Signal |
|---|---|---|---|
| Human tissues: | | | |
| 1. Ovary tumor (95-02VO16) high grade papillary carcinoma | Pab 55 | 400× | + |
| 2. Ovary tumor (95-02VO16) high grade papillary carcinoma | Pab 55 | 400× | + |
| 3. Normal ovary (96-08ZO08) control tissue | Pab 55 | 400× | − |
| 4. Ovary tumor (95-02VO16) high grade papillary carcinoma | Pab 57 | 400× | + |
| 5. Ovary tumor (95-02VO16) high grade papillary carcinoma | Pab 57 | 400× | + |
| 6. Ovary tumor (95-02VO16) high grade papillary carcinoma | Pab 57 | 400× | + |
| 7. Normal ovary 96-08ZO08) control | Pab 57 | 400× | − |
| 8. Colon cancer 95-14664) poorly diff. Adenocarcinoma | Pab 55 | 400× | + |
| 9. Normal colon 9708VO08) control | Pab 55 | 400× | − |
| 10. Colon cancer 95-14664) poorly diff. Adenocarcinoma | Pab 57 | 400× | + |
| 11. Colon cancer 95-14664) poorly diff. Adenocarcinoma | Pab 57 | 400× | + |
| 12. Normal colon 9708VO08) control | Pab 57 | 400× | − |
| 13. Female breast cancer (97-IOV03a) Invasive mammary carcinoma | Pab 55 | 400× | + |
| 14. Male breast cancer (no code) mammary carcinoma | Pab 55 | 400× | + |
| 15. Normal female breast 97-12VO20-3) control | Pab 55 | 400× | − |
| 16. Female breast cancer 97-IOV03a) Invasive mammary carcinoma | Pab 57 | 400× | + |
| 17. Male breast cancer (no code) mammary carcinoma | Pab 57 | 400× | + |
| 18. Normal female breast (97-12VO20-3) control | Pab 57 | 400× | − |
| 19. Lung cancer (97-1OV022-5) poorly diff. NOJ-small cell carcinoma | Pab 55 | 400× | + |
| 20. Normal lung (98-01VO11) control | Pab 55 | | − |
| 21. Lung cancer (97-10VO22-5) poorly diff. NOJ-small cell carcinoma | Pab 57 | 400× | + |

TABLE 9-continued

Immunohistochemistry of tumor and normal tissues
(diff. = differentiated)

| | Antibody | Magnification | Signal |
|---|---|---|---|
| 22. Lung cancer (97-10VO22-5) poorly diff. NOJ-small cell carcinoma | Pab 57 | 400× | + |
| 23. Normal lung (98-01VO11) control | Pab 57 | | − |
| Mouse Tissues: | | | |
| 24. Madison Lung Tumor (MLT) untreated with CM 101 | Pab 55 | | + |
| 25. MLT untreated with CM 101 | Pab 55 | | + |
| 26. Normal mouse lung | Pab 55 | | − |
| 27. MLT untreated with CM 101 | Pab 57 | | + |
| 28. Normal mouse lung | Pab 57 | | − |

Figure 2A:
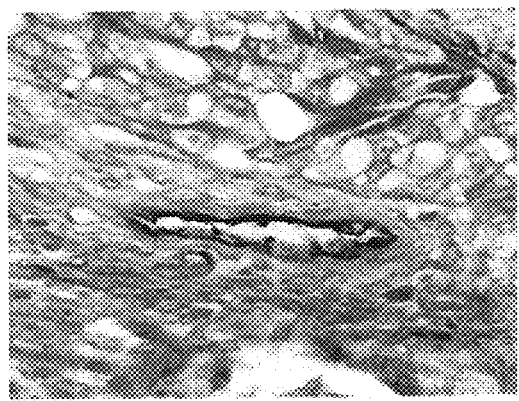
FIGS. 2A and 2B depict the results of immunohistochemical analysis of GBS toxin receptor expression in cancerous and normal human ovary tissue, respectively, using antibody Pab55 as described in Example 4.
Figure 2B:
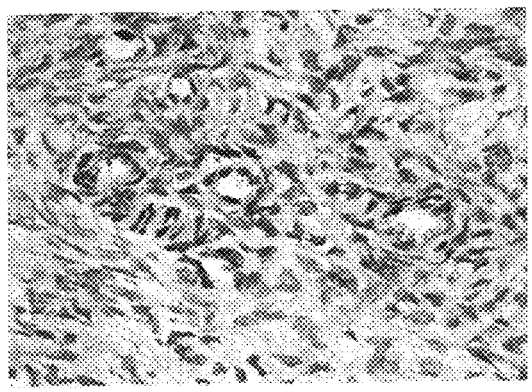

The Pab 55 antibody stains the cells lining a blood vessel in a human ovary cancer tissue section, but such staining is not apparent in cells of normal human ovary tissue (see FIGS. 2A and 2B, respectively). Similar results are obtained with the Pab 57 antibody (see FIGS. 3A and 3B). As shown in the above table and in FIGS. 2A-3B, antibodies raised to GBS toxin receptor fragments specifically bound to tumor tissues but not normal tissues, suggesting that GBS toxin receptor is expressed in tumor cells but not normal cells.

Example 5

Detection of GBS Toxin Receptor Expression in Mice Afflicted with Rheumatoid Arthritis This example shows that GBS toxin receptor can be detected in cells from a mammalian model for rheumatoid arthritis (RA). Mice with collagen-induced arthritis were treated with CM101 or carrier. CM101 reversed the inflammatory damage and inhibited pannus formation. Mouse #8 and #15, which were treated with CM101, and two control mice (not treated with CM101) were sacrificed for immunohistochemistry.

TABLE 10

Immunohistochemistry of Rheumatoid Arthritic Mice

| 29. No CM 101 | Pab 55 | + |
|---|---|---|
| 30. MOUSE 8 - 5' (vessel) | Pab 55 | + |
| 31. No CM 101 | Pab 57 | + |
| 32. MOUSE 15 - 5' (vessel) | Pab 57 | + |
| 33. MOUSE 8 - 5' (between joint) | Pab 57 | + |
| 34. MOUSE 15 - 5' | Pab 57 | + |
| 35. No CM 101 (marrow) | Pab 57 | + |
| 36. MOUSE 15 - 5' (marrow) | Pab 57 | + |

As shown above Pab55 and Pab57 specifically bound to pathologic neovasculature in the pannus, suggesting that GBS toxin receptor is expressed in mice afflicted with rheumatoid arthritis. No binding of CM101 was observed in the normal neovasculature in the growth plate of the joints of the arthritic mice.

Example 6

Targeted Delivery of a Chimeric Compound to Tissues Expressing GBS Toxin Receptor This example shows the targeted delivery of a chimeric compound to tissues expressing GBS toxin. The chimeric compound is a CM101-biotin conjugate. Mice with Madison Lung Tumors (MLT) are infused intravenously (i.v.) with biotinylated CM 101.

CM101 has been reacted with hydrazinylated biotin to form the biotin hydrazone at the reducing end of the polysaccharide CM101. Briefly, 25 micrograms of lyophilized CM101 is dissolved in 250 μl labeling buffer at 100 mM sodium acetate, 0.02% sodium azide. Aqueous meta-periodate (125 μl of 30 mM) is added and the oxidation is allowed to proceed in the dark for 30 minutes at room temperature. The reaction is terminated by adding 80 mM $Na_2SO_3$ to the solution. The resultant aldehydes are reacted with 125 μl of 5 mM NHS-LC-Biotin (MW 556.58) for a 1 hour incubation at room temperature to form biotinylated CM101. Excess biotin is removed by dialysis against 1 liter of PBS at 4° C. four times. The product is purified by gel filtration on an Ultrahydrogel 1000 HPLC, lyophilized and stored at −70° C. until use.

Tissues are recovered 5 min post infusion with CM101 and subjected to immunohistochemistry. Tumor and normal mouse tissue sections are analyzed for CM 101 binding by both mouse anti-CM101 mAb (7A3), followed by secondary mAb-HRP conjugate (referred to in FIG. 4B as MLT CM101-Biot.5'+McAb), or with avidin (which specifically binds biotin) conjugated with HRP (referred to in FIG. 4A as MLT CM101-Biot.5'+Strep.HRP).

Figure 4C:
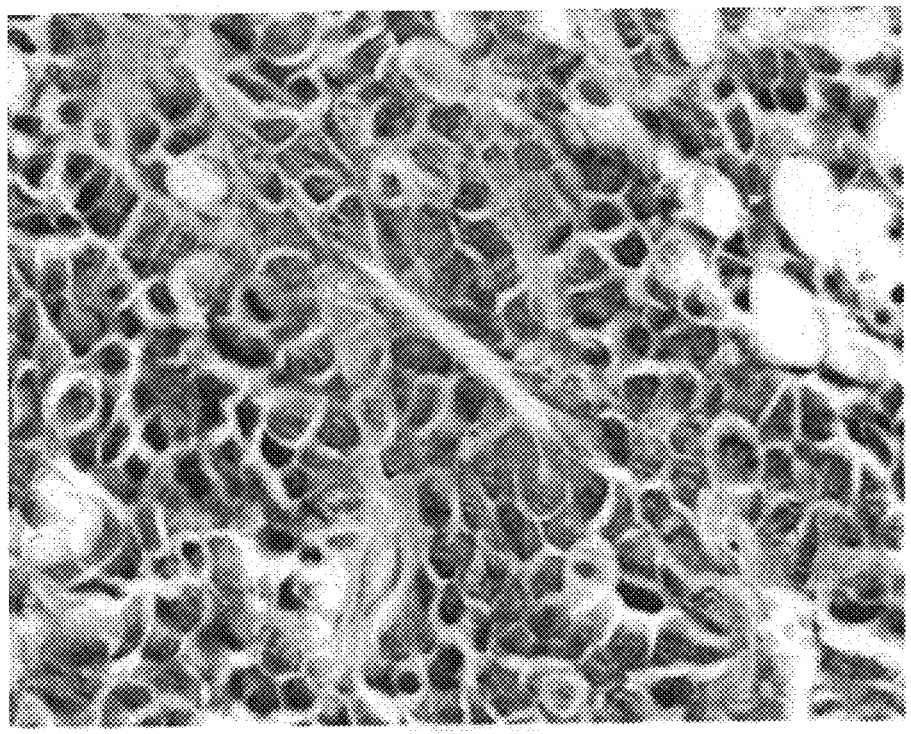

FIGS. 4A-4C depict different sections taken from the same tumor and include a longitudinal view of the same blood vessel approximately in the center of the figures. The dark staining in FIG. 4A shows the localization of the biotin component in the cells lining the blood vessel. Similarly, FIG. 4B depicts the localization of the CM101 component in the cells lining the blood vessel. FIG. 4C is a negative control that was not exposed to CM101. The analysis clearly shows that 7A3 and avidin bind to the same blood vessels in tumor tissue. Thus, biotin has been delivered to the blood vessel of the tumor tissue by virtue of its physical association with a compound (CM101) that binds the GBS toxin receptor.

These studies show that chimeric compounds can be delivered to tissues undergoing pathologic and/or hypoxia-driven angiogenesis or neovascularization. As part of a chimeric compound, cytotoxic molecules can be directed to such tissues, e.g., tumor tissue. The cytotoxic molecule can be coupled directly to a molecule that binds GBS toxin receptor, e.g., GBS toxin. Alternatively, the molecule that binds GBS toxin receptor can be coupled to biotin and the cytotoxic molecule can be coupled to avidin.

Example 7

Enhanced Sensitivity to GBS-Toxin-Dependent Cytotoxicity of Cells Expressing GBS Toxin Receptor This example shows the enhanced sensitivity to GBS-toxin-dependent cytotoxicity of cells transfected with the GBS toxin receptor, relative to control cells. Without being bound to a particular theory, the inventors believe that complement binds GBS toxin bound to the GBS toxin receptor on a cell, thereby targeting the cell for killing by white blood cells (WBC).

Human bladder carcinoma cells (ECV cells), are stable transfected with the human GBS toxin receptor gene. The resultant cell line is ECV711. Cells stable transfected with vector alone as referred to as V23. ECV 711 and V23 are seeded in 96-well plates at 5,000 cells/well.

White blood cells are collected from healthy human donors as follows. Blood is collected by standard phlebotomy procedures into heparinized tubes (30 U/ml) and centrifuged at 2000 rpm for 20 min. The interface is carefully transferred to a new tube and washed twice by centrifugation with medium (RPMI-1640). Cells are resuspended in RPMI-1640 supplemented with 5% fetal bovine serum (FBS) and Interferon-gamma (IFN) at 100 U/ml, and incubated overnight in a 37° C., 5% $CO_2$ incubator. The cells are then resuspended in fresh medium with 5% FBS.

5,000 cells of the WBC preparation are added to each well containing the transfected cells. CM101 is added to a final concentration of 1 µg/ml to the wells together with human serum from matching human donors. The cells are incubated 6 hours at 37° C.

Cytotoxicity is assayed by measuring lactate dehydrogenase (LDH) using the Promega's CytoTox 96 Non-Radioactive Assay kit (Nachlas et al. (1960) *Anal. Biochem* 1, 317; Korzeniewski et al. (1983) *J. Immunol. Methods* 64, 313; Decker et al. *J. Immunol. Methods* 115, 61; Brander et al. (1993) *Eur. J. Immunology* 23, 3217; Behl et al. (1994) *Cell* 77, 817; Lappalainen et al. (1994) *Pharm. Research* 11, 1127; Allen et al. (1994) *Promega Notes* 45, 7; Sinensky et al. (1995) *Toxicol. Letters* 75, 02; Moravec (1994) *Promega Notes* 45, 11). Percent cytotoxicity is calculated as recommended by the manufacturer's instructions. The results are shown in Table 11.

TABLE 11

| Cytotoxicity | ECV 711 | V 23 |
| --- | --- | --- |
| WBC, IFN, C3, −CM101 | 29.1% | 27.5% |
| WBC, IFN, C3, +CM101 | 40.45% | 22.46% |

There is an increase in cytotoxicity of 39% when the ECV 711 cells are incubated with CM101, WBC and human serum (source of C3) compared to cells incubated without CM101. Control cells transfected with vector alone, V23, do not show a CM101 dependent increase in cytotoxicity.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated antibody or a fragment thereof, wherein the antibody or the fragment thereof recognizes a mammalian GBS toxin receptor and wherein the GBS toxin receptor has at least about 86% identity to SEQ ID NO:8.

2. The isolated antibody or the fragment thereof of claim 1, wherein the mammalian GBS toxin receptor is expressed on a surface of a cell.

3. The isolated antibody or the fragment thereof of claim 1, wherein the isolated antibody is a monoclonal antibody or a polyclonal antibody.

4. The isolated antibody or the fragment thereof of claim 1, wherein the isolated antibody or the fragment thereof is generated by a method comprising immunizing an animal with the mammalian GBS toxin receptor or an immunogenic polypeptide fragment thereof having at least six amino acids.

5. The isolated antibody or the fragment thereof of claim 1, wherein the isolated antibody is a rabbit antibody or a mouse antibody.

6. The isolated antibody or the fragment thereof of claim 1, wherein the isolated antibody recognizes an extracellular domain of the GBS toxin receptor.

7. A composition for detection of a GBS toxin receptor comprising an isolated antibody or a fragment thereof that binds the GBS toxin receptor, wherein the GBS toxin receptor has at least about 86% identity to SEQ ID NO: 8.

8. A composition for detection of a GBS toxin receptor in a cell or a tissue, comprising an isolated antibody or a fragment thereof that binds the GBS toxin receptor, wherein the GBS toxin receptor has at least about 86% identity to SEQ ID NO: 8.

9. An isolated antibody or a fragment thereof, wherein the antibody or the fragment thereof binds a mammalian GBS toxin receptor and inhibits the binding of a GBS toxin to the mammalian GBS toxin receptor, wherein the GBS toxin receptor has at least about 86% identity to SEQ ID NO: 8.

10. An isolated composition comprising an antibody or a fragment thereof, wherein the antibody or the fragment thereof recognizes a mammalian GBS toxin receptor, and wherein the GBS toxin receptor has at least about 86% identity to SEQ ID NO:8.

* * * * *

SEQUENCE LISTING

```
<160> NUMBER OF SEQ ID NOS: 12

<210> SEQ ID NO 1
<211> LENGTH: 2602
<212> TYPE: DNA
<213> ORGANISM: Homo sapiens
<220> FEATURE:
<221> NAME/KEY: CDS
<222> LOCATION: (58)..(1542)

<400> SEQUENCE: 1
tcgggccggc gctcccttct ctgccaggtg gcgagtacac ctgctcacgt aggcgtc          57 atg agg tct ccg gtt cga gac ctg gcc cgg aac gat ggc gag gag agc       105
Met Arg Ser Pro Val Arg Asp Leu Ala Arg Asn Asp Gly Glu Glu Ser
  1               5                  10                  15 acg gac cgc acg cct ctt cta ccg ggc gcc cca cgg gcc gaa gcc gct       153
Thr Asp Arg Thr Pro Leu Leu Pro Gly Ala Pro Arg Ala Glu Ala Ala
             20                  25                  30 cca gtg tgc tgc tct gct cgt tac aac tta gca att ttg gcc ttt ttt       201
Pro Val Cys Cys Ser Ala Arg Tyr Asn Leu Ala Ile Leu Ala Phe Phe
         35                  40                  45 ggt ttc ttc att gtg tat gca tta cgt gtg aat ctg agt gtt gcg tta       249
Gly Phe Phe Ile Val Tyr Ala Leu Arg Val Asn Leu Ser Val Ala Leu
     50                  55                  60 gtg gat atg gta gat tca aat aca act tta gaa gat aat aga act tcc       297
Val Asp Met Val Asp Ser Asn Thr Thr Leu Glu Asp Asn Arg Thr Ser
 65                  70                  75                  80 aag gcg tgt cca gag cat tct gct ccc ata aaa gtt cat cat aat caa       345
Lys Ala Cys Pro Glu His Ser Ala Pro Ile Lys Val His His Asn Gln
                 85                  90                  95 acg ggt aag aag tac caa tgg gat gca gaa act caa gga tgg att ctc       393
Thr Gly Lys Lys Tyr Gln Trp Asp Ala Glu Thr Gln Gly Trp Ile Leu
            100                 105                 110 ggt tcc ttt ttt tat ggc tac atc atc aca cag att cct gga gga tat       441
Gly Ser Phe Phe Tyr Gly Tyr Ile Ile Thr Gln Ile Pro Gly Gly Tyr
```

```
                    115                 120                 125
gtt gcc agc aaa ata ggg ggg aaa atg ctg cta gga ttt ggg atc ctt    489
Val Ala Ser Lys Ile Gly Gly Lys Met Leu Leu Gly Phe Gly Ile Leu
    130                 135                 140 ggc act gct gtc ctc acc ctg ttc act ccc att gct gca gat tta gga    537
Gly Thr Ala Val Leu Thr Leu Phe Thr Pro Ile Ala Ala Asp Leu Gly
145                 150                 155                 160 gtt gga cca ctc att gta ctc aga gca cta gaa gga cta gga gag ggt    585
Val Gly Pro Leu Ile Val Leu Arg Ala Leu Glu Gly Leu Gly Glu Gly
                165                 170                 175 gtt aca ttt cca gcc atg cat gcc atg tgg tct tct tgg gct ccc cct    633
Val Thr Phe Pro Ala Met His Ala Met Trp Ser Ser Trp Ala Pro Pro
        180                 185                 190 ctt gaa aga agc aaa ctt ctt agc att tcg tat gca gga gca cag ctt    681
Leu Glu Arg Ser Lys Leu Leu Ser Ile Ser Tyr Ala Gly Ala Gln Leu
                195                 200                 205 ggg aca gta att tct ctt cct ctt tct gga ata att tgc tac tat atg    729
Gly Thr Val Ile Ser Leu Pro Leu Ser Gly Ile Ile Cys Tyr Tyr Met
    210                 215                 220 aat tgg act tat gtc ttc tac ttt ttt ggt act att gga ata ttt tgg    777
Asn Trp Thr Tyr Val Phe Tyr Phe Phe Gly Thr Ile Gly Ile Phe Trp
225                 230                 235                 240 ttt ctt ttg tgg atc tgg tta gtt agt gac aca cca caa aaa cac aag    825
Phe Leu Leu Trp Ile Trp Leu Val Ser Asp Thr Pro Gln Lys His Lys
                245                 250                 255 aga att tcc cat tat gaa aag gaa tac att ctt tca tca tta aga aat    873
Arg Ile Ser His Tyr Glu Lys Glu Tyr Ile Leu Ser Ser Leu Arg Asn
        260                 265                 270 cag ctt tct tca cag aag tca gtg ccg tgg gta ccc att tta aaa tcc    921
Gln Leu Ser Ser Gln Lys Ser Val Pro Trp Val Pro Ile Leu Lys Ser
                275                 280                 285 ctg cca ctt tgg gct atc gta gtt gca cac ttt tct tac aac tgg act    969
Leu Pro Leu Trp Ala Ile Val Val Ala His Phe Ser Tyr Asn Trp Thr
    290                 295                 300 ttt tat act tta ttg aca tta ttg cct act tat atg aag gag atc cta   1017
Phe Tyr Thr Leu Leu Thr Leu Leu Pro Thr Tyr Met Lys Glu Ile Leu
305                 310                 315                 320 agg ttc aat gtt caa gag aat ggg ttt tta tct tca ttg cct tat tta   1065
Arg Phe Asn Val Gln Glu Asn Gly Phe Leu Ser Ser Leu Pro Tyr Leu
                325                 330                 335 ggc tct tgg tta tgt atg atc ctg tct ggt caa gct gct gac aat tta   1113
Gly Ser Trp Leu Cys Met Ile Leu Ser Gly Gln Ala Ala Asp Asn Leu
        340                 345                 350 agg gca aaa tgg aat ttt tca act tta tgt gtt cgc aga att ttt agc   1161
Arg Ala Lys Trp Asn Phe Ser Thr Leu Cys Val Arg Arg Ile Phe Ser
            355                 360                 365 ctt ata gga atg att gga cct gca gta ttc ctg gta gct gct ggc ttc   1209
Leu Ile Gly Met Ile Gly Pro Ala Val Phe Leu Val Ala Ala Gly Phe
    370                 375                 380 att ggc tgt gat tat tct ttg gcc gtt gct ttc cta act ata tca aca   1257
Ile Gly Cys Asp Tyr Ser Leu Ala Val Ala Phe Leu Thr Ile Ser Thr
385                 390                 395                 400 aca ctg gga ggc ttt tgc tct tct gga ttt agc atc aac cat ctg gat   1305
Thr Leu Gly Gly Phe Cys Ser Ser Gly Phe Ser Ile Asn His Leu Asp
                405                 410                 415 att gct cct tcg tat gct ggt atc ctc ctg ggc atc aca aat aca ttt   1353
Ile Ala Pro Ser Tyr Ala Gly Ile Leu Leu Gly Ile Thr Asn Thr Phe
        420                 425                 430 gcc act att cca gga atg gtt ggg ccc gtc att gct aaa agt ctg acc   1401
```

```
Ala Thr Ile Pro Gly Met Val Gly Pro Val Ile Ala Lys Ser Leu Thr
        435                 440                 445 cct gat aac act gtt gga gaa tgg caa acc gtg ttc tat att gct gct    1449
Pro Asp Asn Thr Val Gly Glu Trp Gln Thr Val Phe Tyr Ile Ala Ala
450                 455                 460 gct att aat gtt ttt ggt gcc att ttc ttt aca cta ttc gcc aaa ggt    1497
Ala Ile Asn Val Phe Gly Ala Ile Phe Phe Thr Leu Phe Ala Lys Gly
465                 470                 475                 480 gaa gta caa aac tgg gct ctc aat gat cac cat gga cac aga cac        1542
Glu Val Gln Asn Trp Ala Leu Asn Asp His His Gly His Arg His
                485                 490                 495 tgaaggaacc aataaataat cctgcctcta ttaatgtatt tttatttatc atgtaacctc  1602
aaagtgcctt ctgtattgtg taagcattct atgtctttt ttaattgtac ttgtattaga   1662
tttttaaggc ctataatcat gaaatatcac tagttgccag aataataaaa tgaactgtgt  1722
ttaattatga ataatatgta agctaggact tctactttag gttcacatac ctgcctgcta  1782
gtcgggcaac atgaagtagg acagttctgt tgattttta gggccatact aaagggaatg   1842
agctgaaaca gacctcctga tacctttgct taattaaact agatgataat tctcaggtac  1902
tgataaacac ctgttgttgt tcactttcct cataaaaatt gtcagctctc tctgacactt  1962
agacctcaaa ctttagcatc tctgtggagc tgccatccac tgtataattt cgcctggcaa  2022
ctggactgag gggagtgtgc ccaggcagct gccaagcact ccctccctgg cttcagggtc  2082
agagtgccca gcgtttatca gaggcagcat ccaagcccag agccagtgtc gactcttcgg  2142
ctggtgcctt tcctctgagg ggctatcaat gtgtagataa agccctgagt aggcaagagc  2202
agtgagatcc actgctatgg tcttgataca tcctcaaact ttcccttccc agcacagagg  2262
aatattggct ggcatgcaac ctgcaaaaga aaaatgcgaa gcggccgggc acggtggctc  2322
atgcctgtaa tcccagcact ttgggggggct gaggtgggcg aatcatgaga tcaggagttc  2382
gagaccagcc tggccagcat ggtgaaaccc catctctact aaaaatacaa aaaattagct  2442
gggcgtggtg acgggcgcct gtaatcccag atactcagga ggctgaggta ggagaatcac  2502
ttgaacctgg gaggtggaag ttgcagtgaa ccaagatcac gccactgcac tccagcctgg  2562
gcgatggagc gagactccaa ctcaaaaaaa aaaaaaaaa                          2602

<210> SEQ ID NO 2
<211> LENGTH: 495
<212> TYPE: PRT
<213> ORGANISM: Homo sapiens

<400> SEQUENCE: 2

Met Arg Ser Pro Val Arg Asp Leu Ala Arg Asn Asp Gly Glu Glu Ser
1               5                   10                  15

Thr Asp Arg Thr Pro Leu Leu Pro Gly Ala Pro Arg Ala Glu Ala Ala
            20                  25                  30

Pro Val Cys Cys Ser Ala Arg Tyr Asn Leu Ala Ile Leu Ala Phe Phe
        35                  40                  45

Gly Phe Phe Ile Val Tyr Ala Leu Arg Val Asn Leu Ser Val Ala Leu
    50                  55                  60

Val Asp Met Val Asp Ser Asn Thr Thr Leu Glu Asp Asn Arg Thr Ser
65                  70                  75                  80

Lys Ala Cys Pro Glu His Ser Ala Pro Ile Lys Val His His Asn Gln
                85                  90                  95

Thr Gly Lys Lys Tyr Gln Trp Asp Ala Glu Thr Gln Gly Trp Ile Leu
            100                 105                 110
```

```
Gly Ser Phe Phe Tyr Gly Tyr Ile Ile Thr Gln Ile Pro Gly Gly Tyr
            115                 120                 125

Val Ala Ser Lys Ile Gly Gly Lys Met Leu Leu Gly Phe Gly Ile Leu
130                 135                 140

Gly Thr Ala Val Leu Thr Leu Phe Thr Pro Ile Ala Ala Asp Leu Gly
145                 150                 155                 160

Val Gly Pro Leu Ile Val Leu Arg Ala Leu Glu Gly Leu Gly Glu Gly
                165                 170                 175

Val Thr Phe Pro Ala Met His Ala Met Trp Ser Ser Trp Ala Pro Pro
                180                 185                 190

Leu Glu Arg Ser Lys Leu Leu Ser Ile Ser Tyr Ala Gly Ala Gln Leu
            195                 200                 205

Gly Thr Val Ile Ser Leu Pro Leu Ser Gly Ile Ile Cys Tyr Tyr Met
            210                 215                 220

Asn Trp Thr Tyr Val Phe Tyr Phe Phe Gly Thr Ile Gly Ile Phe Trp
225                 230                 235                 240

Phe Leu Leu Trp Ile Trp Leu Val Ser Asp Thr Pro Gln Lys His Lys
                245                 250                 255

Arg Ile Ser His Tyr Glu Lys Glu Tyr Ile Leu Ser Ser Leu Arg Asn
                260                 265                 270

Gln Leu Ser Ser Gln Lys Ser Val Pro Trp Val Pro Ile Leu Lys Ser
            275                 280                 285

Leu Pro Leu Trp Ala Ile Val Val Ala His Phe Ser Tyr Asn Trp Thr
            290                 295                 300

Phe Tyr Thr Leu Leu Thr Leu Pro Thr Tyr Met Lys Glu Ile Leu
305                 310                 315                 320

Arg Phe Asn Val Gln Glu Asn Gly Phe Leu Ser Ser Leu Pro Tyr Leu
                325                 330                 335

Gly Ser Trp Leu Cys Met Ile Leu Ser Gly Gln Ala Ala Asp Asn Leu
            340                 345                 350

Arg Ala Lys Trp Asn Phe Ser Thr Leu Cys Val Arg Arg Ile Phe Ser
            355                 360                 365

Leu Ile Gly Met Ile Gly Pro Ala Val Phe Leu Val Ala Ala Gly Phe
370                 375                 380

Ile Gly Cys Asp Tyr Ser Leu Ala Val Ala Phe Leu Thr Ile Ser Thr
385                 390                 395                 400

Thr Leu Gly Gly Phe Cys Ser Ser Gly Phe Ser Ile Asn His Leu Asp
                405                 410                 415

Ile Ala Pro Ser Tyr Ala Gly Ile Leu Leu Gly Ile Thr Asn Thr Phe
                420                 425                 430

Ala Thr Ile Pro Gly Met Val Gly Pro Val Ile Ala Lys Ser Leu Thr
            435                 440                 445

Pro Asp Asn Thr Val Gly Glu Trp Gln Thr Val Phe Tyr Ile Ala Ala
            450                 455                 460

Ala Ile Asn Val Phe Gly Ala Ile Phe Phe Thr Leu Phe Ala Lys Gly
465                 470                 475                 480

Glu Val Gln Asn Trp Ala Leu Asn Asp His Gly His Arg His
                485                 490                 495

<210> SEQ ID NO 3
<211> LENGTH: 2844
<212> TYPE: DNA
<213> ORGANISM: Ovis sp.
<220> FEATURE:
```

-continued

```
<221> NAME/KEY: CDS
<222> LOCATION: (84)..(1568)

<400> SEQUENCE: 3
cccgggggcg gggggcttcg gcggtcccgc tggagctctc ttttccgcgg agcaggtttg      60
cgccgtagct ccctgaaggc atc atg aag tcc ccg gtt tcg gac tta gcc ccg     113
                         Met Lys Ser Pro Val Ser Asp Leu Ala Pro
                           1               5                  10 agc gac ggc gag gag ggc tcg gac cgc aca ccg ctc ctg cag cgc gcc       161
Ser Asp Gly Glu Glu Gly Ser Asp Arg Thr Pro Leu Leu Gln Arg Ala
            15                  20                  25 ccg cgg gcg gaa ccc gct cca gta tgc tgc tct gct cgt tac aac cta       209
Pro Arg Ala Glu Pro Ala Pro Val Cys Cys Ser Ala Arg Tyr Asn Leu
        30                  35                  40 gca ttt ttg tcc ttt ttt ggt ttc ttc gtt ctc tat tca tta cgg gtg       257
Ala Phe Leu Ser Phe Phe Gly Phe Phe Val Leu Tyr Ser Leu Arg Val
    45                  50                  55 aat ctg agc gtt gca cta gtg gac atg gtg gat tca aac aca act gcc       305
Asn Leu Ser Val Ala Leu Val Asp Met Val Asp Ser Asn Thr Thr Ala
60                  65                  70 aaa gat aat aga acg tcc tac gag tgt gca gag cat tct gct ccc ata       353
Lys Asp Asn Arg Thr Ser Tyr Glu Cys Ala Glu His Ser Ala Pro Ile
75                  80                  85                  90 aaa gtt ctt cac aac caa acg ggt aaa aag tac cgg tgg gat gca gaa       401
Lys Val Leu His Asn Gln Thr Gly Lys Lys Tyr Arg Trp Asp Ala Glu
                95                 100                 105 act caa gga tgg att ctc gga tct ttt ttc tat ggc tac atc atc aca       449
Thr Gln Gly Trp Ile Leu Gly Ser Phe Phe Tyr Gly Tyr Ile Ile Thr
            110                 115                 120 caa att cct gga gga tat gtt gcc agc aga agt ggg ggg aag ctg ttg       497
Gln Ile Pro Gly Gly Tyr Val Ala Ser Arg Ser Gly Gly Lys Leu Leu
        125                 130                 135 cta gga ttc ggg atc ttt gct aca gct atc ttc acc ctg ttc act ccc       545
Leu Gly Phe Gly Ile Phe Ala Thr Ala Ile Phe Thr Leu Phe Thr Pro
    140                 145                 150 ctc gct gca gat ttc gga gtc gga gcc ctt gtt gca ctc agg gca cta       593
Leu Ala Ala Asp Phe Gly Val Gly Ala Leu Val Ala Leu Arg Ala Leu
155                 160                 165                 170 gaa ggg cta gga gag ggt gtc aca tat cca gcc atg cat gcc atg tgg       641
Glu Gly Leu Gly Glu Gly Val Thr Tyr Pro Ala Met His Ala Met Trp
                175                 180                 185 tct tca tgg gct ccc cct ctt gaa aga agc aag ctt ctg agt att tca       689
Ser Ser Trp Ala Pro Pro Leu Glu Arg Ser Lys Leu Leu Ser Ile Ser
            190                 195                 200 tat gca gga gca caa ctt ggg aca gta gtt tct ctt cct ctt tct gga       737
Tyr Ala Gly Ala Gln Leu Gly Thr Val Val Ser Leu Pro Leu Ser Gly
        205                 210                 215 gta att tgc tac tat atg aat tgg act tat gtc ttc tat ttc ttt ggc       785
Val Ile Cys Tyr Tyr Met Asn Trp Thr Tyr Val Phe Tyr Phe Phe Gly
    220                 225                 230 att gtt gga atc atc tgg ttt att tta tgg atc tgc tta gtt agt gat       833
Ile Val Gly Ile Ile Trp Phe Ile Leu Trp Ile Cys Leu Val Ser Asp
235                 240                 245                 250 aca cca gaa act cac aag aca atc act ccc tat gaa aag gag tat att       881
Thr Pro Glu Thr His Lys Thr Ile Thr Pro Tyr Glu Lys Glu Tyr Ile
                255                 260                 265 ctt tca tca tta aaa aat cag ctc tct tca cag aag tca gtg ccg tgg       929
Leu Ser Ser Leu Lys Asn Gln Leu Ser Ser Gln Lys Ser Val Pro Trp
            270                 275                 280
```

```
ata cct atg ctg aaa tca ctg cca ctt tgg gct att gtc gtt gca cat     977
Ile Pro Met Leu Lys Ser Leu Pro Leu Trp Ala Ile Val Val Ala His
        285                 290                 295 ttt tct tac aac tgg act ttt tat act ttg ttg acc tta ttg cct act    1025
Phe Ser Tyr Asn Trp Thr Phe Tyr Thr Leu Leu Thr Leu Leu Pro Thr
300                 305                 310 tac atg aag gaa gtc cta agg ttc aat att caa gag aat ggg ttt tta    1073
Tyr Met Lys Glu Val Leu Arg Phe Asn Ile Gln Glu Asn Gly Phe Leu
315                 320                 325                 330 tct gca gtc cct tat tta ggt tgt tgg tta tgt atg atc ctg tcg ggt    1121
Ser Ala Val Pro Tyr Leu Gly Cys Trp Leu Cys Met Ile Leu Ser Gly
            335                 340                 345 caa gct gct gac aat tta agg gca aga tgg aat ttt tca act ctg tgg    1169
Gln Ala Ala Asp Asn Leu Arg Ala Arg Trp Asn Phe Ser Thr Leu Trp
                350                 355                 360 gtt cga aga gtt ttt agc ctt ata ggg atg att gga cct gcg ata ttc    1217
Val Arg Arg Val Phe Ser Leu Ile Gly Met Ile Gly Pro Ala Ile Phe
            365                 370                 375 ctg gtt gcc gca gga ttt ata ggc tgt gat tat tcc ttg gct gtt gca    1265
Leu Val Ala Ala Gly Phe Ile Gly Cys Asp Tyr Ser Leu Ala Val Ala
        380                 385                 390 ttc cta acc ata tca aca acc ctg gga ggc ttt tgc tct tct gga ttt    1313
Phe Leu Thr Ile Ser Thr Thr Leu Gly Gly Phe Cys Ser Ser Gly Phe
395                 400                 405                 410 agc atc aac cat ctg gac att gct cct tcg tat gct ggt att ctc ctg    1361
Ser Ile Asn His Leu Asp Ile Ala Pro Ser Tyr Ala Gly Ile Leu Leu
            415                 420                 425 ggc atc aca aat acc ttt gcc act att cct gga atg att ggg ccc atc    1409
Gly Ile Thr Asn Thr Phe Ala Thr Ile Pro Gly Met Ile Gly Pro Ile
                430                 435                 440 att gcc aga agt ctt acc cct gag aac act att gga gaa tgg caa act    1457
Ile Ala Arg Ser Leu Thr Pro Glu Asn Thr Ile Gly Glu Trp Gln Thr
            445                 450                 455 gtt ttc tgc atc gct gct gct atc aat gta ttt ggt gcc att ttc ttc    1505
Val Phe Cys Ile Ala Ala Ala Ile Asn Val Phe Gly Ala Ile Phe Phe
        460                 465                 470 aca cta ttc gcc aaa ggt gaa gtg caa aac tgg gcc atc agt gat cac    1553
Thr Leu Phe Ala Lys Gly Glu Val Gln Asn Trp Ala Ile Ser Asp His
475                 480                 485                 490 caa gga cac aga aac tgaaggaacc aataaataat cctgtctcta ttaatgtatc    1608
Gln Gly His Arg Asn
            495 tttgtttatc atgtaaccta aaagtgcctt tgatatttta atgtgtaagc aatctatata    1668 caagataaaa ttgtactaga aaaattgtgt tagatttgta aggcttgtaa tcatgaaatg    1728 tcactagttg ccatataagc aaaattagct atttttaatt attattaacc cgtttgctgg    1788 aacttacaat tcagggtcac atatctggct gcaagtcagg caacccacaa taggggagtt    1848 ctatttattt ataagaccat acctaaagag atgagctgaa atagacccctt ctatacctt    1908 gcttaattaa ggtggataat aattctcagg tcttgttaaa catctgtttt tgtacacctt    1968 cctcaaaaaa ttatttgtca tcagcaatcc ctgacatgta ggtctcaaac tttagcctct    2028 ccacggagct ggcagccact gtatcattca gcctggcaac ttcactgagg gaagcatgcc    2088 caggcagctg ccacatgtcc cctctctggc ttcagggaca gtgcccagca cttaggcagc    2148 atccaagacc agggtcagcg ccaaggcttt ggacggtatt cttcccctgg ggctgttaat    2208 gtgtggatga agccctgagc caacagggac agcgcgatcc acagtcatgg tttccatgca    2268 ccctctccct tcccttccca gcacactgga gtattgcctg gcatgtaacc tgcaaaagaa    2328
```

-continued

```
agtgtgatgc ctaattagcc acatataaca tcatccttga tgatcctacc ttcacatgga   2388
tcagagtata aatcttcaag tcctgtgttc taggagctac accagaataa ttaaaatata   2448
aaaagaaaca aaacattttt tctgtctgac acctaagtgt ctggttgcag ttcaaggtta   2508
aagtgacttc tacttcacat aacctgcaac cggtggtgta atcatcttta gtgttggttt   2568
cttaaatctt attttccag ttttcctgg accatcttcc agtggttttg agcatgcttt    2628
gagggcattt atgtgattta gaacttgatt aatgtttcac tgtgtatgtt caacactacc   2688
tgtaatattt taactaaagc tatttaatgt aaatgatgt gtatacattc tgtaaattaa    2748
tttttaaatc tgtaaatagc tttaagttgc tatggtgata tttctttac aaatcaaaat    2808 aaatcttttt ggaatgataa aaaaaaaaaa aaaaaa                             2844
```

<210> SEQ ID NO 4
<211> LENGTH: 495
<212> TYPE: PRT
<213> ORGANISM: Ovis sp.

<400> SEQUENCE: 4

```
Met Lys Ser Pro Val Ser Asp Leu Ala Pro Ser Asp Gly Glu Glu Gly
 1               5                  10                  15

Ser Asp Arg Thr Pro Leu Leu Gln Arg Ala Pro Arg Ala Glu Pro Ala
            20                  25                  30

Pro Val Cys Cys Ser Ala Arg Tyr Asn Leu Ala Phe Leu Ser Phe Phe
        35                  40                  45

Gly Phe Phe Val Leu Tyr Ser Leu Arg Val Asn Leu Ser Val Ala Leu
    50                  55                  60

Val Asp Met Val Asp Ser Asn Thr Thr Ala Lys Asp Asn Arg Thr Ser
65                  70                  75                  80

Tyr Glu Cys Ala Glu His Ser Ala Pro Ile Lys Val Leu His Asn Gln
                85                  90                  95

Thr Gly Lys Lys Tyr Arg Trp Asp Ala Glu Thr Gln Gly Trp Ile Leu
           100                 105                 110

Gly Ser Phe Phe Tyr Gly Tyr Ile Ile Thr Gln Ile Pro Gly Gly Tyr
       115                 120                 125

Val Ala Ser Arg Ser Gly Gly Lys Leu Leu Gly Phe Gly Ile Phe
   130                 135                 140

Ala Thr Ala Ile Phe Thr Leu Phe Thr Pro Leu Ala Ala Asp Phe Gly
145                 150                 155                 160

Val Gly Ala Leu Val Ala Leu Arg Ala Leu Glu Gly Leu Gly Glu Gly
                165                 170                 175

Val Thr Tyr Pro Ala Met His Ala Met Trp Ser Ser Trp Ala Pro Pro
           180                 185                 190

Leu Glu Arg Ser Lys Leu Leu Ser Ile Ser Tyr Ala Gly Ala Gln Leu
       195                 200                 205

Gly Thr Val Val Ser Leu Pro Leu Ser Gly Val Ile Cys Tyr Tyr Met
   210                 215                 220

Asn Trp Thr Tyr Val Phe Tyr Phe Gly Ile Val Gly Ile Ile Trp
225                 230                 235                 240

Phe Ile Leu Trp Ile Cys Leu Val Ser Asp Thr Pro Glu Thr His Lys
                245                 250                 255

Thr Ile Thr Pro Tyr Glu Lys Glu Tyr Ile Leu Ser Ser Leu Lys Asn
           260                 265                 270

Gln Leu Ser Ser Gln Lys Ser Val Pro Trp Ile Pro Met Leu Lys Ser
```

-continued

```
                275                 280                 285
Leu Pro Leu Trp Ala Ile Val Val Ala His Phe Ser Tyr Asn Trp Thr
            290                 295                 300
Phe Tyr Thr Leu Leu Thr Leu Leu Pro Thr Tyr Met Lys Glu Val Leu
305                 310                 315                 320
Arg Phe Asn Ile Gln Glu Asn Gly Phe Leu Ser Ala Val Pro Tyr Leu
                325                 330                 335
Gly Cys Trp Leu Cys Met Ile Leu Ser Gly Gln Ala Ala Asp Asn Leu
            340                 345                 350
Arg Ala Arg Trp Asn Phe Ser Thr Leu Trp Val Arg Val Phe Ser
                355                 360                 365
Leu Ile Gly Met Ile Gly Pro Ala Ile Phe Leu Val Ala Ala Gly Phe
        370                 375                 380
Ile Gly Cys Asp Tyr Ser Leu Ala Val Ala Phe Leu Thr Ile Ser Thr
385                 390                 395                 400
Thr Leu Gly Gly Phe Cys Ser Ser Gly Phe Ser Ile Asn His Leu Asp
                405                 410                 415
Ile Ala Pro Ser Tyr Ala Gly Ile Leu Leu Gly Ile Thr Asn Thr Phe
            420                 425                 430
Ala Thr Ile Pro Gly Met Ile Gly Pro Ile Ile Ala Arg Ser Leu Thr
                435                 440                 445
Pro Glu Asn Thr Ile Gly Glu Trp Gln Thr Val Phe Cys Ile Ala Ala
        450                 455                 460
Ala Ile Asn Val Phe Gly Ala Ile Phe Phe Thr Leu Phe Ala Lys Gly
465                 470                 475                 480
Glu Val Gln Asn Trp Ala Ile Ser Asp His Gln Gly His Arg Asn
                485                 490                 495

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 5
cgggatcccg ccngcnatgc ayrshrtstg g                                    31

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 6
ggaattccdg gdgcratktc narrtrrtt                                       29

<210> SEQ ID NO 7
<211> LENGTH: 2930
<212> TYPE: DNA
<213> ORGANISM: Homo sapiens
<220> FEATURE:
<221> NAME/KEY: CDS
<222> LOCATION: (263)..(1870)

<400> SEQUENCE: 7
gttcggtcga agccctcccc ttaattatgt gcaattcaag tccccactgc ccgcccgcaa      60
gcccccactc atcctcgctg cgggcagggt ggccctgca ctttacaagg gggtgcagga     120
```

-continued

```
gcgggagacg tcgtccgaa caccggctcc ccggcatgcg tagaccggcg ggcggagcgg        180
gctcactttg cgccaatcct acgagaactc ccagaactcc gcttccctag tccaacccaa        240
gccagagttg cccacaccta ag atg gcg gcg ggg gcg atg aca ccg ccc cgc        292
                          Met Ala Ala Gly Ala Met Thr Pro Pro Arg
                          1               5                    10 ccg gtc cag cca gct cgg ccc ggg ggc ttc ggg ctg tcg ggc cgg cgc         340
Pro Val Gln Pro Ala Arg Pro Gly Gly Phe Gly Leu Ser Gly Arg Arg
            15                  20                  25 tcc ctt ctc tgc cag gtg gcg agt aca cct gct cac gta ggc gtc atg         388
Ser Leu Leu Cys Gln Val Ala Ser Thr Pro Ala His Val Gly Val Met
        30                  35                  40 agg tct ccg gtt cga gac ctg gcc cgg aac gat ggc gag gag agc acg         436
Arg Ser Pro Val Arg Asp Leu Ala Arg Asn Asp Gly Glu Glu Ser Thr
    45                  50                  55 gac cgc acg cct ctt cta ccg ggc gcc cca cgg gcc gaa gcc gct cca         484
Asp Arg Thr Pro Leu Leu Pro Gly Ala Pro Arg Ala Glu Ala Ala Pro
60                  65                  70 gtg tgc tgc tct gct cgt tac aac tta gca att ttg gcc ttt ttt ggt         532
Val Cys Cys Ser Ala Arg Tyr Asn Leu Ala Ile Leu Ala Phe Phe Gly
75                  80                  85                  90 ttc ttc att gtg tat gca tta cgt gtg aat ctg agt gtt gcg tta gtg         580
Phe Phe Ile Val Tyr Ala Leu Arg Val Asn Leu Ser Val Ala Leu Val
                95                  100                 105 gat atg gta gat tca aat aca act tta gaa gat aat aga act tcc aag         628
Asp Met Val Asp Ser Asn Thr Thr Leu Glu Asp Asn Arg Thr Ser Lys
            110                 115                 120 gcg tgt cca gag cat tct gct ccc ata aaa gtt cat cat aat caa acg         676
Ala Cys Pro Glu His Ser Ala Pro Ile Lys Val His His Asn Gln Thr
        125                 130                 135 ggt aag aag tac caa tgg gat gca gaa act caa gga tgg att ctc ggt         724
Gly Lys Lys Tyr Gln Trp Asp Ala Glu Thr Gln Gly Trp Ile Leu Gly
    140                 145                 150 tcc ttt ttt tat ggc tac atc atc aca cag att cct gga gga tat gtt         772
Ser Phe Phe Tyr Gly Tyr Ile Ile Thr Gln Ile Pro Gly Gly Tyr Val
155                 160                 165                 170 gcc agc aaa ata ggg ggg aaa atg ctg cta gga ttt ggg atc ctt ggc         820
Ala Ser Lys Ile Gly Gly Lys Met Leu Leu Gly Phe Gly Ile Leu Gly
                175                 180                 185 act gct gtc ctc acc ctg ttc act ccc att gct gca gat tta gga gtt         868
Thr Ala Val Leu Thr Leu Phe Thr Pro Ile Ala Ala Asp Leu Gly Val
            190                 195                 200 gga cca ctc att gta ctc aga gca cta gaa gga cta gga gag ggt gtt         916
Gly Pro Leu Ile Val Leu Arg Ala Leu Glu Gly Leu Gly Glu Gly Val
        205                 210                 215 aca ttt cca gcc atg cat gcc atg tgg tct tct tgg gct ccc cct ctt         964
Thr Phe Pro Ala Met His Ala Met Trp Ser Ser Trp Ala Pro Pro Leu
    220                 225                 230 gaa aga agc aaa ctt ctt agc att tcg tat gca gga gca cag ctt ggg        1012
Glu Arg Ser Lys Leu Leu Ser Ile Ser Tyr Ala Gly Ala Gln Leu Gly
235                 240                 245                 250 aca gta att tct ctt cct ctt tct gga ata att tgc tac tat atg aat        1060
Thr Val Ile Ser Leu Pro Leu Ser Gly Ile Ile Cys Tyr Tyr Met Asn
                255                 260                 265 tgg act tat gtc ttc tac ttt ttt ggt act att gga ata ttt tgg ttt        1108
Trp Thr Tyr Val Phe Tyr Phe Phe Gly Thr Ile Gly Ile Phe Trp Phe
            270                 275                 280 ctt ttg tgg atc tgg tta gtt agt gac aca cca caa aaa cac aag aga        1156
Leu Leu Trp Ile Trp Leu Val Ser Asp Thr Pro Gln Lys His Lys Arg
```

-continued

```
                    285                 290                 295
att tcc cat tat gaa aag gaa tac att ctt tca tca tta aga aat cag    1204
Ile Ser His Tyr Glu Lys Glu Tyr Ile Leu Ser Ser Leu Arg Asn Gln
300                 305                 310 ctt tct tca cag aag tca gtg ccg tgg gta ccc att tta aaa tcc ctg    1252
Leu Ser Ser Gln Lys Ser Val Pro Trp Val Pro Ile Leu Lys Ser Leu
315                 320                 325                 330 cca ctt tgg gct atc gta gtt gca cac ttt tct tac aac tgg act ttt    1300
Pro Leu Trp Ala Ile Val Val Ala His Phe Ser Tyr Asn Trp Thr Phe
                335                 340                 345 tat act tta ttg aca tta ttg cct act tat atg aag gag atc cta agg    1348
Tyr Thr Leu Leu Thr Leu Leu Pro Thr Tyr Met Lys Glu Ile Leu Arg
350                 355                 360 ttc aat gtt caa gag aat ggg ttt tta tct tca ttg cct tat tta ggc    1396
Phe Asn Val Gln Glu Asn Gly Phe Leu Ser Ser Leu Pro Tyr Leu Gly
                365                 370                 375 tct tgg tta tgt atg atc ctg tct ggt caa gct gct gac aat tta agg    1444
Ser Trp Leu Cys Met Ile Leu Ser Gly Gln Ala Ala Asp Asn Leu Arg
380                 385                 390 gca aaa tgg aat ttt tca act tta tgt gtt cgc aga att ttt agc ctt    1492
Ala Lys Trp Asn Phe Ser Thr Leu Cys Val Arg Arg Ile Phe Ser Leu
395                 400                 405                 410 ata gga atg att gga cct gca gta ttc ctg gta gct gct ggc ttc att    1540
Ile Gly Met Ile Gly Pro Ala Val Phe Leu Val Ala Ala Gly Phe Ile
                415                 420                 425 ggc tgt gat tat tct ttg gcc gtt gct ttc cta act ata tca aca aca    1588
Gly Cys Asp Tyr Ser Leu Ala Val Ala Phe Leu Thr Ile Ser Thr Thr
430                 435                 440 ctg gga ggc ttt tgc tct tct gga ttt agc atc aac cat ctg gat att    1636
Leu Gly Gly Phe Cys Ser Ser Gly Phe Ser Ile Asn His Leu Asp Ile
                445                 450                 455 gct cct tcg tat gct ggt atc ctc ctg ggc atc aca aat aca ttt gcc    1684
Ala Pro Ser Tyr Ala Gly Ile Leu Leu Gly Ile Thr Asn Thr Phe Ala
460                 465                 470 act att cca gga atg gtt ggg ccc gtc att gct aaa agt ctg acc cct    1732
Thr Ile Pro Gly Met Val Gly Pro Val Ile Ala Lys Ser Leu Thr Pro
475                 480                 485                 490 gat aac act gtt gga gaa tgg caa acc gtg ttc tat att gct gct gct    1780
Asp Asn Thr Val Gly Glu Trp Gln Thr Val Phe Tyr Ile Ala Ala Ala
                495                 500                 505 att aat gtt ttt ggt gcc att ttc ttt aca cta ttc gcc aaa ggt gaa    1828
Ile Asn Val Phe Gly Ala Ile Phe Phe Thr Leu Phe Ala Lys Gly Glu
                510                 515                 520 gta caa aac tgg gct ctc aat gat cac cat gga cac aga cac              1870
Val Gln Asn Trp Ala Leu Asn Asp His His Gly His Arg His
                525                 530                 535 tgaaggaacc aataaataat cctgcctcta ttaatgtatt tttatttatc atgtaacctc    1930
aaagtgcctt ctgtattgtg taagcattct atgtcttttt ttaattgtac ttgtattaga    1990
tttttaaggc ctataatcat gaaatatcac tagttgccag aataataaaa tgaactgtgt    2050
ttaattatga ataatatgta agctaggact tctactttag gttcacatac ctgcctgcta    2110
gtcgggcaac atgaagtagg acagttctgt tgattttta gggccatact aaagggaatg     2170
agctgaaaca gacctcctga tacctttgct taattaaact agatgataat tctcaggtac    2230
tgataaacac ctgttgttgt tcactttcct cataaaaatt gtcagctctc tctgacactt    2290
agacctcaaa ctttagcatc tctgtggagc tgccatccac tgtataattt cgcctggcaa    2350
ctggactgag gggagtgtgc ccaggcagct gccaagcact ccctcctggg cttcagggtc    2410
```

-continued

```
agagtgccca gcgtttatca gaggcagcat ccaagcccag agccagtgtc gactcttcgg   2470
ctggtgcctt tcctctgagg ggctatcaat gtgtagataa agccctgagt aggcaagagc   2530
agtgagatcc actgctatgg tcttgataca tcctcaaact ttcccttccc agcacagagg   2590
aatattggct ggcatgcaac ctgcaaaaga aaaatgcgaa gcggccgggc acggtggctc   2650
atgcctgtaa tcccagcact ttgggggggct gaggtgggcg aatcatgaga tcaggagttc   2710
gagaccagcc tggccagcat ggtgaaaccc catctctact aaaaatacaa aaaattagct   2770
gggcgtggtg acgggcgcct gtaatcccag atactcagga ggctgaggta ggagaatcac   2830
ttgaacctgg gaggtggaag ttgcagtgaa ccaagatcac gccactgcac tccagcctgg   2890
gcgatggagc gagactccaa ctcaaaaaaa aaaaaaaaa                          2930

<210> SEQ ID NO 8
<211> LENGTH: 536
<212> TYPE: PRT
<213> ORGANISM: Homo sapiens

<400> SEQUENCE: 8

Met Ala Ala Gly Ala Met Thr Pro Pro Arg Pro Val Gln Pro Ala Arg
  1               5                  10                  15

Pro Gly Gly Phe Gly Leu Ser Gly Arg Arg Ser Leu Leu Cys Gln Val
             20                  25                  30

Ala Ser Thr Pro Ala His Val Gly Val Met Arg Ser Pro Val Arg Asp
         35                  40                  45

Leu Ala Arg Asn Asp Gly Glu Glu Ser Thr Asp Arg Thr Pro Leu Leu
     50                  55                  60

Pro Gly Ala Pro Arg Ala Glu Ala Ala Pro Val Cys Cys Ser Ala Arg
 65                  70                  75                  80

Tyr Asn Leu Ala Ile Leu Ala Phe Phe Gly Phe Phe Ile Val Tyr Ala
                 85                  90                  95

Leu Arg Val Asn Leu Ser Val Ala Leu Val Asp Met Val Asp Ser Asn
            100                 105                 110

Thr Thr Leu Glu Asp Asn Arg Thr Ser Lys Ala Cys Pro Glu His Ser
        115                 120                 125

Ala Pro Ile Lys Val His His Asn Gln Thr Gly Lys Lys Tyr Gln Trp
    130                 135                 140

Asp Ala Glu Thr Gln Gly Trp Ile Leu Gly Ser Phe Phe Tyr Gly Tyr
145                 150                 155                 160

Ile Ile Thr Gln Ile Pro Gly Gly Tyr Val Ala Ser Lys Ile Gly Gly
                165                 170                 175

Lys Met Leu Leu Gly Phe Gly Ile Leu Gly Thr Ala Val Leu Thr Leu
            180                 185                 190

Phe Thr Pro Ile Ala Ala Asp Leu Gly Val Gly Pro Leu Ile Val Leu
        195                 200                 205

Arg Ala Leu Glu Gly Leu Gly Glu Gly Val Thr Phe Pro Ala Met His
    210                 215                 220

Ala Met Trp Ser Ser Trp Ala Pro Pro Leu Glu Arg Ser Lys Leu Leu
225                 230                 235                 240

Ser Ile Ser Tyr Ala Gly Ala Gln Leu Gly Thr Val Ile Ser Leu Pro
                245                 250                 255

Leu Ser Gly Ile Ile Cys Tyr Tyr Met Asn Trp Thr Tyr Val Phe Tyr
            260                 265                 270

Phe Phe Gly Thr Ile Gly Ile Phe Trp Phe Leu Leu Trp Ile Trp Leu
```

```
                275                 280                 285
Val Ser Asp Thr Pro Gln Lys His Lys Arg Ile Ser His Tyr Glu Lys
        290                 295                 300

Glu Tyr Ile Leu Ser Ser Leu Arg Asn Gln Leu Ser Ser Gln Lys Ser
305                 310                 315                 320

Val Pro Trp Val Pro Ile Leu Lys Ser Leu Pro Leu Trp Ala Ile Val
                325                 330                 335

Val Ala His Phe Ser Tyr Asn Trp Thr Phe Tyr Thr Leu Leu Thr Leu
                340                 345                 350

Leu Pro Thr Tyr Met Lys Glu Ile Leu Arg Phe Asn Val Gln Glu Asn
                355                 360                 365

Gly Phe Leu Ser Ser Leu Pro Tyr Leu Gly Ser Trp Leu Cys Met Ile
        370                 375                 380

Leu Ser Gly Gln Ala Ala Asp Asn Leu Arg Ala Lys Trp Asn Phe Ser
385                 390                 395                 400

Thr Leu Cys Val Arg Arg Ile Phe Ser Leu Ile Gly Met Ile Gly Pro
                405                 410                 415

Ala Val Phe Leu Val Ala Ala Gly Phe Ile Gly Cys Asp Tyr Ser Leu
                420                 425                 430

Ala Val Ala Phe Leu Thr Ile Ser Thr Thr Leu Gly Gly Phe Cys Ser
                435                 440                 445

Ser Gly Phe Ser Ile Asn His Leu Asp Ile Ala Pro Ser Tyr Ala Gly
        450                 455                 460

Ile Leu Leu Gly Ile Thr Asn Thr Phe Ala Thr Ile Pro Gly Met Val
465                 470                 475                 480

Gly Pro Val Ile Ala Lys Ser Leu Thr Pro Asp Asn Thr Val Gly Glu
                485                 490                 495

Trp Gln Thr Val Phe Tyr Ile Ala Ala Ala Ile Asn Val Phe Gly Ala
                500                 505                 510

Ile Phe Phe Thr Leu Phe Ala Lys Gly Glu Val Gln Asn Trp Ala Leu
                515                 520                 525

Asn Asp His His Gly His Arg His
        530                 535

<210> SEQ ID NO 9
<211> LENGTH: 1485
<212> TYPE: DNA
<213> ORGANISM: Artificial Sequence
<220> FEATURE:
<223> OTHER INFORMATION: Description of Artificial Sequence: human/sheep
      consensus sequence
<220> FEATURE:
<221> NAME/KEY: CDS
<222> LOCATION: (1)..(1485)

<400> SEQUENCE: 9 atg arg tcy ccg gtt ysr gac ytr gcc csg arc gay ggc gag gag rgc      48
Met Xaa Xaa Pro Val Xaa Asp Xaa Ala Xaa Xaa Gly Glu Glu Xaa
1               5                   10                  15 wcg gac cgc acr cck cty ctr cmg s

-continued

| | | | | | | | | | | | | | | | |
|---|---|---|---|---|---|---|---|---|---|---|---|---|---|---|---|
| gtg | gay | atg | gtr | gat | tca | aay | aca | act | kym | raa | gat | aat | aga | ack | tcc | 240 |
| Val | Xaa | Met | Xaa | Asp | Ser | Xaa | Thr | Thr | Xaa | Xaa | Asp | Asn | Arg | Xaa | Ser | |
| 65 | | | | 70 | | | | | 75 | | | | | 80 | | | was gmg tgt sca gag cat tct gct ccc ata aaa gtt cwt cay aay caa    288
Xaa Xaa Cys Xaa Glu His Ser Ala Pro Ile Lys Val Xaa Xaa Xaa Gln
            85                      90                      95 acg ggt aar aag tac crr tgg gat gca gaa act caa gga tgg att ctc    336
Thr Gly Xaa Lys Tyr Xaa Trp Asp Ala Glu Thr Gln Gly Trp Ile Leu
           100                     105                    110 ggw tcy ttt tty tat ggc tac atc atc aca car att cct gga gga tat    384
Xaa Xaa Phe Xaa Tyr Gly Tyr Ile Ile Thr Xaa Ile Pro Gly Gly Tyr
           115                     120                    125 gtt gcc agc ara akw ggg ggg aar mtg ytg cta gga tty ggg atc ytt    432
Val Ala Ser Xaa Xaa Gly Gly Xaa Xaa Leu Gly Xaa Gly Ile Xaa
           130                     135                    140 gsy acw gct rtc ytc acc ctg ttc act ccc mty gct gca gat ttm gga    480
Xaa Xaa Ala Xaa Xaa Thr Leu Phe Thr Pro Xaa Ala Ala Asp Xaa Gly
145                     150                     155                    160 gty gga scm cty rtt gya ctc agr gca cta gaa ggr cta gga gag ggt    528
Xaa Gly Xaa Xaa Xaa Xaa Leu Xaa Ala Leu Glu Xaa Leu Gly Glu Gly
           165                     170                    175 gty aca twt cca gcc atg cat gcc atg tgg tct tcw tgg gct ccc cct    576
Xaa Thr Xaa Pro Ala Met His Ala Met Trp Ser Xaa Trp Ala Pro Pro
           180                     185                    190 ctt gaa aga agc aar ctt ctk agy att tcr tat gca gga gca car ctt    624
Leu Glu Arg Ser Xaa Leu Xaa Xaa Ile Xaa Tyr Ala Gly Ala Xaa Leu
           195                     200                    205 ggg aca gta rtt tct ctt cct ctt tct gga rta att tgc tac tat atg    672
Gly Thr Val Xaa Ser Leu Pro Leu Ser Gly Xaa Ile Cys Tyr Tyr Met
           210                     215                    220 aat tgg act tat gtc ttc tay tty ttt ggy ayt rtt gga atm wty tgg    720
Asn Trp Thr Tyr Val Phe Xaa Xaa Phe Xaa Xaa Xaa Gly Xaa Xaa Trp
225                     230                     235                    240 ttt mtt ttr tgg atc tgs tta gtt agt gay aca cca saa amw cac aag    768
Phe Xaa Xaa Trp Ile Xaa Leu Val Ser Xaa Thr Pro Xaa Xaa His Lys
           245                     250                    255 asa aty wcy cmy tat gaa aag gar tay att ctt tca tca tta ara aat    816
Xaa Xaa Xaa Xaa Tyr Glu Lys Xaa Xaa Ile Leu Ser Ser Leu Xaa Asn
           260                     265                    270 cag cty tct tca cag aag tca gtg ccg tgg rta ccy atk ytr aaa tcm    864
Gln Xaa Ser Ser Gln Lys Ser Val Pro Trp Xaa Xaa Xaa Xaa Lys Xaa
           275                     280                    285 ctg cca ctt tgg gct aty gtm gtt gca cay ttt tct tac aac tgg act    912
Leu Pro Leu Trp Ala Xaa Xaa Val Ala Xaa Phe Ser Tyr Asn Trp Thr
           290                     295                    300 ttt tat act ttr ttg acm tta ttg cct act tay atg aag gar tca cta    960
Phe Tyr Thr Xaa Leu Xaa Leu Leu Pro Thr Xaa Met Lys Xaa Xaa Leu
305                     310                     315                    320 agg ttc aat rtt caa gag aat ggg ttt tta tct kca kts cct tat tta   1008
Arg Phe Asn Xaa Gln Glu Asn Gly Phe Leu Ser Xaa Xaa Pro Tyr Leu
           325                     330                    335 ggy tst tgg tta tgt atg atc ctg tck ggt caa gct gct gac aat tta   1056
Xaa Xaa Trp Leu Cys Met Ile Leu Xaa Gly Gln Ala Ala Asp Asn Leu
           340                     345                    350 agg gca ara tgg aat ttt tca act ytr tgk gtt cgm aga rtt ttt agc   1104
Arg Ala Xaa Trp Asn Phe Ser Thr Xaa Xaa Val Xaa Arg Xaa Phe Ser
           355                     360                    365 ctt ata ggr atg att gga cct gcr rta ttc ctg gtw gcy gcc ggm tty   1152
Leu Ile Xaa Met Ile Gly Pro Xaa Xaa Phe Leu Xaa Xaa Xaa Xaa Xaa

```
                370                  375                  380
atw ggc tgt gat tat tcy ttg gcy gtt gcw ttc cta acy ata tca aca       1200
Xaa Gly Cys Asp Tyr Xaa Leu Xaa Val Xaa Phe Leu Xaa Ile Ser Thr
385                 390                  395                  400 acm ctg gga ggc ttt tgc tct tct gga ttt agc atc aac cat ctg gay       1248
Xaa Leu Gly Gly Phe Cys Ser Ser Gly Phe Ser Ile Asn His Leu Xaa
                405                  410                  415 att gct cct tcg tat gct ggt aty ctc ctg ggc atc aca aat acm ttt       1296
Ile Ala Pro Ser Tyr Ala Gly Xaa Leu Leu Gly Ile Thr Asn Xaa Phe
                420                  425                  430 gcc act att ccw gga atg rtt ggg ccc rtc att gcy ara agt ctk acc       1344
Ala Thr Ile Xaa Gly Met Xaa Gly Pro Xaa Ile Xaa Xaa Ser Xaa Thr
                435                  440                  445 cct gak aac act rtt gga gaa tgg caa acy gtk ttc try aty gct gct       1392
Pro Xaa Asn Thr Xaa Gly Glu Trp Gln Xaa Xaa Phe Xaa Xaa Ala Ala
                450                  455                  460 gct aty aat gtw ttt ggt gcc att ttc tty aca cta ttc gcc aaa ggt       1440
Ala Xaa Asn Xaa Phe Gly Ala Ile Phe Xaa Thr Leu Phe Ala Lys Gly
465                 470                  475                  480 gaa gtr caa aac tgg gcy mtc art gat cac caw gga cac aga mac           1485
Glu Xaa Gln Asn Trp Xaa Xaa Xaa Asp His Xaa Gly His Arg Xaa
                485                  490                  495

<210> SEQ ID NO 10
<211> LENGTH: 495
<212> TYPE: PRT
<213> ORGANISM: Artificial Sequence
<220> FEATURE:
<223> OTHER INFORMATION: :

<400> SEQUENCE: 10

Met Xaa Xaa Pro Val Xaa Asp Xaa Ala Xaa Xaa Xaa Gly Glu Glu Xaa
 1               5                  10                  15

Xaa Asp Arg Xaa Xaa Xaa Xaa Xaa Ala Xaa Arg Xaa Glu Xaa Ala
             20                  25                  30

Pro Xaa Cys Cys Ser Ala Arg Tyr Asn Xaa Ala Xaa Leu Xaa Phe Phe
         35                  40                  45

Gly Phe Phe Xaa Xaa Tyr Xaa Leu Xaa Val Asn Leu Xaa Val Xaa Xaa
     50                  55                  60

Val Xaa Met Xaa Asp Ser Xaa Thr Thr Xaa Xaa Asp Asn Arg Xaa Ser
 65                  70                  75                  80

Xaa Xaa Cys Xaa Glu His Ser Ala Pro Ile Lys Val Xaa Xaa Xaa Gln
                 85                  90                  95

Thr Gly Xaa Lys Tyr Xaa Trp Asp Ala Glu Thr Gln Gly Trp Ile Leu
            100                 105                 110

Xaa Xaa Phe Xaa Tyr Gly Tyr Ile Ile Thr Xaa Ile Pro Gly Gly Tyr
        115                 120                 125

Val Ala Ser Xaa

```
Gly Thr Val Xaa Ser Leu Pro Leu Ser Gly Xaa Ile Cys Tyr Tyr Met
        210                 215                 220

Asn Trp Thr Tyr Val Phe Xaa Xaa Phe Xaa Xaa Xaa Gly Xaa Xaa Trp
225                 230                 235                 240

Phe Xaa Xaa Trp Ile Xaa Leu Val Ser Xaa Thr Pro Xaa Xaa His Lys
                245                 250                 255

Xaa Xaa Xaa Xaa Tyr Glu Lys Xaa Xaa Ile Leu Ser Ser Leu Xaa Asn
        260                 265                 270

Gln Xaa Ser Ser Gln Lys Ser Val Pro Trp Xaa Xaa Xaa Xaa Lys Xaa
        275                 280                 285

Leu Pro Leu Trp Ala Xaa Xaa Val Ala Xaa Phe Ser Tyr Asn Trp Thr
290                 295                 300

Phe Tyr Thr Xaa Leu Xaa Leu Leu Pro Thr Xaa Met Lys Xaa Xaa Leu
305                 310                 315                 320

Arg Phe Asn Xaa Gln Glu Asn Gly Phe Leu Ser Xaa Xaa Pro Tyr Leu
                325                 330                 335

Xaa Xaa Trp Leu Cys Met Ile Leu Xaa Gly Gln Ala Ala Asp Asn Leu
        340                 345                 350

Arg Ala Xaa Trp Asn Phe Ser Thr Xaa Xaa Val Xaa Arg Xaa Phe Ser
        355                 360                 365

Leu Ile Xaa Met Ile Gly Pro Xaa Xaa Phe Leu Xaa Xaa Xaa Xaa Xaa
370                 375                 380

Xaa Gly Cys Asp Tyr Xaa Leu Xaa Val Xaa Phe Leu Xaa Ile Ser Thr
385                 390                 395                 400

Xaa Leu Gly Gly Phe Cys Ser Ser Gly Phe Ser Ile Asn His Leu Xaa
                405                 410                 415

Ile Ala Pro Ser Tyr Ala Gly Xaa Leu Leu Gly Ile Thr Asn Xaa Phe
                420                 425                 430

Ala Thr Ile Xaa Gly Met Xaa Gly Pro Xaa Ile Xaa Xaa Ser Xaa Thr
        435                 440                 445

Pro Xaa Asn Thr Xaa Gly Glu Trp Gln Xaa Xaa Phe Xaa Xaa Ala Ala
450                 455                 460

Ala Xaa Asn Xaa Phe Gly Ala Ile Phe Xaa Thr Leu Phe Ala Lys Gly
465                 470                 475                 480

Glu Xaa Gln Asn Trp Xaa Xaa Xaa Asp His Xaa Gly His Arg Xaa
                485                 490                 495

<210> SEQ ID NO 11
<211> LENGTH: 1485
<212> TYPE: DNA
<213> ORGANISM: Artificial Sequence
<220> FEATURE:
<223> OTHER INFORMATION: Description of Artificial Sequence: human/sheep
      consencus sequence
<220> FEATURE:
<221> NAME/KEY: CDS
<222> LOCATION: (1)..(1485)

<400> SEQUENCE: 11 atg ang tcn ccg gtt nnn gac ntn gcc cng anc gan ggc gag gag ngc      48
Met Xaa Xaa Pro Val Xaa Asp Xaa Ala Xaa Xaa Xaa Gly Glu Glu Xaa
 1               5                  10                  15 ncg gac cgc acn ccn ctn ctn cng ngc gcc ccn cgg gcn gaa ncc gct      96
Xaa Asp Arg Xaa Xaa Xaa Xaa Xaa Xaa Ala Xaa Arg Xaa Glu Xaa Ala
                20                  25                  30 cca gtn tgc tgc tct gct cgt tac aac nta gca ntt ttg ncc ttt ttt    144
Pro Xaa Cys Cys Ser Ala Arg Tyr Asn Xaa Ala Xaa Leu Xaa Phe Phe
            35                  40                  45
```

| | | |
|---|---|---|
| ggt ttc ttc ntt ntn tat nca tta cgn gtg aat ctg agn gtt gcn nta<br>Gly Phe Phe Xaa Xaa Tyr Xaa Leu Xaa Val Asn Leu Xaa Val Xaa Xaa<br>    50                           55                           60 | | 192 |
| gtg gan atg gtn gat tca aan aca act nnn naa gat aat aga acn tcc<br>Val Xaa Met Xaa Asp Ser Xaa Thr Thr Xaa Xaa Asp Asn Arg Xaa Ser<br>65                           70                           75                           80 | | 240 |
| nan gng tgt nca gag cat tct gct ccc ata aaa gtt cnt can aan caa<br>Xaa Xaa Cys Xaa Glu His Ser Ala Pro Ile Lys Val Xaa Xaa Xaa Gln<br>                                 85                           90                           95 | | 288 |
| acg ggt aan aag tac cnn tgg gat gca gaa act caa gga tgg att ctc<br>Thr Gly Xaa Lys Tyr Xaa Trp Asp Ala Glu Thr Gln Gly Trp Ile Leu<br>               100                        105                        110 | | 336 |
| ggn tcn ttt ttn tat ggc tac atc atc aca can att cct gga gga tat<br>Xaa Xaa Phe Xaa Tyr Gly Tyr Ile Ile Thr Xaa Ile Pro Gly Gly Tyr<br>             115                       120                         125 | | 384 |
| gtt gcc agc ana ann ggg ggg aan ntg ntg cta gga ttn ggg atc ntt<br>Val Ala Ser Xaa Xaa Gly Gly Xaa Xaa Xaa Leu Gly Xaa Gly Ile Xaa<br>130                          135                                140 | | 432 |
| gnn acn gct ntc ntc acc ctg ttc act ccc ntn gct gca gat ttn gga<br>Xaa Xaa Ala Xaa Xaa Thr Leu Phe Thr Pro Xaa Ala Ala Asp Xaa Gly<br>145                          150                           155                           160 | | 480 |
| gtn gga ncn ctn ntt gna ctc agn gca cta gaa ggn cta gga gag ggt<br>Xaa Gly Xaa Xaa Xaa Xaa Leu Xaa Ala Leu Glu Xaa Leu Gly Glu Gly<br>               165                        170                         175 | | 528 |
| gtn aca tnt cca gcc atg cat gcc atg tgg tct tcn tgg gct ccc cct<br>Xaa Thr Xaa Pro Ala Met His Ala Met Trp Ser Xaa Trp Ala Pro Pro<br>             180                        185                        190 | | 576 |
| ctt gaa aga agc aan ctt ctn agn att tcn tat gca gga gca can ctt<br>Leu Glu Arg Ser Xaa Leu Xaa Xaa Ile Xaa Tyr Ala Gly Ala Xaa Leu<br>             195                        200                        205 | | 624 |
| ggg aca gta ntt tct ctt cct ctt tct gga nta att tgc tac tat atg<br>Gly Thr Val Xaa Ser Leu Pro Leu Ser Gly Xaa Ile Cys Tyr Tyr Met<br>             210                        215                        220 | | 672 |
| aat tgg act tat gtc ttc tan ttn ttt ggn ant ntt gga atn ntn tgg<br>Asn Trp Thr Tyr Val Phe Xaa Xaa Phe Xaa Xaa Xaa Gly Xaa Xaa Trp<br>225                         230                           235                         240 | | 720 |
| ttt ntt ttn tgg atc tgn tta gtt agt gan aca cca naa ann cac aag<br>Phe Xaa Xaa Trp Ile Xaa Leu Val Ser Xaa Thr Pro Xaa Xaa His Lys<br>                           245                        250                        255 | | 768 |
| ana atn ncn cnn tat gaa aag gan tan att ctt tca tca tta ana aat<br>Xaa Xaa Xaa Xaa Tyr Glu Lys Xaa Xaa Ile Leu Ser Ser Leu Xaa Asn<br>                           260                        265                        270 | | 816 |
| cag ctn tct tca cag aag tca gtg ccg tgg nta ccn atn ntn aaa tcn<br>Gln Xaa Ser Ser Gln Lys Ser Val Pro Trp Xaa Xaa Xaa Xaa Lys Xaa<br>             275                        280                        285 | | 864 |
| ctg cca ctt tgg gct atn gtn gtt gca can ttt tct tac aac tgg act<br>Leu Pro Leu Trp Ala Xaa Xaa Val Ala Xaa Phe Ser Tyr Asn Trp Thr<br>             290                        295                        300 | | 912 |
| ttt tat act ttn ttg acn tta ttg cct act tan atg aag gan ntc cta<br>Phe Tyr Thr Xaa Leu Xaa Leu Leu Pro Thr Xaa Met Lys Xaa Xaa Leu<br>305                         310                           315                         320 | | 960 |
| agg ttc aat ntt caa gag aat ggg ttt tta tct nca ntn cct tat tta<br>Arg Phe Asn Xaa Gln Glu Asn Gly Phe Leu Ser Xaa Xaa Pro Tyr Leu<br>                           325                        330                        335 | | 1008 |
| ggn tnt tgg tta tgt atg atc ctg tcn ggt caa gct gct gac aat tta<br>Xaa Xaa Trp Leu Cys Met Ile Leu Xaa Gly Gln Ala Ala Asp Asn Leu<br>             340                        345                        350 | | 1056 |
| agg gca ana tgg aat ttt tca act ntn tgn gtt cgn aga ntt ttt agc<br>Arg Ala Xaa Trp Asn Phe Ser Thr Xaa Xaa Val Xaa Arg Xaa Phe Ser | | 1104 |

```
                355                 360                 365
ctt ata ggn atg att gga cct gcn nta ttc ctg gtn gcn gcn ggn ttn       1152
Leu Ile Xaa Met Ile Gly Pro Xaa Xaa Phe Leu Xaa Xaa Xaa Xaa
        370                 375                 380 atn ggc tgt gat tat tcn ttg gcn gtt gcn ttc cta acn ata tca aca       1200
Xaa Gly Cys Asp Tyr Xaa Leu Xaa Val Xaa Phe Leu Xaa Ile Ser Thr
385                 390                 395                 400 acn ctg gga ggc ttt tgc tct tct gga ttt agc atc aac cat ctg gan       1248
Xaa Leu Gly Gly Phe Cys Ser Ser Gly Phe Ser Ile Asn His Leu Xaa
                405                 410                 415 att gct cct tcg tat gct ggt atn ctc ctg ggc atc aca aat acn ttt       1296
Ile Ala Pro Ser Tyr Ala Gly Xaa Leu Leu Gly Ile Thr Asn Xaa Phe
                420                 425                 430 gcc act att ccn gga atg ntt ggg ccc ntc att gcn ana agt ctn acc       1344
Ala Thr Ile Xaa Gly Met Xaa Gly Pro Xaa Ile Xaa Xaa Ser Xaa Thr
                435                 440                 445 cct gan aac act ntt gga gaa tgg caa acn gtn ttc tnn atn gct gct       1392
Pro Xaa Asn Thr Xaa Gly Glu Trp Gln Xaa Val Phe Xaa Xaa Ala Ala
450                 455                 460 gct atn aat gtn ttt ggt gcc att ttc ttn aca cta ttc gcc aaa ggt       1440
Ala Xaa Asn Xaa Phe Gly Ala Ile Phe Xaa Thr Leu Phe Ala Lys Gly
465                 470                 475                 480 gaa gtn caa aac tgg gcn ntc ant gat cac can gga cac aga nac           1485
Glu Xaa Gln Asn Trp Xaa Xaa Xaa Asp His Xaa Gly His Arg Xaa
                485                 490                 495

<210> SEQ ID NO 12
<211> LENGTH: 495
<212> TYPE: PRT
<213> ORGANISM: Artificial Sequence
<220> FEATURE:
<223> OTHER INFORMATION: :

<400> SEQUENCE: 12

Met Xaa Xaa Pro Val Xaa Asp Xaa Ala Xaa Xaa Xaa Gly Glu Glu Xaa
1               5                   10                  15

Xaa Asp Arg Xaa Xaa Xaa Xaa Xaa Ala Xaa Arg Xaa Glu Xaa Ala
            20                  25                  30

Pro Xaa Cys Cys Ser Ala Arg Tyr Asn Xaa Ala Xaa Leu Xaa Phe Phe
        35                  40                  45

Gly Phe Phe Xaa Xaa Tyr Xaa Leu Xaa Val Asn Leu Xaa Val Xaa Xaa
    50                  55                  60

Val Xaa Met Xaa Asp Ser Xaa Thr Thr Xaa Xaa Asp Asn Arg Xaa Ser
65                  70                  75                  80

Xaa Xaa Cys Xaa Glu His Ser Ala Pro Ile Lys Val Xaa Xaa Xaa Gln
                85                  90                  95

Thr Gly Xaa Lys Tyr Xaa Trp Asp Ala Glu Thr Gln Gly Trp Ile Leu
            100                 105                 110

Xaa Xaa Phe Xaa Tyr Gly Tyr Ile Ile Thr Xaa Ile Pro Gly Gly Tyr
        115                 120                 125

Val Ala Ser Xaa Xaa Gly Gly Xaa Xaa Xaa Leu Gly Xaa Gly Ile Xaa
    130                 135                 140

Xaa Xaa Ala Xaa Xaa Thr Leu Phe Thr Pro Xaa Ala Ala Asp Xaa Gly
145                 150                 155                 160

Xaa Gly Xaa Xaa Xaa Xaa Leu Xaa Ala Leu Glu Xaa Leu Gly Glu Gly
                165                 170                 175

Xaa Thr Xaa Pro Ala Met His Ala Met Trp Ser Xaa Trp Ala Pro Pro
            180                 185                 190
```

```
Leu Glu Arg Ser Xaa Leu Xaa Xaa Ile Xaa Tyr Ala Gly Ala Xaa Leu
        195                 200                 205

Gly Thr Val Xaa Ser Leu Pro Leu Ser Gly Xaa Ile Cys Tyr Tyr Met
        210                 215                 220

Asn Trp Thr Tyr Val Phe Xaa Xaa Phe Xaa Xaa Xaa Gly Xaa Xaa Trp
225                 230                 235                 240

Phe Xaa Xaa Trp Ile Xaa Leu Val Ser Xaa Thr Pro Xaa Xaa His Lys
            245                 250                 255

Xaa Xaa Xaa Xaa Tyr Glu Lys Xaa Xaa Ile Leu Ser Ser Leu Xaa Asn
            260                 265                 270

Gln Xaa Ser Ser Gln Lys Ser Val Pro Trp Xaa Xaa Xaa Xaa Lys Xaa
        275                 280                 285

Leu Pro Leu Trp Ala Xaa Xaa Val Ala Xaa Phe Ser Tyr Asn Trp Thr
        290                 295                 300

Phe Tyr Thr Xaa Leu Xaa Leu Leu Pro Thr Xaa Met Lys Xaa Xaa Leu
305                 310                 315                 320

Arg Phe Asn Xaa Gln Glu Asn Gly Phe Leu Ser Xaa Xaa Pro Tyr Leu
            325                 330                 335

Xaa Xaa Trp Leu Cys Met Ile Leu Xaa Gly Gln Ala Ala Asp Asn Leu
            340                 345                 350

Arg Ala Xaa Trp Asn Phe Ser Thr Xaa Xaa Val Xaa Arg Xaa Phe Ser
        355                 360                 365

Leu Ile Xaa Met Ile Gly Pro Xaa Xaa Phe Leu Xaa Xaa Xaa Xaa Xaa
        370                 375                 380

Xaa Gly Cys Asp Tyr Xaa Leu Xaa Val Xaa Phe Leu Xaa Ile Ser Thr
385                 390                 395                 400

Xaa Leu Gly Gly Phe Cys Ser Ser Gly Phe Ser Ile Asn His Leu Xaa
                405                 410                 415

Ile Ala Pro Ser Tyr Ala Gly Xaa Leu Leu Gly Ile Thr Asn Xaa Phe
                420                 425                 430

Ala Thr Ile Xaa Gly Met Xaa Gly Pro Xaa Ile Xaa Xaa Ser Xaa Thr
        435                 440                 445

Pro Xaa Asn Thr Xaa Gly Glu Trp Gln Xaa Xaa Phe Xaa Xaa Ala Ala
    450                 455                 460

Ala Xaa Asn Xaa Phe Gly Ala Ile Phe Xaa Thr Leu Phe Ala Lys Gly
465                 470                 475                 480

Glu Xaa Gln Asn Trp Xaa Xaa Xaa Asp His Xaa Gly His Arg Xaa
                485                 490                 495
```